US006331388B1

(12) United States Patent
Malkovsky et al.

(10) Patent No.: US 6,331,388 B1
(45) Date of Patent: *Dec. 18, 2001

(54) IMMUNE RESPONSE ENHANCER

(75) Inventors: Miroslav Malkovsky, Madison, WI (US); Andrew D. Wells, Mt. Laurel, NJ (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/955,565

(22) Filed: Oct. 17, 1997

(51) Int. Cl.[7] .................. A61K 31/7088; C12N 5/00; G01N 33/569

(52) U.S. Cl. ................ 435/5; 424/278.1; 435/7.21; 435/7.22; 435/7.23; 435/7.24; 435/7.31; 435/7.32; 435/69.1; 435/375; 514/44

(58) Field of Search .................. 435/5, 7.21, 7.22, 435/7.23, 7.24, 7.31, 7.32, 69.1, 375; 424/278.1; 514/44

(56) References Cited

U.S. PATENT DOCUMENTS

| 5,399,346 | 3/1995 | Anderson et al. | 424/93.21 |
| 5,651,993 | * 7/1997 | Edelson et al. | 424/534 |
| 5,830,464 | * 11/1998 | Srivastava | 424/278.1 |

OTHER PUBLICATIONS

Hodgson, Expert Opin. Ther. Patents, 5, 449–468, 1995.*
Miller et al, The FASEB Journal, 9, 190–199, 1995.*
Orkin et al, "Report and Recomendations" of the Panel To Assess the NIH Investment in Research on Gene Therapy, 1995.*
Silva et al, Microbial Pathogenesis, 12, 27–38, 1992.*
Restifo et al. (1991) "Defective Presentation of Endogenous Antigens by a Murine Sarcoma, Implications for the Failure of an Anti–Tumor Immune Response," J. Immunol. 147:1453–1459.
Restifo et al. (1992) "A Nonimmunogenic Sarcoma Transduced with the cDNA for Interferon γ Elicits CD8[+] T Cells against the Wild–type Tumor: Correlation with Antigen Presentation Capability," J. Exp. Med. 175:1423–1431.
Restifo et al. (1993) "Identification of Human Cancers Deficient in Antigen Processing," J. Exp. Med. 177:265–272.
Kuroda et al. (1995) "Characterization of defectiveness in endogenous antigen presentation of novel murine cells established from methylcholanthrene–induced fibrosarcomas," Immunology 84:153–158.

Kaklamanis et al. (1995) "Loss of Transporter in Antigen Processing 1 Transport Protein and Major Histocompatibility Complex Class I Molecules in Metastatic versus Primary Breast Cancer," Cancer Res. 55:5191–5194.
Tanaka et al. (1988) "Rejection of B16 Melanoma Induced by Expression of a Transfected major Histocompability Complex Class I Gene," Mol. Cell. Biol. 8:1857–1864.
Guo et al. (1994) "Effective Tumor Vaccine Generated by Fusion of Hepatoma Cells with Activated B Cells," Science 263:518–520.
Maniatis et al. (1987) "Regulation of Inducible and Tissue–Specific Gene Expression," Science 236:1237–1245.
Voss et al. (1986) "The role of enhancers in the regulation of cell–type–specific transcriptional control," Trends Biochem. Sci. 11:287–289.
Sambrook et al. (1989) Molecular Cloning: A Laboratory Manual, 2nd ed., Cold Spring Harbor Laboratory Press, New York, pp. 16.6–16.15.
Hartl (1996) "Molecular chaperones in cellular protein folding," Nature 381:571–580.
Germain and Hendrix (1991) "MHC class II structure, occupancy and surface expression determined by post–endoplasmic reticulum antigen binding," Nature 353:134–139.
Neefjes et al. (1993) "Selective and ATP–Dependent Translocation of Peptides by the MHC–Encoded Transporter," Science 261:769–771.
Sanderson et al. (1994) "Accumulation of HLA–DM, a Regulator of Antigen Presentation, in MHC Class II Compartments," Science 266:1566–1569.
Fung–Leung et al. (1996) "Antigen Presentation and T Cell Development in H2–M–Deficient Mice," Science 271:1278–1281.
Rees et al. (1991) "Stress–induced moduclation of antigen-presenting cell function," Immunology 74:386–392.
Mariéthoz et al. (1994) "Exposure of monocytes to heat shock does not increase class II expression but modulates antigen–dependent T cell responses," Int. Immunol. 6:925–930.

(List continued on next page.)

Primary Examiner—David Saunders
(74) Attorney, Agent, or Firm—Medlen & Carroll, LLP

(57) ABSTRACT

The present invention provides methods for specifically increasing expression of MHC class I molecules in cells, and in particular, in poorly immunogenic tumor cells as well as in pathogen-infected cells. Also provided by the present invention are methods for increasing presentation of endogenous antigens onto the cell surface by MHC class I molecules, as well as methods of increasing the immunity of an animal against an antigen. The methods presented herein are useful in enhancing immune recognition of any cell infected with any pathogen, for in vitro and in vivo screening of candidate immunogene therapeutic approaches, and for enhancing the generation of antibodies to an otherwise poorly immunogenic antigen or cell. The present invention further provides methods for reducing or increasing the radiation sensitivity of a cell.

14 Claims, 61 Drawing Sheets

OTHER PUBLICATIONS

Michalek et al. (1992) "The Class II MHC–Restricted Presentation of Endogenously Synthesized Ovalbumin Displays Clonal Variation, Requires Endosomal/Lysosomal Processing, and is Up–Regulated by Heat Shock," J. Immunol. 148:1016–1024.

Jackson et al. (1994) Regulation of MHC Class I Transport by the Molecular Chaperone, Calnexin (p88, IP90), Science 263:384–387.

Rajagopalan et al. (1994) "Retention of Unassembled Components of Integral Membrane Proteins by Calnexin," Science 263:387–390.

Srivastava (1991) "Protein tumor antigens," Curr. Op. Immunol. 3:654–658.

Srivastava and Maki (1991) "Stress–Induced Proteins in Immune Response to Cancer," Curr. Top. Microbiol. Immunol. 167:109–123.

Udono and Srivastava (1993) "Heat Shock Protein 70–associated Peptides Elicit Specific Cancer Immunity," J. Exp. Med. 178:1391–1396.

Udono et al. (1994) "Cellular requirements for tumor–specific immunity elicited by heat shock proteins: Tumor rejection antigen gp96 primes CD8+ T cells in vivo," Proc. Natl. Acad Sci. USA 91:3077–3081.

Srivastava et al. (1994) "Heat shock proteins transfer peptides during antigen processing and CTL priming," Immunogenetics 39:93–98.

Arnold et al. (1995) "Cross–priming of Minor Histocompatibility Antigen–specific Cytotoxic T Cells upon Immunization with the Heat Shock Protein gp96," J. Exp. Med. 182:885–889.

Lussow et al. (1991) "Mycobacterial heat–shock proteins as carrier molecules," Eur. J. Immunol. 21:2297–2302.

Barrios et al. (1992) "Mycobacterial heat–shock proteins as carrier molecules. II: The use of the 70–KDA mycobacterial heat–shock protein as carrier for conjugated vaccines can circumvent the need for adjuvants and Bacillus Calmette Guérin priming," Eur. J. Immunol. 22:1365–1372.

Suzue and Young (1996) "Adjuvant–Free hsp70 Fusion Protein System Elicits Humoral and Cellular Immune Responses to HIV–1 p24," J. Immunol. 156:873–879.

Suto and Srivastava (1995) "A Mechanism for the Specific Immunogenicity of Heat Shock Protein–Chaperoned Peptides," Science 269:1585–1588.

Pinhasi–Kimhi et al. (1986) "Specific interaction between teh p53 cellulr tumour antigen and major heat shock proteins," Nature 320:182–184.

Hainaut and Milner (1992) "Interaction of heat–shock protein 70 with p53 translated in vitro: evidence for interaction with dimeric p53 and for a role in the regulation of p53 conformation," EMBO J. 11:3513–3520.

Finlay et al. (1988) "Activating Mutations for Transformation by p53 Produce a Gene Product that Forms an hsc70–p53 Complex with an Altered Half–Life," Mol. and Cell. Biol. 8:531–539.

Fisch et al. (1990) "Recognition by Human Vγ9/Vδ2 T Cells of a GroEl Homolog on Daudi Burkitt's Lymphoma Cells," Science 250:1269–1273.

Tamura et al. (1993) "70 kDA Heat Shock Congnate Protein is a Transformation–Associated Antigen and a Possible Target for the Host's Anti–Tumor Immunity," J. Immunol. 151:5516–5524.

Lukacs et al. (1993) "Tumor Cells Transfected with a Bacterial Heat–Shock Gene Lose Tumorigenicity and Induce Protection against Tumors," J. Exp. Med. 178:343–348.

Graham and Prevec (1991) "Manipulation of Adenovirus Vectors," Meth. Mol. Biol. 7:109–128.

Engelhardt et al. (1994) "Ablation of E2A in recombinant adenoviruses improves transgene persistence and decreases inflammatory response in mouse liver," Proc. Natl. Acad. Sci. USA 91:6196–6200.

Goding (1986) In "Monoclonal Antibodies: Principles and Practice," Academic Press, pp 59–103.

Takebe et al. (1988) "SRα Promoter: an Efficient and Versatile Mammalian cDNA Expression System Composed of the Simian Virus 40 Earily Promoter and the R–U5 Sgment of Human T–Cell Leukemia Virus Type 1 Long Terminal Repeat," Mol. Cell. Biol. 8:466–472.

Crystal (1995) "Transfer to Genes to Humans: Early Lessons and Obstacles to Success," Science 270:404–410.

Marshall (1995) "Gene Therapy's Growing Pains," Science 269:1050–1055.

Schirmbeck and Reimann (1994) "Peptide transporter–independent, stress protein–mediated endosomal processing of endogenous protein antigens for a major histocompatibility complex class I presentation," Eur. J. Immunol. 24:1478–1486.

Sibille et al. (1992) "A defect in the presentation of intracellular viral antigens is restored by interferon–γ in cell lines with impaired major histocompatibility complex class I assembly," Eur. J. Immunol. 22:433–440.

Udono and Srivastava (1994) "Comparison of Tumor–Specific Immunogenicities of Stress–Induced Proteins gp96, hsp90, and hsp70," J. Immunol. 152:5398–5403.

Wang et al. (1994) "A Monoclonal Antibody That Recognizes HLA–B27 in the Context of Peptides," J. Immunol. 152:1197–1205.

Wells et al. (1997) "Restoration of MHC class I surface expression and endogenous antigen presentation by a molecular chaperone," Scand. J. Immunol. 45:605–612.

Andrew Dale Wells, "Role Of Cytosolic Heat Shock Proteins In The Processing And Presentatio Of Endogenous Antigens By Tumor Cells," Dissertation University of Wisconsin Memorial Library made available on Nov. 13, 1996.

* cited by examiner

Figure 1

```
   1 cgccatggag accaacaccc ttcccaccgc cactccccct tcctctcagg gtccctgtcc
  61 cctccagtga atcccagaag actctggaga gttctgagca gggggcggca ctctggcctc
 121 tgattggtcc aaggaaggct ggggggcagg acgggaggcg aaacccctgg aatattcccg
 181 acctggcagc ctcatcgagc tcggtgattg gctcagaagg gaaaaggcgg gtctccgtga
 241 cgacttataa aagcccaggg gcaagcggtc cggataacgg ctagcctgag gagctgctgc
 301 gacagtccac taccttttc gagagtgact cccgttgtcc caaggcttcc cagagcgaac
 361 ctgtgcggct gcaggcaccg gcgcgtcgag tttccggcgt ccggaaggac cgagctcttc
 421 tcgcggatcc agtgttccgt ttccagcccc caatctcaga gccgagccga cagagagcag
 481 ggaaccgcat ggccaaagcc gcggcagtcg gcatcgacct gggcaccacc tactcctgcg
 541 tgggggtgtt ccaacacggc aaggtggaga tcatcgccaa cgaccagggc aaccgcacca
 601 cccccagcta cgtggccttc acggacaccg agcggctcat cggggatgcg gccaagaacc
 661 aggtggcgct gaaccgcag aacaccgtgt tgacgcgaa gcgcctgatc ggccgcaagt
 721 tcggcgaccc ggtggtgcag tcggacatga agcactggcc tttccaggtg atcaacgacg
 781 gagacaagcc caaggtgcag gtgagctaca aggggagac caaggcattc taccccgagg
 841 agatctcgtc catggtgctg accaagatga aggagatcgc cgaggcgtac ctgggctacc
 901 cggtgaccaa cgccgtgatc accgtgccgg cctacttcaa cgactcgcag cgccaggcca
 961 ccaaggatgc gggtgtgatc gcggggctca acgtgctgcg gatcatcaac gagcccacgg
1021 ccgccgccat cgcctacggc ctggacagaa cgggcaaggg ggagcgcaac gtcctgatct
1081 ttgacctggg cggggggcacc ttcgacgtgt ccatcctgac gatcgacgac ggcatcttcg
1141 aggtgaaggc cacggccggg gacacccacc tgggtgggga ggactttgac aacaggctgg
1201 tgaaccactt cgtggaggag ttcaagagaa aacacaagaa ggacatcagc cagaacaagc
1261 gagccgtgag gcggctgcgc accgcctgcg agagggccaa gaggaccctg tcgtccagca
1321 cccaggccag cctggagatc gactccctgt ttgagggcat cgacttctac acgtccatca
1381 ccagggcgag gttcgaggag ctgtgctccg acctgttccg aagcaccctg gagccgtgg
1441 agaaggctct gcgcgacgcc aagctggaca aggcccagat tcacgacctg gtcctggtcg
1501 ggggctccac ccgcatcccc aaggtgcaga agctgctgca ggacttcttc aacgggcgcg
1561 acctgaacaa gagcatcaac cccgacgagg ctgtgggcta cgggcggcg gtgcaggcgg
1621 ccatcctgat ggggacaag tccgagaacg tgcaggacct gctgctg gacgtggctc
1681 ccctgtcgct ggggctggag acggccggag gcgtgatgac tgccctgatc aagcgcaact
1741 ccaccatccc caccaagcag acgcagatct tcaccaccta ctccgacaac caacccgggg
1801 tgctgatcca ggtgtacgag ggcgagaggg ccatgacgaa agacaacaat ctgttggggc
1861 gcttcgagct gagcggcatc cctccggccc caggcgtgcc ccagatcgag gtgaccttcg
1921 acatcgatgc caacggcatc ctgaacgtca cggccacgga caagagcacc ggcaaggcca
1981 acaagatcac catcaccaac gacaagggcc gcctgagcaa ggaggagatc gagcgcatgg
2041 tgcaggaggc ggagaagtac aaagcggagg acgaggtgca gcgcgagagg gtgtcagcca
2101 agaacgccct ggagtcctac gccttcaaca tgaagagcgc cgtggaggat gagggctca
2161 agggcaagat cagcgaggcc gacaagaaga aggtgctgga caagtgtcaa gaggtcatct
2221 cgtggctgga cgccaacacc ttggccgaga aggacgagtt tgagcacaag aggaaggagc
2281 tggagcaggt gtgtaacccc atcatcagcg gactgtacca gggtgccggt ggtcccgggc
2341 ctgggggctt cggggctcag ggtcccaagg gagggtctgg gtcaggcccc accattgagg
2401 aggtagatta ggggccttc caagattgct gttttttgttt tggagcttca agactttgca
2461 tttcctagta tttctgtttg tcagttctca atttcctgtg tttgcaatgt tgaaattttt
2521 tggtgaagta ctgaacttgc cttttttcc ggtttctaca tgcagagatg aatttatact
2581 gccatcttac gactatttct tctttttaat acacttaact caggccattt tttaagttgg
2641 ttacttcaaa gtaaataaac tttaaaattc aagtgatgcc ctttattcc t
```

C92 (1:2000)

lane

1: B16.pSRαneo

2: B16.pSRαneo.Hsp72 bulk line 3-10: Various subclones of B16.pSRαneo.Hsp72 bulk line

FIG. 9A

```
TCGAACGAGG GGCGTGACCC GGTGCGGGGC TTCTTGCACT CGGCATAGGC GAGTGCTAAG      60
AATAACGTTG GCACTCGCGA CCGGTGAGTG CTAGGTCGGG ACGGTGAGGC CAGGCCCGTC     120
GTCGCAGCGA GTGGCAGCGA GGACAACTTG AGCCGTCCGT CGCGGGCACT GCGCCCGGCC     180
AGCGTAAGTA GCGGGGTTGC CGTCACCCGG TGACCCCCGT TTCATCCCCG ATCCGGAGGA     240
ATCACTTCGC AATGGCCAAG ACAATTGCGT ACGACGAAGA GGCCCGTCGC GGCCTCGAGC     300
GGGGCTTGAA CGCCCTCGCC GATGCGGTAA AGGTGACATT GGGCCCCAAG GGCCGCAACG     360
TCGTCCTGGA AAAGAAGTGG GGTGCCCCCA CGATCACCAA CGATGGTGTG TCCATCGCCA     420
AGGAGATCGA GCTGGAGGAT CCGTACGAGA AGATCGGCGC CGAGCTGGTC AAAGAGGTAG     480
CCAAGAAGAC CGATGACGTC GCCGGTGACG GCACCACGAC GGCCACCGTG CTGGCCCAGG     540
CGTTGGTTCG CGAGGGCCTG CGCAACGTCG CGGCCGGCGC CAACCCGCTC GGTCTCAAAC     600
GCGGCATCGA AAAGGCCGTG GAGAAGGTCA CCGAGACCCT GCTCAAGGGC GCCAAGGAGG     660
TCGAGACCGA GGAGCAGATT GCGGCCACCG CAGCGATTTC GGCGGGTGAC CAGTCCATCG     720
GTGACCTGAT CGCCGAGGCG ATGGACAAGG TGGGCAACGA GGGGCGTCAT ACCGTCGAGG     780
AGTCCAACAC CTTTGGGCTG CAGCTCGAGC TCACCGAGGG TATGCGGTTC GACAAGGGCT     840
ACATCTCGGG GTACTTCGTG ACCGACCCGG AGCGTCAGGA GGCGGTCCTG GAGGACCCCT     900
ACATCCTGCT GGTCAGCTCC AAGGTGTCCA CTGTCAAGGA TCATCGCCGA GGCGAGGCGC     960
AGGTCATCGG AGCCGGTAAG CCGCTGCTGA TCATCGCCGA GGACGTCGAG GGCGAGGCTC    1020
TGTCCACCCT GGTCGTCAAC AAGATCCGCG GCACCTTCAA GTCGGTGGCG GTCAAGGCTC    1080
CCGGCTTCGG CGACCGCCGC AAGGCGATGC TGCAGGATAT GGCCATTCTC ACCGGTGGTC    1140
AGGTGATCAG CGAAGAGGTC GGCCTGACGC TGGAGAACGC CGACCTGTCG CTGCTAGGCA    1200
AGGCCCGCAA GGTCGTGGTC ACCAAGGACG AGACCACCAT CGTCGAGGGC GCCGGTGACA    1260
```

FIG. 9B

```
CCGACGCCAT CGCCGGACGA GTGGCCCAGA TCCGCCAGGA GATCGAGAAC AGCGACTCCG   1320
ACTACGACCG TGAGAAGCTG CAGGAGCGGC TGGCCAAGCT GGCCGGTGGT GTCGCGGTGA   1380
TCAAGGCCGG TGCCGCCACC GAGGTCGAAC TCAAGGAGCG CAAGCACCGC ATCGAGGATG   1440
CGGTTCGCAA TGCCAAGGCC GCCGTCGAGG AGGGCATCGT CGCCGGTGGG GGTGTGACGC   1500
TGTTGCAAGC GGCCCCCGACC CTGGACGAGC TGAAGCTCGA AGGCGACGAG GCGACCGGCG   1560
CCAACATCGT GAAGGTGGCG CTGGAGGCCC CGCTGAAGCA GATCGCCTTC AACTCCGGGC   1620
TGGAGCCGGG CGTGGTGGCC GAGAAGGTGC GCAACCTGCC GGCTGGCCAC GGACTGAACG   1680
CTCAGACCGG TGTCTACGAG GATCTGCTCG CTGCCGGCGT TGCTGACCCG GTCAAGGTGA   1740
CCCGTTCGGC GCTGCAGAAT GCGGGCGTCCA TCGCGGGGCT GTTCCTGACC ACCGAGGCCG   1800
TCGTTGCCGA CAAGCCGGAA AAGGAGAAGG CTTCCGTTCC CGGTGCGGGC GACATGGGTG   1860
GCATGGATTT CTGACCCCGG CGAGAAGTCG CAGCGAGGAG CCCGGTCCCT TTGTGGGGCC   1920
GGGCTCCTCT GGTTGGGAGC TACGGTACCG AGAACACCAC GCAGTCGTGT AGGCAACCTT   1980
TGGCCCGCTGT GGGCGAGTCG GGGGCCGCGT CTCGGTGCAG CAGCGCGCGG ATGGGTACGA   2040
CACCGCAGCG GGCGGTGTCG TCATCGGGGC CTGCGTCCGA CGCCTGGGCA CGGCCGTCGA   2100
CGATCAGCGA GTAGCCGCTA GGATCGGATG GCGGCCACAA CAGGGTGACT TCGCTGCGGT   2160
GGGCCAGGTT TTGCCGCGTA CGACCCCCGA TCAGCCGGAC GTCGACCACT GCCCGGGGTC   2220
CATCGGGGCC GTCGGGGAGT TCGCGCAGCA CCGGCTCGAC TGCCACCGTG TGCACGCGAT   2280
GGCCATCATC GACGGTGATC AGGTAAGCGA ACGGGTAGTC GGGCAAGGCG GCGGCCAGCC   2340
GTTTGAGGTC TACCTTTTTG GCACCCACGG ATTCGAGGAT AGGCGCCCGA TGTGTTACTC   2400
CGAACCGACC GGCTGCCCGA TCCGCGGGCT GGCGTAGGCG GATTCGCGGT CGGGGCTCGG   2460
GTAGAAGTTC GACTTGGGGA TGCCCGAGCC GGGGTACTC GGCTCACGCA CGGCGGTATT   2520
```

FIG. 9C

```
CCGCAAGCCC GAGTCGTTGC TGCCCGAGTT GACGAAGCTC GGGTAGCTGG TGCCAGGGCT  2580
TCTAAGGCCC GGGTTTGCGC CCGAGCCAGC CGCGGGCACTG CCGCTACCGG GGTTCGGGTT  2640
GCCTGAGTCC AGGCCGCCAA CAGGAGCACT GGCCGGGGCG GCGACGGGCG TGTTGGTCAG  2700
GCCCGAGTTG AGGACGTTCG CCAGGCCGTG TTGGAGACCG CCCGTTGATC CGAGGGCGGA  2760
GGCGAGGATG CCCGAACTCA AAGCCGCCGT GCTCATGCCG CCGGTGGCGT AGCCGGCGGA  2820
GCTGACCAAG GCCGCCTCCG AGCCAGCCGC GCTTCCTAAG GCGGGCGTTTT GCATCCCCGC  2880
GTTCCAGAAG CTGGTGTTGA GGCTGCCTGC GCTGCCGAGG CCCGCGTTGA TTGTCCCCGA  2940
GGTCCCGATG CCGCTGTTCA GGGAGCCCGA ATTCCCGATG CCGATGTTTC CGCTGCCGGA  3000
GTTGAATAAG CCGACGTTGC CGGTGCCCGA GTTCCCGAAG CCGATGTTGC CGCTACCCGA  3060
GTTGAAGCCG CCGAAACCCA TCTGGTGATC ACCGGTGATC CCGAACCCGA TATTCCCGCT  3120
ACCGGTGTTG CCGAAGCCGA TATTCCCGTC GCCGAGGTTG CCGAGGCCCA GGTTGCCGCT  3180
GCCGGTGTTG CCGCTGCCGA TGTTGCCGGT GCCGGTGTTG CCGCTGCCGA TGTTGTTGTT  3240
GCCGATGTTG TTGTTGCCGA TGTTGTTGTT GCCGATGTTG CCGCTGCCGG TGTTGCCGAA  3300
GCCCAGATTG ATCTGGCCGT TCTTGCCGAT GTCGATGCCG AGTTCCGCA AGACCTGCTG  3360
CCAGGGCGCC AGTTGTGCGA CGGCCGCAGA CGCATCGAAG TGGTAACCAG CCATCGCCGC  3420
CACGTCCAAT GCCCACATTT GCTCGTATGC CGCCTCGACG TCCATGAGCG CCGGAGCGTT  3480
CTGCCCAAAC CAGTTCGTAG CTGCCAGCAG CTGCATCAGG CCACGATTGG CCGCTACCAC  3540
TGCCGGCTGC ACGGTGGCCG CCAGCGCCGC CTCGAACGCG GTCGCTGTTG CCATGGCCTG  3600
TGCGGCCGCT TGTTCCGCCT GCGCTGCCGC CGTGCTGAGC CAGGCTAGGT ACTGGGTTGC  3660
GACGGCCATC ATCGCCGCCG CGGACGGACC CAGCCAGGCG CCACTAGTCA GTTCGGATGT  3720
GACGAGCCA AGCGACGCTA TTGACGCGAG CAATTCTTCG GCCAGCTCGC CCCAGGCGGT  3780
GGCCGCAGCA ATTAGCGGTC CCGACCCGGG ACCGGCAAAC ATCAGTGCCG AATTGATCTC  3840
```

FIG. 9D

| | | | | | | |
|---|---|---|---|---|---|---|
| TGGGGGCAAC | CACGCAAAAT | GCGGGCTTGT | CAGCCGATCC | AACTTAACTG | TCAGCGACCG | 3900 |
| TTGCCGTGGC | GGTATCGGCA | CTTCAATACC | ACTCATCTTT | GGGGTCATCT | TTGGAGCGCC | 3960 |
| CCTAGGAACC | GCCAGCTTAC | CTAGTCCCGG | GTAGGGGCCG | ACTGGGCGGC | GGGATGCAGC | 4020 |
| TGAGGGTCTG | CCACCTGCCC | CGTAAATGTCG | CTGGTATGGC | AAGCACCGAC | GCCGCGGCCC | 4080 |
| AAGAGTTGCT | CCGGACGCG | TTCACCCGGT | TGATCGAACA | TGTCGACGAA | CTCACCGACG | 4140 |
| GCCTCACCGA | CCAACTCGCC | TGCTACCGCC | CGACCCCCAG | CGCCAACAGC | ATTGCGTGGC | 4200 |
| TGCTCTGGCA | CAGCGCCCGG | GTGCAGGATA | TACAGGTCGC | CCATGTGTGGCC | GGCGTGGAAG | 4260 |
| AGGTGTGGAC | CCGGCGACGGT | TGGGTGGACC | GCTTTGGGTT | AGATCTGCCG | CGGCACGACA | 4320 |
| CCGGATATGG | ACACCGTCCC | GAGGATGTGG | CGAAGGTACG | GGCACCCGCC | GACGGAATTC | 4380 |

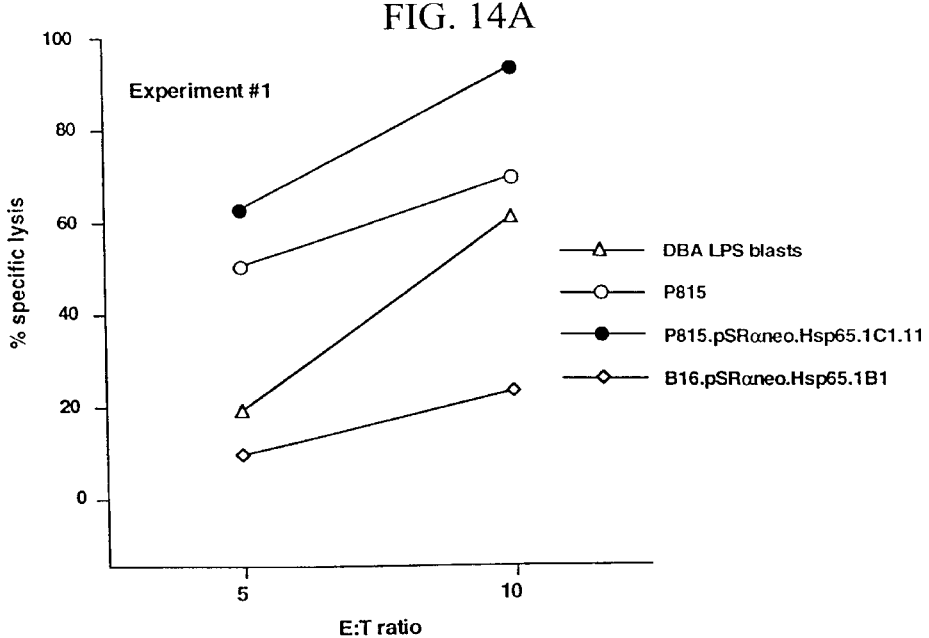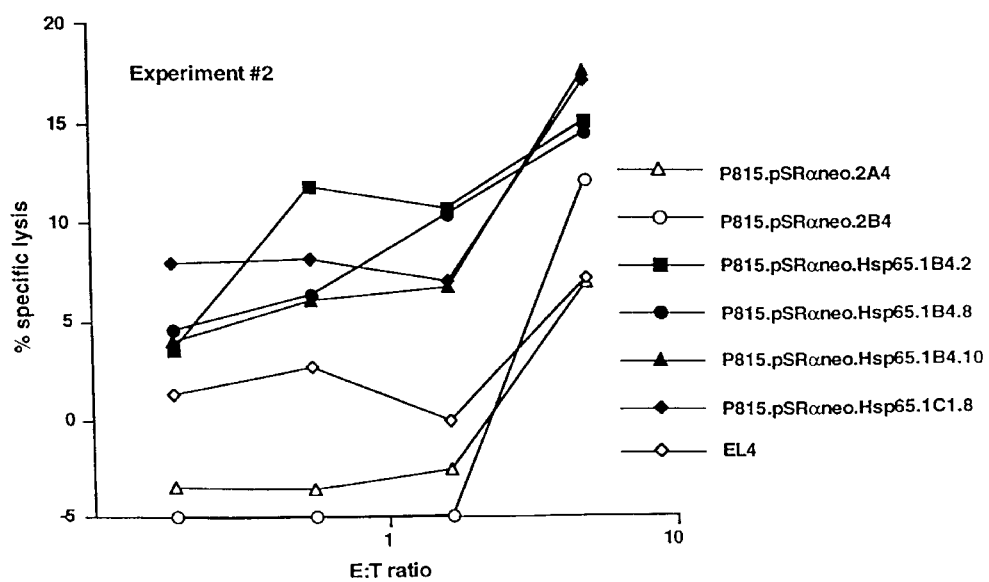

FIG. 16A
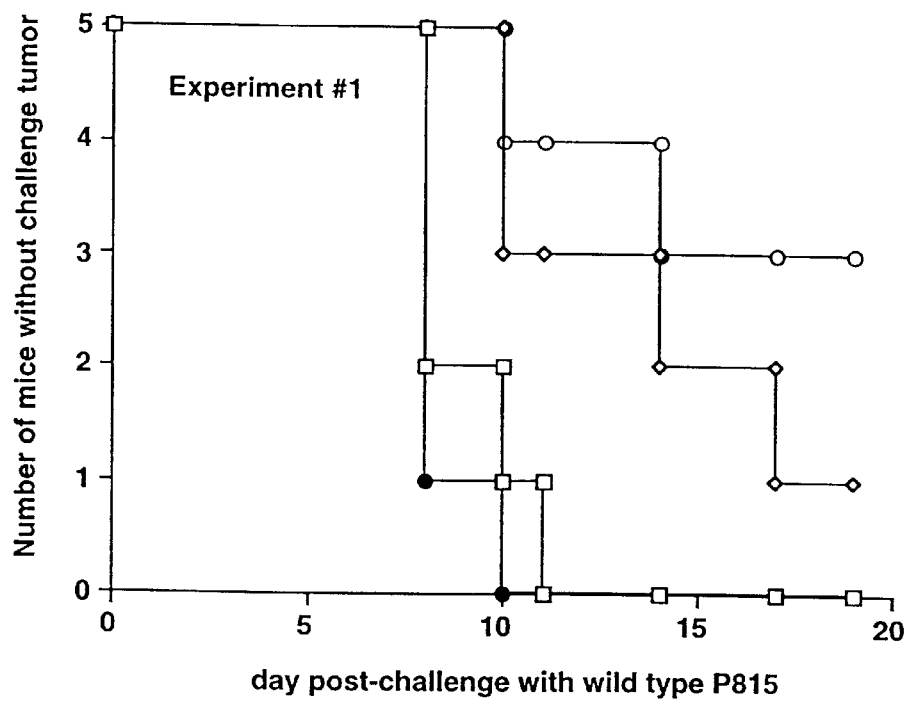
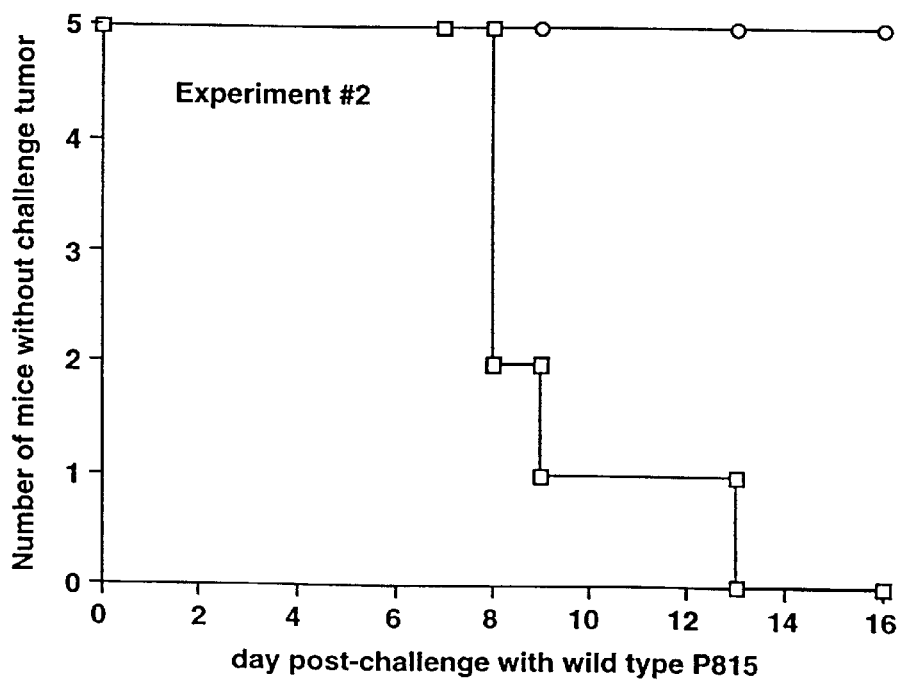

FIG. 16B
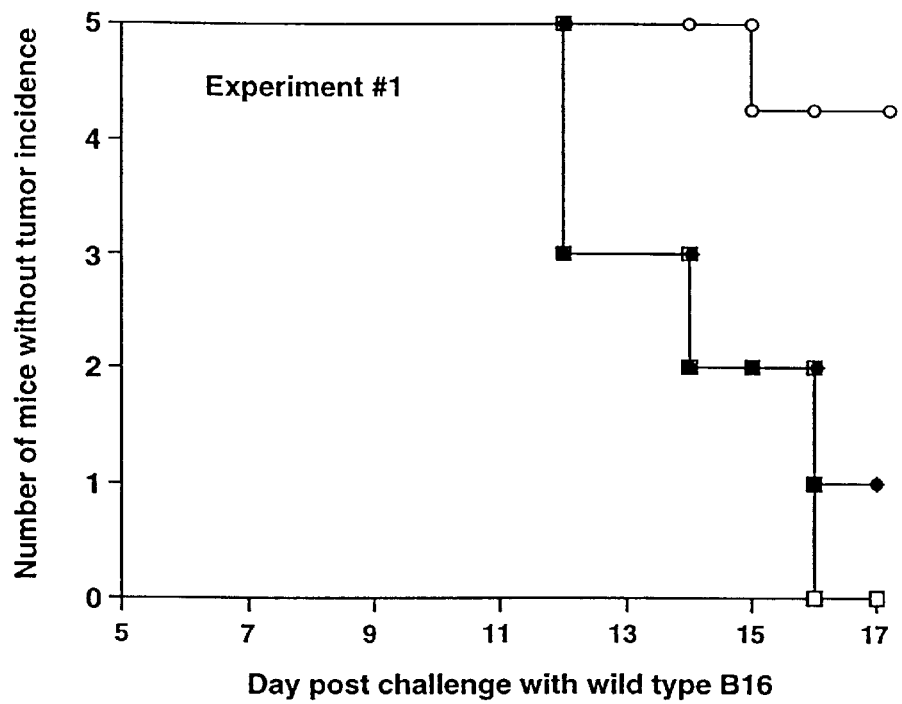
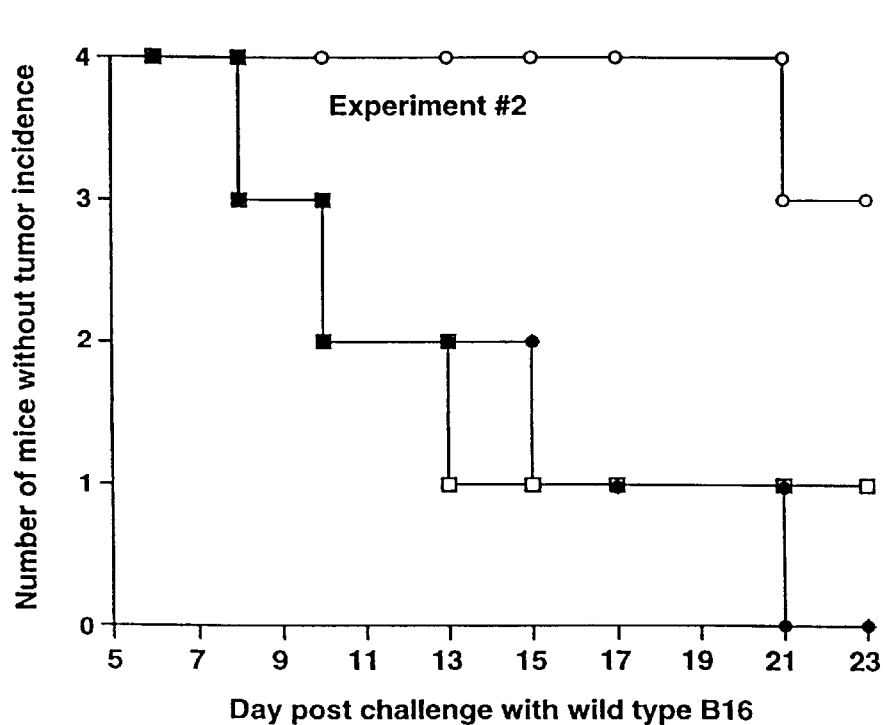

FIG. 21A

```
CGATAAGCTT CTGTGGAATG TGTGTCAGTT AGGGTGTGGA AAGTCCCCAG GCTCCCCAGC    60
AGGCAGAAGT ATGCAAAGCA TGCATCTCAA TTAGTCAGCA ACCAGGTGTG GAAAGTCCCC   120
AGGCTCCCCA GCAGGCAGAA GTATGCAAAG CATGCATCTC AATTAGTCAG CAACCATAGT   180
CCCGCCCCTA ACTCCGCCCA TCCCGCCCCT AACTCCGCCC AGTTCCGCCC ATTCTCCGCC   240
CCATGGCTGA CTAATTTTTT TTATTTATGC AGAGGCCGAG GCCGCCTCGG CCTCTGAGCT   300
ATTCCAGAAG TAGTGAGGAG GCTTTTTTTG AGGCCTAGGC TTTTGCAAAA AGCTCCTCCG   360
ATCGAGGGGC TCGCATCTCT CCTTCACGCG CCCGCCGCCC TACCTGAGGC CGCCATCCAC   420
GCCGGTTGAG TCGCGTTCTG CCCGCTCCCG CCTGTGGTGC CTCCTGAACT GGTCCGCCG    480
TCTAGGTAAG TTTAAAGCTC AGGTCGAGAC CGGGCCTTTG TCCGGCGCTC CCTTGGAGCC   540
TACCTAGACT CAGCCGGCTC TCCACGCTTT GCCTGACCCT GCTTGCTCAA CTCTACGTCT   600
TTGTTTCGTT TTCTGTTCTG CGCCGTTACA GATCCAAGCT GCCTCGAGGA ACTGAAAAAC   660
CAGAAAGTTA ACTGGTAAGT TTAGTCTTTT TGTCTTTTAT TTCAGTCCC GGATCCGGTG    720
GTGCAAATCA AAGAACTGCT CCTCAGTGGA TGTTGCCTTT ACTTCTAGGC CTGTACGGAA   780
GTGTTACTTC TGCTCTAAAA GCTGCTGCAG AGCTTATCGA TGATAAGCTG TCAAACATGA   840
GAATTCCAAC CTTTCTGGTT TTTTGCGTTT CCCGTCAACA GTATCTTCCC CTTCACAAAA   900
TTGCAGCAAA AGCTCTAAAA CAAACACAAA AAGGCGTTGA GCTGTTTTTT TACTTTCAGT   960
CCATGACCTA CTATCTTCCC CTTCACAAAA TTGCAGCAAA AGCTCTAAAA CAAACACAAA  1020
AAGGCGTTGA GCTGTTTTTT TACTTTCAGT CCATGGCCTG AAATAACCTC CGAACCTTAA  1080
GCGTGACAGC CGGCGCAGCA CCATGACCTA AAATAACCTC TGAAAGAGGA ACTTGGTTAG  1140
GGGTACCTTC TGAGGCGGAA AGAACCAGCC GGATCCCCTCG AGGATCCAGA CATGATAAGA  1200
TACATTGATG AGTTTGGACA AACCACAACT AGAATGCAGT GAAAAAAATG CTTTATTTGT  1260
```

FIG. 21B

```
GAAATTTGTG ATGCTATTGC TTTATTTGTA ACCATTATAA GCTGCAATAA ACAAGTTAAC    1320
AACAACAATT GCATTCATTT TATGTTTCAG GTTCAGGGGG AGGTGTGGGA GGTTTTTTAA    1380
AGCAAGTAAA ACCTCTACAA ATGTGGTATG GCTGATTATG ATCCTGCCTC GCGCGTTTCG    1440
GTGATGACGG TGAAAACCTC TGACACATGC AGCTCCCGGA GACGGTCACA GCTTGTCTGT    1500
AAGCGGATGC CGGGAGCAGA CAAGCCCGTC AGGGCGCGTC AGCGGGTGTT GGCGGGTGTC    1560
GGGGCGCAGC CATGACCCAG TCACGTAGCG ATAGCGGAGT GTATACTGGC TTAACTATGC    1620
GGCATCAGAG CAGATTGTAC CGTCGACCGG TGTGAAATAC CGCACAGATG               1680
CGTAAGGAGA AAATACCGCA TCAGGCGCTC TTCCGCTTCC TCGCTCACTG ACTCGCTGCG    1740
CTCGGTCGTT CGGCTGCGGC GAGCGGTATC AGCTCACTCA AAGGCGGTAA TACGGTTATC    1800
CACAGAATCA GGGGATAACG CAGGAAAGAA CATGTGAGCA AAAGGCCAGC AAAAGGCCAG    1860
GAACCGTAAA AAGGCCGCGT TGCTGGCGTT TTTCCATAGG CTCCGCCCCC CTGACGAGCA    1920
TCACAAAAAT CGACGCTCAA GTCAGAGGTG GCGAAACCCG ACAGGACTAT AAAGATACCA    1980
GGCGTTTCCC CCTGGAAGCT CCCTCGTGCG CTCTCCTGTT CCGACCCTGC CGCTTACCGG    2040
ATACCTGTCC GCCTTTCTCC CTTCGGGAAG CGTGGCGCTT TCTCAATGCT CACGCTGTAG    2100
GTATCTCAGT TCGGTGTAGG TCGTTCGCTC CAAGCTGGGC TGTGTGCACG AACCCCCCGT    2160
TCAGCCCGAC CGCTGCGCCT TATCCGGTAA CTATCGTCTT GAGTCCAACC CGGTAAGACA    2220
CGACTTATCG CCACTGGCAG CAGCCACTGG TAACAGGATT AGCAGAGCGA GGTATGTAGG    2280
CGGTGCTACA GAGTTCTTGA AGTGGTGGCC TAACTACGGC TACACTAGAA GGACAGTATT    2340
TGGTATCTGC GCTCTGCTGA AGCCAGTTAC CTTCGGAAAA AGAGTTGGTA GCTCTTGATC    2400
CGGCAAACAA ACCACCGCTG GTAGCGGTGG TTTTTTTGTT TGCAAGCAGC AGATTACGCG    2460
CAGAAAAAAA GGATCTCAAG AAGATCCTTT GATCTTTTCT ACGGGGTCTG ACGCTCAGTG    2520
```

FIG. 21C

```
GAACGAAAAC TCACGTTAAG GGATTTTGGT CATGAGATTA TCAAAAAGGA TCTTCACCTA    2580
GATCCTTTTA AATTAAAAAT GAAGTTTTAA ATCAATCTAA AGTATATATG AGTAAACTTG    2640
GTCTGACAGT TACCAATGCT TAATCAGTGA GGCACCTATC TCAGCGATCT GTCTATTTCG    2700
TTCATCCATA GTTGCCTGAC TCCCCGTCGT GTAGATAACT ACGATACGGG AGGGCTTACC    2760
ATCTGGCCCC AGTGCTGCAA TGATACCGCG AGACCCACGC TCACCGGCTC CAGATTATC    2820
AGCAATAAAC CAGCCAGCCG GAAGGGCCGA GCGCAGAAGT GGTCCTGCAA CTTTATCCGC    2880
CTCCATCCAG TCTATTAATT GTTGCCGGGA AGCTAGAGTA AGTAGTTCGC CAGTTAATAG    2940
TTTGCGCAAC GTTGTTGCCA TTGCTACAGG CATCGTGGTG TCACGCTCGT CGTTTGGTAT    3000
GGCTTCATTC AGCTCCGGTT CCCAACGATC AAGGCGAGTT ACATGATCCC CCATGTTGTG    3060
CAAAAAAGCG GTTAGCTCCT TCGGTCCTCC GATCGTTGTC AGAAGTAAGT TGGCCGCAGT    3120
GTTATCACTC ATGGTTATGG CAGCACTGCA TAATTCTCTT ACTGTCATGC CATCCGTAAG    3180
ATGCTTTTCT GTGACTGGTG AGTACTCAAC CAAGTCATTC TGAGAATAGT GTATGCGGCGA    3240
CCGAGTTGCT CTTGCCCGGC GTCAATACGG GATAATACCG CGCCACATAG CAGAACTTTA    3300
AAAGTGCTCA TCATTGGAAA ACGTTCTTCG GGGCGAAAAC TCTCAAGGAT CTTACCGCTG    3360
TTGAGATCCA GTTCGATGTA ACCCACTCGT GCACCCAACT GATCTTCAGC ATCTTTTACT    3420
TTCACCAGCG TTTCTGGGTG AGCAAAAACA GGAAGGCAAA ATGCCGCAAA AAAGGGAATA    3480
AGGGCGACAC GGAAATGTTG AATACTCATC TTCCTTTTTC AATATTATTG AAGCATTTAT    3540
CAGGGTTATT GTCTCATGAG CGGATACATA TTTGAATGTA TTTAGAAAAA TAAACAAATA    3600
GGGGTTCCGC GCACATTTCC CCGAAAAGTG CCACCTGACG TCTAAGAAAC CATTATTATC    3660
ATGACATTAA CCTATAAAAA TAGGCGTATC ACGAGGCCCT TTCGTCTTCA AGTCGACCT    3720
CATGTTTGAC AGCTTATCAT                                                3740
```

IMMUNE RESPONSE ENHANCER

This invention was made with United States government support awarded by NIH Grant Number RR00167. The United States government has certain rights in this invention.

FIELD OF THE INVENTION

The present invention relates to enhancing the immunogenicity of an antigen and to altering radiation resistance of cells. In particular, the present invention provides methods for increasing the presentation of endogenous antigens on a cell surface, for producing antibodies against poorly immunogenic antigens, for immunotherapy of cancer and of pathogen infections, and for enhancing or reducing radiation resistance of cells.

BACKGROUND OF THE INVENTION

While the immune system is adept at recognizing and neutralizing the effects of various pathogens (e.g., bacteria, viruses, fungi, protozoa, and metazoa) and mutated self-cells (e.g., pre-cancer and cancer cells), failure of the immune system to perform its functions often results in disease (e.g., infection and cancer).

Infection of humans with various pathogens continues to present a serious problem with significant clinical and economic consequences. Treatment of many human infections is either problematic (treatment-resistant strains, toxicity of the treatment, drugs not reaching well the infection site, etc.) or practically nonexistent (e.g., viral infections).

To date, cancer remains the single most common cause of morbidity and mortality of humans. Using animal models, the art has long recognized that protective immunity against cancer could be achieved by first exposing the animal to tumor cells in a non lethal manner. These early studies showed that tumors could be categorized as immunogenic or nonimmunogenic based on their ability to induce immunity to a subsequent challenge. Furthermore, tumor antigenicity appeared to be clonal in nature, such that immunization with a certain tumor elicited an immune response capable of rejecting only that same tumor. In addition, immunological memory and tumor rejection were determined to be mediated by T lymphocytes.

Much effort has focused on the identification of tumor-associated antigens. To date, the majority of tumor-associated antigens represent major histocompatibility (MHC) class I-restricted T cell epitopes. These epitopes are generally derived from proteins which have undergone mutation during tumorigenesis, which are normally expressed at a stage in embryogenesis preceding development of the immune system, or are present in overabundance in cancerous tissue compared to normal tissue (Urban and Schreiber (1992) Ann. Rev. Immunol. 10:617–644).

Although identification of these tumor-associated antigens was valuable to the study of tumor immunogenicity, identification of these antigens did not provide a suitable approach to the prevention or treatment of a wide spectrum of cancers since these antigens were rarely shared between tumors of distinct origin. Furthermore, for tumor clearance and long-term protection against tumor growth, expression of tumor-associated antigens further requires recruitment of T cells to its location, presentation of the antigenic peptides to tumor-specific T cells, and the provision of co-stimulatory signals.

One of the approaches to enhancing tumor antigenicity has focused on enhancing T cell recruitment and activation by direct genetic modification of tumor cells to express various cytokines (such as interleukin-2 (IL-2) or interleukin-12 (IL-12)) which function in the recruitment and activation of T cells, and which are also enhanced if high levels of myeloid chemokines are present at the site of the tumor. Chemokines recruit "professional" antigen presenting cells such as macrophages and dendritic cells, which then provide the co-stimulatory signals required for T cell activation. An alternative approach to enhancing tumor antigenicity has employed direct genetic modification of tumor cells to express costimulatory molecules (such as B7-1 or B7-2) and hence to enhance primary anti-tumor T cell responses.

While expression of cytokines and costimulatory molecules has been effective in enhancing primary-anti-tumor T cell responses, such expression does not restore immunogenicity of poorly immunogenic tumors. This result is explained, in part, by the defective presentation by many poorly immunogenic murine and human cancers of endogenous antigens as a result of a diminished synthesis of major histocompatibility complex class I, proteasome components or peptide transporters associated with antigen processing (Restifo et al. (1991) J. Immunol. 147:1453–1459; Restifo et al. (1992) J. Exp. Med. 175:1423–1431; Restifo et al. (1993) J. Exp. Med. 177:265–272; Kuroda et al. (1995) Immunology 84:153–158; Kaklamanis et al. (1995) Cancer Res. 55:5191–5194). Similarly, while the immunogenicity of poorly immunogenic tumors can in some instances be restored by IFN-γ treatment (Restifo et al. (1992) J. Exp. Med. 175:1423–1431), The therapeutic effect of IFN-γ is unpredictable since the susceptibility of cells within a malignant clone as well as that of various tumors is very variable. Indeed, many cells simply will not upregulate the MHC class I molecules when exposed to IFN-γ.

Another approach to enhancing tumor antigenicity has relied on transfection of tumor cells with an MHC class I gene under the control of a heterologous promoter (Tanaka et al. (1988) Mol. Cell. Biol. 8:1857–1864). However, this method does not facilitate peptide-loading and therefore expression of functional MHC-peptide complexes is expected to be low. In addition, this method is not very effective in cells which already express a sufficient amount of MHC.

Yet another approach to enhancing the antigenicity of tumors is by fusion of tumor cells with activated B cells (Guo et al. (1994) Science 263:518–520). However, restoration of immunogenicity is not uniform in tumors from different tissues or different types of tumors from the same tissue. This lack of uniformity is the result, in part, of the random retention by tumor cells of desirable chromosomes (i.e., chromosomes which contain the tumor-antigen coding genes and genes coding for the co-stimulatory or immunopotentiating principle).

Thus, there remains a need for methods for the prevention and treatment of a wide spectrum of infectious pathogens and of cancers, and in particular, poorly immunogenic pathogens and cancers.

SUMMARY OF THE INVENTION

The present invention provides a method of specifically increasing expression of an MHC class I molecule in a target cell, comprising: a) providing: i) the target cell, wherein the cell is infected with a pathogen selected from the group consisting of virus, bacteria, fungi, protozoa and metazoa; and ii) an expression vector encoding a heat shock protein; and b) introducing the expression vector into the target cell under conditions such that the heat shock protein is expressed and a transfected cell having increased expression of at least one MHC class I molecule is produced. In one preferred embodiment, the methods of the invention further comprise step c) detecting the increase in expression of the MHC class I molecule in the transfected cell compared to the target cell.

While it is not intended that the methods of the invention be limited to a particular heat shock protein, in one preferred embodiment, the heat shock protein is a member of a heat shock protein family selected from the group consisting of Hsp 27 family, Hsp 60 family, Hsp 70 family and Hsp 90 family.

Although it is not contemplated that the invention be restricted to a particular type of pathogen, in one preferred embodiment, the pathogen is a virus. In a yet more preferred embodiment, the virus is lymphocytic choriomeningitis virus.

Without intending to limit the invention's methods to a particular source of cell and/or a particular MHC class I molecule, one preferred embodiment contemplates that the target cell is murine and the MHC class I molecule detected is selected from the group consisting of murine H-2K and murine H-2D. In an alternative preferred embodiment, the target cell is human and the MHC class I molecule detected is selected from the group consisting of human HLA-A, human HLA-B and human HLA-C.

The invention further provides a method of increasing presentation of an antigen on a cell surface by an MHC class I molecule, comprising: a) providing: i) a target cell expressing the antigen and having a target cell surface; ii) an expression vector encoding a heat shock protein; b) introducing the expression vector into the target cell under conditions such that the heat shock protein is expressed and a transfected cell is produced having increased presentation of the antigen on the cell surface-by at least one MHC class I molecule; and c) detecting the increased level of presentation on the target cell surface.

While it is not intended that the methods of the invention be limited to a particular heat shock protein, in one preferred embodiment, the heat shock protein is a member of a heat shock protein family selected from the group consisting of Hsp 27 family, Hsp 60 family, Hsp 70 family and Hsp 90 family.

The methods of the invention are not limited to infecting the cell with any particular type or source of pathogen. In a preferred embodiment, the cell is infected with a pathogen selected from the group consisting of virus, bacteria, fungi, protozoa and metazoa. In a further preferred embodiment, the pathogen is a virus. In a yet more preferred embodiment, the virus is lymphocytic choriomeningitis virus.

It is contemplated that the invention not be limited to the type or source of target cell and/or the type or source of the MHC class I molecule. In one preferred embodiment, the target cell is murine and the MHC class I molecule detected in step c) is selected from the group consisting of murine H-2K and murine H-2D. In another preferred embodiment, the target cell is human and the MHC class I molecule detected in step c) is selected from the group consisting of human HLA-A, human HLA-B and human HLA-C.

The invention also provides a method of reducing radiation sensitivity of a target cell, comprising: a) providing: i) the target cell; and ii) an expression vector encoding a heat shock protein; b) introducing the expression vector into the target cell under conditions such that the heat shock protein is expressed and a transfected cell is produced; c) irradiating the transfected cell; and d) detecting a reduction in radiation sensitivity of the transfected cell compared to radiation sensitivity of the target cell. While it is not intended that the invention be limited to a particular type of cell, in a preferred embodiment, the target cell is a tumor cell.

Also provided by the invention is a method of increasing radiation sensitivity of a target cell, comprising: a) providing a target cell expressing at least one heat shock protein; b) treating the target cell to produce a treated cell, wherein expression of the at least one heat shock protein by the treated cell is reduced compared to the expression of the at least one heat shock protein by the target cell; and c) irradiating the treated cell to produce an irradiated cell, wherein the irradiated cell exhibits an increase in radiation sensitivity compared to radiation sensitivity of the target cell. The methods of the invention are not limited to a particular target cell. Nevertheless, in one preferred embodiment, the target cell is a normal cell. In a yet more preferred embodiment, the target cell is a stem cell.

BRIEF DESCRIPTION OF THE DRAWINGS

FIG. 1 shows the cDNA sequence (SEQ ID NO:1) of human hsp72.

FIGS. 9A through 9D show the nucleotide sequence of the coding region of the *Mycobacterium tuberculosis* hsp65 gene (SEQ ID NO:3).

FIG. 12(A) lower panel is a graph of α chain-specific band densities (in pixels/cm$^2$) normalized to the G3PDH internal control for each starting quantity of template used in FIG. 12(A) upper panel. Figure (B) shows flow cytometric analysis of permeabilized B16 and L929 transfectants using monoclonal antibody 28-8-6.

FIG. 14(A) is a graph of the cytolytic activity obtained from two separate experiments (upper and lower panel) in which the cytolytic activity of two separate allospecific CTL populations was measured against P815, P815.pSRαneo, P815.pSRαneo.Hsp65, LPS-activated H-2$^d$ splenocytes, B16.pSRαneo.Hsp65 and tumor EL4 targets.

FIGS. 16A–D show (A) the tumor incidence in syngeneic DBA/2 (H-2$^d$) mice immunized intraperitoneally with either saline (open squares), P815.pSRαneo cells (closed circles) or P815.pSRαneo.Hsp65 cells (open circles), followed by subcutaneous challenge with live, wild type P815, (B) tumor incidence in syngeneic C57BL/6 (H-2$^b$) mice immunized intraperitoneally with either saline (open squares), B16.pSRαneo cells (closed circles) or B16.pSRαneo.Hsp65 cells (open circles), followed by subcutaneous challenge with live, wild type B16, (C) tumor incidence in syngeneic C57BL/6 (H-2$^b$) mice immunized subcutaneously with either saline (open squares), B16.pSRαneo cells (closed circles) or B16.pSRαneo.Hsp65 cells (open circles), followed by subcutaneous challenge with live, wild type B16, and (D) growth kinetics of wild type challenge tumors in the mice depicted in FIG. 16(C).

FIGS. 21A–21C show the nucleic acid sequence (SEQ ID NO:5) of pSRα.

DEFINITIONS

Figure 2A:
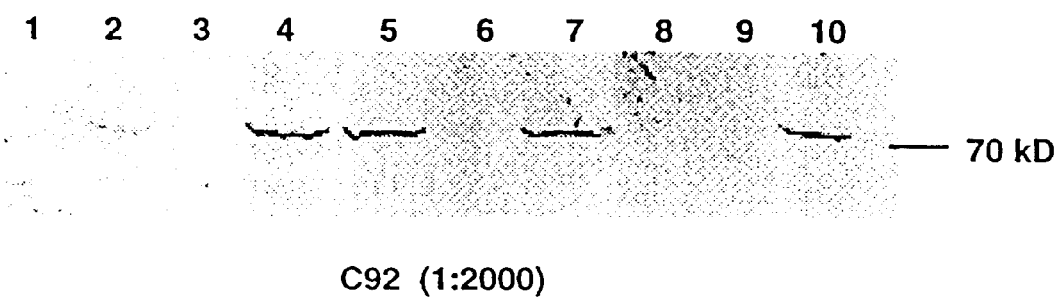
FIG. 2 shows (A) an immunoblot of cell lysates from B16.pSRαneo and B16.pSRαneo.hsp72 bulk line and sub-clones which was developed with monoclonal antibody C92, and (B) flow cytometric analysis of permeabilized B16 transfectants stained with isotype control (dotted gray lines) or C92 (solid black lines) monoclonal antibody.

To facilitate understanding of the invention, a number of terms are defined below.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals.

Transcriptional control signals in eukaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types [for review see Voss, et al., Trends Biochem. Sci., 11:287 (1986) and Maniatis, et al., Science 236:1237 (1987)]. For example, the SV40 early gene enhancer is very active in a wide variety of cell types from many mammalian species and has been widely used, for the expression of proteins in mammalian cells [Dijkema, et al., EMBO J. 4:761 (1985)]1. Two other examples of promoter/enhancer elements active in a broad range of mammalian cell types are those from the human elongation factor 1α gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous." An endogenous enhancer/promoter is one which is naturally linked with a given gene in the genome. An exogenous (i.e., heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site [Sambrook et al., Molecular Cloning: A Laboratory Manual, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation [Sambrook, supra, at 16.6–16.7]. This 237 bp fragment is contained within a 671 bp BamHI/PstI restriction fragment.

The term "transfection" refers to the introduction of foreign or heterologous DNA into a transfected cell Transfection can be "stable" or "transient." Stable transfection refers to the introduction and integration of foreign or heterologous DNA into the genome of the transfected cell. This is in contrast to transient transfection in which foreign or heterologous DNA which is introduced into the transfected cell does not become integrated in the transfected cell's genome.

The terms "selectable marker" or "selectable gene product" as used herein refer to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with TK$^-$ cell lines, the carbamoyl-phosphate synthetase-aspartate transcarbamoylase-dihydroorotase (CAD) gene which is used in conjunction with CAD-deficient cells and the mammalian hypoxanthine-guanine phosphoribosyl transferase (hprt) gene which is used in conjunction with HPRT$^-$ cell lines. A review of the use of selectable markers in mammalian cell lines is provided in Sambrook et al., supra at pp.16.9–16.15. It is noted that some selectable markers can be amplified and therefore can be used as amplifiable markers (e.g., the CAD gene).

The term "nucleic acid encoding" and "DNA sequence encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term, "heat shock protein" refers to a protein which binds to and stabilizes an otherwise unstable conformer of another protein and which facilitates the other protein's fate (e.g., folding, oligomeric assembly, transport to a particular subcellular compartment, or disposal by degradation) by controlled binding and release. Heat shock proteins are distinguished from the so-called folding catalysts in that heat shock proteins do not contain conformations specifying correct folding. Instead, they prevent incorrect interactions within and between non-native polypeptides, thus typically increasing the yields, but not the rate, of folding reactions. Heat shock proteins function under both stress- and non-stress conditions. For example, members of the Hsp 70 family function in de novo protein folding and membrane translocation, in the degradation of misfolded proteins as well as in regulatory processes [Hartl (1996) Nature 381:571–580]. Heat shock proteins are exemplified by, but not limited to, members of the Hsp27 family, Hsp60 family, Hsp70 family and Hsp 90 family. Heat shock proteins may be isolated from several organisms including bacteria, plants, yeast and higher eukaryotes (e.g., rodents and humans) and are found in all cellular compartments (e.g., cytosol, mitochondria, endoplastic reticulum and chloroplasts). Expression of heat shock proteins may be constitutive (e.g., eukaryotic Hsc73), inducible (e.g. eukaryotic Hsp72) or both constitutive and inducible (e.g., yeast SSA1-4).

The terms "specifically increasing expression" and "selectively increasing expression" when made in reference to an MHC class I molecule refer to the preferential increase in the level of expression of one or more MHC class I molecules (e.g., $K^b$, $D^b$, etc.) compared to the increase in the level of expression of a cell surface antigen other than an MHC class I molecule [e.g., MHC class II molecule, $\beta_2$-integrin (CD 18), H-CAM (CD 44)] in the same cell. An increase in the level of expression of an MHC class I molecule in a cell refers to a quantity of an MHC class I molecule in the cell which is greater than the quantity of the same MHC class I molecule in a corresponding control cell, preferably about two-fold greater than, more preferably about three-fold greater than, and most preferably at least about five-fold greater than, the quantity of the MHC class I molecule in a corresponding control cell. The quantity of an MHC class molecule may be determined by routine methods in the art, including Western blot analysis (as described herein) or Enzyme Linked Irmmunosorbent Assay (ELISA). In particular, the level of expression of a surface antigen may be determined by, for example, flow cytometric analysis as described infra (Examples 1, 3 and 5).

The term "MHC class I molecule" refers to a glycoprotein which is integral to the cell membrane. An MHC class I molecule is composed of two polypeptide chain, i.e., a transmembrane polypeptide of approximately Mr 45K which is noncovalently associated with a nonpolymorphic extracellular polypeptide, $\beta_2$-microglobulin. The transmembrane polypeptide is composed of an extracellular domain, a hydrophobic transmembrane domain and a cytoplasmic domain. One of the most important functions of MHC class I molecule is to present, on the cell surface, antigenic peptide fragments of intracellularly generated foreign protein antigens in a form that T cells can recognize. For example, an MHC class I molecule forms a complex with a viral antigen which is processed and degraded intracellularly to a short peptide fragment, and the formed complex is recognized as 'altered self' MHC and bound by a T cell receptor on a cytotoxic T cell as the first step in triggering lysis of a virus-infected cell. Similarly, as part of tumor surveillance, tumor-associated antigens also bind to MHC class I molecules on the membrane surface of neoplastic cells to form a complex which is recognized by cytotoxic lymphocytes, resulting in lysis of the neoplastic cell. Examples of MHC class I molecules include murine H-2K and H-2D, and human HLA-A, HLA-B and HLA-C.

The term "poorly immunogenic composition" refers to a poorly immunogenic cell or a poorly immunogenic antigen. A poorly immunogenic cell is a cell which expresses low levels of surface MHC class I molecules, and is thus defective in the presentation of endogenous antigens to cytotoxic T lymphocytes (CTL) as determined, for example, by the inability of these cells to induce a T cell response when administered to a syngeneic animal. A poorly immunogenic antigen is an antigen which is defective in inducing a T cell response when administered to an animal.

The term "increased level of presentation of an antigen on a cell surface by an MHC class I molecule" as used herein refers a quantity of the antigen which is physically associated (e.g., non-covalently) with a cell surface-bound MHC class I molecule and which is greater than a quantity of the antigen associated with the cell surface-bound MHC class I molecule in a corresponding control cell. An increase in the level of presentation of an antigen in a cell refers to a quantity of the antigen which is physically associated with a cell surface-bound MHC class I molecule which is greater than the quantity of the antigen which is physically associated with the cell surface-bound MHC class I molecule in a corresponding control cell, preferably about two-fold greater than, more preferably about three-fold greater than, and most preferably at least about five-fold greater than the quantity of the MHC class I molecule in a corresponding control cell. The level of presentation of an antigen by an MHC class I molecule may readily be determined by, for example, flow cytometric analysis as described herein.

The term "enhancing immunity" when made herein in reference to an animal's response to an antigen expressed by a cell refers to an increase in the level of the animal's immune response to the antigen. The level of an animal's immune response may be measured by, for example, isolating MHC class I-restricted cytotoxic T lymphocytes (CTL) from an animal harboring cells which express the antigen, contacting these CTL cells in vitro with cells expressing the antigen, and determining the cytolytic activity of the CTL cells (see, e.g., Examples 2, 6 and 7 herein). Alternatively, where the antigen is expressed by a tumor cell, the level of an animal's immune response to the antigen may be determined in vivo by measuring tumor incidence, the time period between administration of antigen-expressing tumor cells and the development of tumors, and rate of increase in tumor size (e.g., tumor diameter or volume) (see, e.g., Example 8 herein).

The term "radiation sensitivity" when made in reference to a cell means the number of cells refers to the reduction or cessation of the cell's ability to divide following exposure to a level of ionizing radiation which is above the level of background ionizing radiation. A reduction or cessation of a cell's ability to divide may be measured by, for example, determining the level of incorporation of $^3$H-thymidine into the cell (see, e.g., Example 9).

The terms "reduction in radiation sensitivity," and "increase in radiation sensitivity" when made in reference to a cell refer to the increase and reduction, respectively, in the proportion of cells which are capable of cell division following exposure to ionizing radiation which is above background ionizing radiation levels of as compared to the proportion of cells which are capable of cell division in corresponding control cells (e.g., in the absence of exposure to radiation). The proportion of cells which are capable of cell division may readily be determined by, for example, measuring the level of incorporation of $^3$H-thymidine into the cells (see, e.g., Example 9). Alternatively, where the cells are tumor cells, the proportion of cells which are capable of cell division may be determined by the rate of formation, or increase in size, of tumors in an animal following introduction of the tumor cells into the animal (see, e.g., Example 9).

DESCRIPTION OF THE INVENTION

The present invention provides methods for specifically increasing expression of MHC class I molecules in cells, and in particular, in poorly immunogenic tumor cells as well as in pathogen-infected cells (i.e., cells infected with bacteria, viruses, fungi, protozoa, and metazoa). Also provided by the present invention are methods for increasing presentation of endogenous antigens onto the cell surface by MHC class I molecules, as well as methods of increasing the immunity of an animal against an antigen. The methods of the instant invention are premised on the inventor finding that expression of a heat shock protein in a cell enhances the presentation of endogenous antigens by MHC class I molecules onto the cell surface in vitro, and further enhances the immunogenicity of the endogenous antigen in vivo.

The methods presented herein are useful in enhancing immune recognition of any cell infected with any pathogen including, for example, bacteria (e.g., *Mycobacterium tuberculosis*), viruses (e.g., human immunodeficiency viruses), fungi (e.g., *Candida albicans*), protozoa (e.g., *Plasmodium malariae*) and metazoa (e.g., *Taenia solium*). For example, evidence provided herein shows that the claimed invention enhances immune recognition by cytotoxic T cells of viral pathogens (e.g., LCMV) (see, e.g., FIG. 4) and recognition of tumor cells (e.g., melanoma cells and mastocytoma cells). Thus, the methods of the invention are useful for in vitro and in vivo screening of candidate immunogene therapeutic approaches in both non-human animals as well as in humans. The methods provided herein are also useful in enhancing the generation of antibodies to an otherwise poorly immunogenic antigen or poorly immunogenic cell.

The present invention further provides methods for selectively reducing or increasing the radiation sensitivity of a cell. These methods are based on the inventors' discovery that expression of heat shock proteins by a cell increases the cell's radiation resistance.

The description of the invention is divided into (A) Cell Biology of Antigen Processing And Presentation, (B) Heat Shock Proteins As Molecular Chaperones in Antigen Presentation, (C) Generation of Antibodies To Poorly Immunogenic Antigens, (D) Ex Vivo And In Vivo Methods Of Immunogene Therapy In Non-Human Animals And Human Patients, and (E) Selective Alteration Of Radiation Sensitivity.

A. Cell Biology of Antigen Processing and Presentation

Immune recognition of bacterial and viral pathogens, or of malignancy, is dependent upon a continual display of peptides in the context of surface MHC molecules by cells of the body (Germain (1994) Cell 76:287–299). Peptides presented in this manner can serve as ligands for antigen receptors on T lymphocytes, and represent a cross-section of essentially all of the proteins being synthesized within the host. Under normal circumstances, host T cells are presented with a peptide representation of "self"; a condition to which the immune system has been rendered tolerant during lymphocyte development (Weissman (1994) Cell 76:207–218). The damage of tissues, or the infection of tissues by a foreign pathogen, can alter this normal profile of peptides and result in the provision of ligands for T cell activation and in an ensuing immune response.

Therefore, cellular processes which are responsible for generating antigenic peptides and presenting them at the cell surface are crucial to effective immune surveillance and response. Higher vertebrates have evolved two specialized pathways of antigen processing and presentation in order to detect and respond to intracellular parasites, such as viruses, and to extracellular parasites, such as bacteria and fungi. These pathways (described below) differ with respect to the source of the, antigens chosen for processing, the type of MHC molecules that present the antigenic peptides, and the type of T cells which respond as a result.

1. Processing and Presentation of Exogenous Antigens

One of the first cellular responses during an assault by an extracellular pathogen is the recruitment of phagocytic cells, such as macrophages, to the site of infection. These macrophages can endocytose invading microbes and deliver them to specialized intracellular compartments termed lysosomes. Within the lysosomes, the foreign body is subjected to a highly oxidative and degradative environment. Peptides derived from the proteolytic degradation of exogenous microbes or particulates in the lysosome can then bind to membrane-linked MHC class II $\alpha$-$\beta$ heterodimers, which specifically localize to the lysosome after their synthesis and assembly in the endoplasmic reticulum (Goldberg and Rock (1992) Nature 357:375–379). MHC class II complexes then cycle between lysosomes and the plasma membrane, where peptides are presented to T cells (Germain and Hendrix (1991) Nature 353:134–139). Peptides presented in the context of MHC class II are recognized by a distinct subset of T cells which are phenotypically unique in their expression of the surface molecule CD4 (Killeen and Littman (1996) Curr. Top. in Microbiol. & Immunol. 205:89–106). These CD4$^+$ T cells function during an immune response to activate B cells for the production of antibody; and to activate other cell types for the enhanced killing of foreign microbes (Janevay and Bottomly (1994) Cell 76:275–286). Thus, exogenous antigens are processed and presented in a manner which tends to induce an immune response most tailored to combating an extracellular infection.

2. Processing and Presentation of Endogenous Antigens

In order for the immune system to detect foreign proteins in the cytosol, such as viral proteins synthesized within infected cells during viral replication, a pathway distinct from the exogenous pathway of antigen presentation must be utilized. Cytosolic, or endogenous, proteins are subject to constant turnover by proteolytic degradation. A proportion of this proteolysis is accomplished by a specialized, multiunit complex referred to as the proteasome (Goldberg and Rock (1992) Nature 357:375–379). Peptides generated by the proteasome are generally 8–9 amino acids in length, and are specifically transported from the cytosol into the endoplasmic reticulum (ER) by a transporter associated with antigen processing (TAP) (Shepherd et al. (1993) Cell 74:577–584; Neefjes et al. (1993) Science 261:769–771). Within the ER, peptides are quickly incorporated into complexes with MHC class I heavy chains and $\beta_2$ microglobulin ($\beta_2$M), and these stable, membrane-linked complexes are then secreted to the plasma membrane by conventional vesicular transport (Germain (1994) Cell 76:287–299). Peptides presented in the context of MHC class I are recognized by T cells which express the CD8 coreceptor. Upon activation, these CD8$^+$ T cells mature into cytolytic effectors capable of killing autologous cells which display antigenic peptides in the context of MHC class I (Mescher (1995) Immunological Rev. 146:177–210). Thus, the presentation of antigens through the endogenous pathway tends to induce immune responses that recognize and eliminate cells which harbor intracellular parasites.

3. Accessory Molecules in Antigen Presentation Pathways

Major histocompatibility molecules are involved in the direct recognition of antigenic peptides by T cells, and thus represent crucial elements of both the exogenous and endogenous pathways of antigen processing and presentation. The efficient presentation of peptide-MHC complexes at the cell surface, however, requires the function of several other molecules.

After cotranslational insertion into the ER, MHC class II exists as a heterotrimer of three transmembrane subunits; $\alpha$, $\beta$, and invariant chain (Ii) (Cresswell et al. (1990) Semin. Immunol. 2:273–280). Cells lacking Ii exhibit reduced assembly and surface expression of $\alpha$ and $\beta$ chains (Anderson and Miller (1992) Proc. Natl. Acad. Sci. USA 89:2282–2286), and those complexes that do reach the surface have not properly acquired peptide (Layet and Germain (1991) Proc. Natl. Acad. Sci. USA 88:2346–2350). Ii-negative cells thus do not present antigen efficiently to CD4$^+$ T cells (Bikoff (1992) J. Immunol. 149:1–8; Viville et al. (1993) Cell 72:635–648).

The $\alpha$ and $\beta$ subunits of MHC class II are relatively resistant to the proteolytic environment of the lysosome, whereas Ii is quickly degraded (Blum and Cresswell (1988) Proc. Natl. Acad. Sci. USA 85:3975–3979), leaving only the C-terminal end in association with $\alpha$ and $\beta$. In order for MHC class II molecules to acquire peptides derived from exogenously processed antigens, this class II-associated, invariant chain-derived peptide (CLIP) (Riberdy et al. (1992) Nature 360:474–477) must be dissociated from the peptide binding groove. This activity is apparently provided by another MHC-related molecule called DM. DM is a heterodimer of the two MHC-encoded gene products DMA and DMB, and is resident within the late endosomal/lysosomal compartment (Sanderson et al. (1994) Science 266:1566–9). Cell lines or transgenic mice which lack DM fail to dissociate CLIP from the MHC class II peptide binding groove, and thus are unable to present exogenously-derived peptides to CD4$^+$ T cells (Morris et al. (1994) Nature 368:551–554; Fling et al. (1994) Nature 368:554–558; Fung-Leung et al. (1996) Science 271:1278–1281).

As discussed above, the supply and transport of peptides which are capable of binding to MHC class I molecules depends on the activities of the proteasome and TAP, respectively. Cells which lack TAP do not transport peptides into the ER, and are unable to present endogenous peptides in the context of MHC class I to CD8$^+$ T cells due to an inability to assemble functional MHC class I-peptide complexes within the ER (Shepherd et al. (1993) Cell 74:577–584; Neefjes et al. (1993) Science 261:769–771).

Protease inhibitors which inactivate the proteasome with some degree of selectivity can abrogate the generation of some epitopes (Grant et al. (1995) J. Immunol. 155:3750–8; Rock et al. (1994) Cell 78:761–71). In addition to the components mentioned above, several members of a class of proteins called heat shock proteins, or "molecular chaperones", serve as accessory molecules in both the exogenous and endoganous pathways of antigen processing and presentation.

B. Heat Shock Proteins as Molecular Chaperones in Antigen Presentation

Heat shock proteins (Hsp) were originally described as a group of proteins whose synthesis was upregulated in response to hyperthermia or nutrient deprivation, and have since been shown to mediate protection from the cellular damage incurred during these and other extreme conditions (Ritossa (1962) Experientia. 18:571–573; Linquist (1986) Ann. Rev. Biochem. 55:1151–1191; Linquist and Craig (1988) Ann. Rev. Genet. 22:631–677; Ananthan et al. (1986) Science 232:522–524). These proteins are grouped into several families (Table 1), the members of which are present in every living organism, from bacteria to plants to mammals, and display a remarkable conservation of both structure and function across phylogeny (Gething and Sambrook (1992) Nature 355:33).

TABLE 1

Heat Shock Protein Families And Members

| Hsp27 family | | Hsp 60 family | | Hsp 70 family | |
|---|---|---|---|---|---|
| Member | Genbank Accession No. | Member | Genbank Accession No. | Member | Genbank Accession No. |
| Hsp27 (human) | AA523757 | Hsp60 (mouse) | X53584 | Hsp72 (human) | M15432 and M11717 |
| | | Hsp65 (M. paratub.) | X74518 | Hsp72 (mouse) | M76613 |
| | | GroE operon (E. coli) | X07850 | Hsp70B gene (human) | X51758 |
| | | TCP-1 zeta (mouse) | Z31557 | Hsp70 cognate (mouse) | X19141 |
| | | TCP-1 gamma (mouse) | Z31556 | Hsp70 cognate (human) | AA523625 |
| | | TCP-1 epsilon (mouse) | Z31555 | | |
| | | TCP-1 delta (mouse) | Z31554 | | |
| | | TCP-1 beta (mouse) | Z31553 | | |

In addition to the members listed in Table 1, the Hsp 27 family also includes the member Hsp27/28; the Hsp 60 family also includes the members Hsp65 (*M. tuberculosis*) and Hsp60 (human); the Hsp 70 family further includes the members GroEL (*E. coli*), Hsc58 (vertebrate), DnaK (*E. coli*), Hsc72, Hsp73, Prp73, Pbp72/74, Grp75, and Grp78; and the Hsp 90 family includes the members Hsp87/90, p88/IP90, Grp96, Hsp100, and Hsp108. Members of the Hsp 70 family which are derived from bacteria include DnaK, DnaJ and GrpE. In yeast, the eukaryotic homologs of bacterial members of the Hsp 70 family include SSA1–4, SSB1,2, SSC1, Kar2/BiP, YDJ1, SIS1, MDJ1, SCJ1 and MGE1, while their homologs in higher eukaryotes include Hsc73, and BiP.

Heat shock proteins exhibit a nearly universal capacity for binding extended polypeptide chains and they function to facilitate the proper folding, oligomerization, and trafficking of proteins within normal cells. During nutrient deprivation, or in the presence of stress-inducing agents such as heat, oxidative agents or protein synthesis inhibitors, heat shock proteins function to stabilize and re-organize denatured or damaged proteins and protein complexes within the cell (Welch et al. (1991) Curr. Top. Microbiol. and Immunol. 167:31). Because of these activities, heat shock proteins are often referred to as molecular chaperones (Laskey et al. (1978) Nature 275:416–420; Ellis (1990) Sem. in Cell Biol. 1:1; Ellis (1990) Science 250:954), and together they participate in a myriad of cellular processes.

1. Heat Shock Proteins as Integral Components of the Antigen Presentation Machinery Heat shock proteins facilitate the general trafficking and turnover of polypeptides within the nuclear, cytosolic and vesicular compartments, and thus may at least have a global role in the processing and presentation of antigenic peptides by antigen-presenting cells (APC). However, many chaperones have specialized, and in some cases, indispensable functions during many APC processes.

A potential role for heat shock proteins in antigen processing and presentation was first recognized through observations that heat shock could augment many APC functions. For example, heat-stressed B cells and macrophages exhibit an enhanced capacity to stimulate the proliferation of MHC class II-restricted T cell clones as compared to non-stressed APC (Rees et al. (1991) Immunology 74:386; Marlethoz et al. (1994) Int. Immunol. 6:925–930; Michalek et al. (1992) J. Immunol. 148:1016–1024). In these studies, the enhanced T cell stimulation correlated with the intracellular accumulation of Hsp70 proteins.

As shown in invariant chain- and TAP-mutant cell lines, the efficient egress of MHC class I and II molecules to the plasma membrane is dependent on the proper assembly of MHC-containing complexes ($\alpha$ and $\beta$ subunits of MHC class II with Ii, or MHC class I heavy chains with peptide and $\beta_2$M) within the ER. In fact, free or "empty," MHC subunits are actively retained within the ER until their incorporation into functional complexes. This selective trafficking is achieved through the activity of the ER resident heat shock proteins Grp94/gp96 (endoplasmin), p88/IP90 (calnexin) and Grp78 (BiP), which have been shown to associate with the unassembled subunits of both MHC class I and II within the ER (Wiech et al. (1992) Nature 358:169–170; Shaknovich et a. (1992) Mol. Cell. Biol. 12:5059–5068; Degen and Williams (1991) J. Cell Biol. 112:1099–1115; Gething et al. (1994) The biology of heat shock proteins and molecular chaperones, Cold Spring Harbor Laboratory Press, pp. 111–135). These chaperones thus function to retain free MHC subunits within the ER, protecting them from degradation and thus promoting the formation of ternary complexes (Jackson et al. (1994) Science 263:384; Rajagopalan et al. (1994) Science 263:387).

2. Heat Shock Proteins and Tumorigenicity

The first evidence that heat shock proteins may play a role in tumor immunogenicity arose over two decades ago through studies which utilized a biochemical approach to identify tumor antigens (Srivastava (1991) Curr. Op. Immunol. 3:654–658). Fractionated tumor cell lysates were tested for the capacity to immunize mice against challenge by various tumors, and proteins from those fractions which showed immunogenicity were further purified. In this way, several proteins were identified as major tumor antigens in various murine tumors of distinct origin. Three of these tumor antigens are now known to correspond to cytosolic Hsp90 (Ulrich et al. (1986) Proc. Natl. Acad. Sci. USA 83:6973), Grp96/endoplasmin (Srivastava and Maki (1991) Curr. Top. Microbiol. Immunol. 167:109–123) and cytosolic Hsp72/73 (Udono and Srivastava (1993) J. Exp. Med. 178:1391). The basis for the tumor-specific immunogenicity of these chaperones was initially perplexing. Heat shock proteins purified from distinct tumors elicited tumor-specific immunity while the same heat shock proteins derived from normal tissue exhibited no immunogenicity against tumors. Extensive sequence analysis of heat shock protein genes encoded by tumors and normal tissue, however, revealed no differences in the predicted primary protein structures (Srivastava and Maki (1991) Curr. Top. Microbiol. Immunol. 167:109–123). Therefore, tumor-specific heat shock protein polymorphisms were apparently not responsible for the differential immunogenicity of tumor-derived compared to tissue-derived chaperones. Also, the purified heat shock proteins administered in this model elicited very strong MHC class I-restricted, $CD8^+$ CTL responses, and these $CD8^+$ responses were not dependent on $CD4^+$ T cells (Udono et al. (1994) Proc. Natl. Acad. Sci. USA 91:3077–3081). This observation was unusual because the heat shock protein in this model represents exogenous antigen and should therefore be processed and presented via the exogenous pathway to MHC class II-restricted, $CD4^+$ T cells.

These studies have been extended to heat shock proteins purified from cells which express various foreign antigens in their cytosol. When used as an adjuvant-free vaccine in mice, heat shock protein preparations derived from cells expressing viral or bacterial antigens elicited strong antigen-specific $CD8^+$ CTL responses in vitro and in vivo (Srivastava et al. (1994) Immunogenetics 39:93; Arnold et al. (1995) J. Exp. Med. 182:885–889). Similar observations resulted from studies in which Hsp60 and Hsp70 homologs from *Mycobacterium tuberculosis* were used as peptide carriers in circumventing the need for adjuvants to greatly enhance immune responses to unrelated antigens (Lussow et al. (1991) Eur. J. Immunol. 21:2297; Barrios et al. (1992) Eur. J. Immunol. 22:1365–1372; Suzue and Young (1996) J. Immunol. 156:873–879).

These paradoxical results gave rise to the hypothesis that the heat shock proteins themselves were not the actual tumor antigens, but that they acted as carriers for antigenic peptides. This hypothesis is supported by the observation that both Gp96 and Hsp70 preparations derived from tumors lost antigenicity when low molecular weight oligopeptides were dissociated by the addition of ATP (Udono and Srivastava (1993) J. Exp. Med. 178:1391, Srivastava et al. (1994) Immunogenetics 39:93). It was therefore suggested that the priming of CTL responses by heat shock proteins in vivo may occur by a natural mechanism designed to deliver exogenous, peptide-laden heat shock proteins into the MHC class I pathway. The existence of such a mechanism is supported by the results of experiments in which mice were treated with the macrophage-poisoning agents silica or carageenan prior to immunization with antigenic preparations of tumor-derived chaperones (Suto and Srivastava (1995) Science 269:1585–1587). Whereas untreated mice immunized with tumor-derived heat shock protein preparations developed tumor-specific $CD8^+$ T cell responses, those mice depleted of macrophage function developed no anti-tumor $CD8^+$ T cell response. Therefore, it was the inventors' consideration that the transfer of antigenic peptides to host APC by chaperones in vivo may represent a biologically relevant step in the development of cytolytic T cell responses to malignant or virus-infected cells.

Heat shock proteins have also been implicated in the priming of immune responses to cancer in humans. Hsp70 has long been known to complex with activated mutants of the tumor suppressor protein p53 in transformed cells (Pinhasi-Kimhi et al. (1986) Nature 320:182), and this interaction appears to contribute to altered tumor suppressor activity of these mutants (Hainaut and Milner (1992) EMBO J. 11:3513; Finlay et al. (1988) Mol. Cell. Biol. 8:531). More recently, it has been shown that immune responses against human breast cancers are dependent upon the complex formation between Hsp70 and p53. In these studies, only patients whose tumors contained Hsp70–53 complexes also demonstrated serum antibodies specific for p53. Because antibody responses to non-repetitive protein antigens are T cell-dependent (Mosier et al. (1977) J. Immunol. 119:1874), the presence of anti-p53 antibodies in these patients suggests that Hsp70 was in some wary involved in the presentation of p53 epitopes to antigen-specific helper T cells; A separate study suggested that an Hsp60-related molecule expressed on the surface of a human Burkitt's lymphoma may serve as a recognition determinant for γδ T cells. Human Vγ9Vδ2 T cells proliferate in response to and lyse certain Burkitt's lymphoma cells in vitro (Fisch et al. (1990) J. Exp. Med. 171:1567). It was further shown that an Hsp60-related molecule was expressed on the surface of stimulatory, but not non-stimulatory tumor cells, and that an antiserum raised against mammalian Hsp58 blocked the proliferation of γδ T cells to these tumor cells (Fisch et al. (1990) Science 250:1269). Whether this molecule itself acts as an antigen, or whether it presents antigenic peptides remains unclear, however, a study in which the lytic response of γδ T cells to a different human Ourkitt's lymphoma was shown to be directed against a specific peptide presented in the context of Grp75, an Hsp70 family member expressed on the surface of these tumor cells (Kim et al. (1995) J. Immunol. 154:1614–1623).

Hsp70 expression was also shown to be associated with the immunogenicity of several rat colon carcinomas (Tamura et al. (1993) J. Immunol. 151:5516). In this study, the T cell-mediated rejection of various carcinoma clones was correlated with the capacity of these tumor cells to express inducible Hsp72 after heat shock in vitro, and reversion of immunogenic clones to a progressively growing phenotype after selection in vivo was associated with the loss of Hsp72 expression.

Further evidence for the capacity of heat shock proteins to enhance the immunological recognition of tumors in vivo comes from a study in which tumor cells were genetically modified to express mycobacterial Hsp65 (Lukacs et al. (1993) J. Exp. Med. 178:343–348). Hsp65-expressing tumor cells were no longer tumorigenic in syngeneic, immunologically intact mice, nor in T cell-deficient nude mice. Although challenge with these Hsp65-expressing tumor cells did not result in an established tumor, it did result in an tumor-specific T cell response capable of protecting mice from challenge with wild type tumor cells which did not express Hsp65. Elicited T cells were of the $CD4^+$ and $CD8^+$ subsets and both populations were capable of lysing both Hsp65-expressing and wild type tumor cells in vitro. Importantly, mice immunized with Hsp65-expressing tumor cells were protected from challenge with live wild type tumor cells to greater degree than mice immunized with the irradiated wild type tumor. This study shows that the transfection of a tumor cell with a heat shock protein augments its immunogenicity, and the immune response elicited by these cells is able to recognize and reject unmodified parent tumor cells.

C. Generation of Antibodies to Poorly Immunogenic Antigens

The methods of the invention are useful for the generation of antibodies (and in particular, monoclonal antibodies)

which are specific for otherwise poorly immunogenic antigens which are expressed by tumor cells and pathogen-infected cells. For example, in order to generate monoclonal antibodies to poorly immunogenic tumor cells from a non-human animal or from a human patient, the tumor tissue is harvested and tumor cells isolated using methods known in the art. For example, to isolate cells from glioblastomas, tumor tissue is incubated with 0.025% collagenase, 0.04% DNase and 0.05% Pronase with shaking for 30 min at 37° C. and a further 30 min at 4° C.; to isolate cells from hepatomas, tumor tissue is incubated with 1 mg/ml, collagenase type IV, 300 U/ml DNase type IV and 10 µg/ml gentamicin sulfate at 37° C. with shaking for 30 min.; to isolate cells from colon adenocarcinomas or from melanomas, tumor tissue is incubated with 1 mg/ml collagenase type V, 10 µg/ml hyaluronidase type V, 300 U/ml DNase type IV and 10 µg/ml gentamicin sulfate at 37° C. with shaking for 60 min.

The resulting cell suspensions are then filtered through a fine mesh and layered onto a Ficoll-hypaque density gradient medium (Sigma) and centrifuged at 400×g for 30 min at room temp. The cells at the interface are removed and cultured in the appropriate medium [e.g., RPMI 1640, DMEM, DMEM/F12 (all available from Sigma), etc.] containing 10% FCS and antibiotics if desired, resuspended into freezing medium for storage or used directly for gene transfection.

Tumor cells may be transfected with an expression vector which encodes a heat shock protein using a variety of means known in the art to be useful both for delivery in vivo and ex vivo, including (1) retroviral transduction, (2) recombinant adenoviral vectors, (3) targeted cationic liposomes, and (4) gene transfer using biolistics, as described in the following sections.

1. Retroviral Transduction

Retroviral vectors encoding heat shock proteins may be used for the expression of heat shock proteins in established or primary tumor cells. The transfer of heat shock proteins using retroviruses may be made more efficient by increasing the titer of the virus encoding the heat shock proteins and increasing the transduction efficiency. To increase the virus titer, the retroviral construct may be designed to include a selectable marker (e.g., neo gene), and cells harboring the retroviral construct are selected by growth in the presence of a suitable selective agent (e.g., G418) followed by expansion of clones producing the highest titers of virus. To improve the transduction efficiency, retrovirus are used in combination with liposomes or poly-L-ornithine or polylysine to enhance virus uptake.

Another way to improve gene transfer efficiency using retroviruses is to increase the targeting efficiency. Many tumor cells including glioblastomas and melanomas express excess levels of the transferrin receptor. Transferrin has been used to increase the transduction efficiency of adenovirus in combination with polylysine. Several recent reports demonstrated that replacing the SU (surface) domain of the env gene of a retrovirus can increase receptor-mediated transduction efficiency. The human transferrin gene is 2097 bp long and its insertion into the SU domain of the env gene of MLV vector may not produce a stable Env product. However, since earlier studies have suggested that the modified Env fusion protein requires the native Env for stable assembly and efficient entry, co-transfection of the transferrin-env fusion gene with the native env gene may be used to produce retrovirus particles bearing a mixture of wild type and recombinant Env. The gene transfer efficiency of the new vector may be examined by transducing tumor cells expressing high levels of transferrin receptor.

2. Recombinant Adenoviral Vectors

Recombinant adenoviruses can accommodate relatively large segments of foreign DNA (~7 kb), and have the advantage of a broad host cell range and high titer virus production. Adenoviruses have been used in vivo in rats to efficiently deliver genes to the liver and the pancreatic islets [reviewed in Becker et al. (1994) In *Protein Expression in Animal Cells*, Roth et al. eds.] and to the central nervous system [Davidson et al. (1993) Nature Genet. 3:219]. Rat livers have also been efficiently transduced ex vivo and then re-implanted [Shaked et al. (1994) Transplantation 57:1508].

The replication defective recombinant adenoviruses are preferably employed; these viruses contain a deletion of the key immediate early genes E1a and E1b. To generate and propagate recombinant viruses, a packaging cell line such as 293 cells which supply the E1a and E2a proteins in trans is employed. Recombinant adenoviruses are created by making use of intracellular recombination between a much larger plasmid encoding most of the viral genome and a small plasmid containing the gene of interest (i.e., a gene encoding a heat shock protein) flanked by regions of homology with the viral integration site. Standard methods may be used to construct the recombinant adenoviruses [Graham and Prevec (1991) Meth. Mol. Biol. 7:109–128; Becker et al. (1994) In *Protein Expression in Animal Cells*, Roth et al. eds.] Briefly, each plasmid is co-transfected together with pJM17 (Microbix Systems, Toronto) into sub-confluent monolayers of 293 cells (ATCC CRL 1573) using calcium phosphate precipitation and a glycerol shock. Initial recombinant viral stocks are titered on monolayers of 293 cells, and isolated single plaques are obtained and tested for heat shock protein expression using ELISA. Viral stocks are amplified and titered on 293 cells, and stored in aliquots at −70° C.; if necessary, stocks are concentrated by centrifugation on density gradients. To infect tumor cells with recombinant adenoviruses, freshly isolated tumor cells are mixed with adenoviral stocks in a minimal volume. Titers of stocks are typically $10^5$–$10^8$/ml. Medium is replaced after several hours and the cells are followed for expression of the recombinant adenoviral-encoded heat shock proteins and/or reporter genes.

A potential drawback of using an adenoviral delivery system is that the transduced cells may retain or express small quantities of adenoviral antigens on their surface. "Second generation" adenoviral vectors which contain deletions in the E2a gene are available and are associated with less inflammation in the recipient and a longer period of expression of the gene of interest [Yang et al., supra and Engelhardt et al. (1994) Proc. Natl. Acad. Sci. USA 91:6196]. If necessary, nucleic acid sequences encoding heat shock proteins are inserted into second generation adenoviral vectors. However, since the transduced tumor cells are lethally irradiated before injection into the recipient and since other manipulations are undertaken to induce the tumor cells to express cell surface MHC class I molecules, the expression of small quantities of adenoviral proteins (when first generation vectors are employed) may provide a desirable adjuvant effect. Furthermore, the recipient is subsequently boosted with retrovirally transduced tumor cells (which express the heat shock protein but not the adenoviral antigens). The recipient is monitored for tumor-specific immune responses at a secondary distant site where non-transduced tumor is implanted; the generation of such a response indicates that the desired tumor-specific immunity has been achieved.

3. Targeted Cationic Liposomes

Cationic liposomes have proven to be a safe and effective means for inducing the transient expression of DNA in target cells [Ledley (1995) Human Gene Ther. 6:1129; Felgner (1990) Adv. Drug Delivery Rev. 5:167; Felgner et al. (1987) Proc. Natl. Acad. Sci. USA 84:7413; and Smith et al. (1993) Biochim. Biophys. Acta 1154:327]. Clinical trials are underway using cationic liposomes to introduce the CFTR gene into the lungs of cystic fibrosis patients [Caplen et al. (1994) Gene Ther. 1:139 and Alton et al. (1993) Nature Genet. 5:135] or to introduce, by direct intra-tumor injection, the T cell costimulator B7-1 into malignant melanoma lesions in order to induce a cell-mediated immune response [Nabel et al. (1993) Proc. Natl. Acad. Sci. USA 90:11307].

Cationic liposomes (e.g., DOTAP/DOPE) and ligand-targeted cationic liposomes may be employed for the delivery of heat shock proteins to tumor cells. Ligand-targeted liposomes are made by covalently attaching ligands or antibodies to the surface of the cationic liposome. For example, when glioblastoma cells are to be targeted, transferrin is used as the ligand as glioblastoma cells express high levels of the transferrin receptor on their surface. When melanoma cells are to be targeted, internalizing receptors, monoclonal antibodies directed against melanoma-specific surface antigens (e.g., mAb HMSA5) may be employed as the ligand.

Plasmid DNA encoding heat shock proteins is formed into a complex with preformed cationic liposomes using standard methodology or alternatively the DNA is encapsulated into the liposome interior. The DNA-containing liposomes are then used to transfer the DNA to tumor cells in vivo by direct intra-tumor injection or in vitro (using freshly explanted tumor cells) followed by return of the transduced cells to the recipient (e.g., a human patient or non-human animal).

4. Gene Transfer Using Biolistics

Biolistics (microballistics) is a method of delivering DNA into cells by projection of DNA-coated particles into cells or tissues. DNA is coated onto the surface of gold or tungsten microparticles (~1–3 $\mu$m diameter) and these particles are accelerated to high velocity and are impacted onto the target cells. The particles burst through the cell membrane and lodge within the target cell. The cell membrane quickly reseals and the passenger DNA elutes off of the particle and is expressed. The biolistic method has been used to transfect mammalian cells [Williams et al. (1991) Proc. Natl. Acad. Sci. USA 88:2726; Tang et al. (1992) Nature 356:152; Sanford et al. (1993) Methods Enzymol. 217:483].

A hand-held biolistic apparatus (BioRad) is used to transfer DNA into tumor cells or isolated tumor fragments. This device uses compressed helium to drive a disc-shaped macroprojectile which carries on its surface microparticles (1–5 $\mu$m) of gold which have been coated with purified plasmid DNA (coprecipitated with spermine) (Williams et al., supra). This apparatus has been used to successfully transfect primary tissues.

Plasmid DNA encoding the heat shock proteins may be coated onto the surface of gold microparticles according to the manufacturer's instructions (BioRad) and the biolistic apparatus is used to transfer the DNA into freshly explanted tumor cells or directly into exposed tumors (e.g., metastatic nodules on the surface of the liver, melanoma lesions on the skin).

Regardless of the method of delivery of the expression vector into a cell, it is preferred, though not required, that the expression vector contain a selection marker (e.g., neo gene) to facilitate selection of transfected cells. Transfected cells are selected by growth in the presence of G418 (e.g., 200 $\mu$g/ml), followed by culture in growth medium containing reduced concentrations of G418 (e.g., 100 $\mu$g/ml) and growth to confluence. Expression of the heat shock protein is evaluated using, for example, immunoblot analysis or flow cytometry using monoclonal antibodies which are specific for the heat shock protein. It is preferred, though not necessary, that expression of the heat shock protein in the transfected tumor cells is both constitutive and stable. Constitutive expression refers to expression in the absence of a triggering event or condition, and can be achieved by the selection of a promoter which drives expression of the nucleic acid sequence encoding the heat shock protein. Examples of promoters which drive constitutive expression of a structural nucleic acid sequence which is operably linked to the promoter include the SR$\alpha$ promoter (used herein), CMV promoter, and HIV promoter.

In addition to screening for expression of the heat shock protein, cell-surface expression of MHC class I molecules is preferably also determined prior to further use of the transfected tumor cells. Cell-surface expression of MHC class I molecules may be determined using flow cytometry (described herein) using monoclonal antibodies which are specific for MHC class I antigens. Negative controls may include transfected tumor cells which are stained using an isotype control antibody, or tumor cells which are transfected with a vector lacking in the heat shock protein-encoding nucleic acid sequence. Selective cell-surface expression of MHC class I molecules may be established by comparing expression of MHC class I molecules to the expression of other cell surface proteins (e.g., MHC class II, $\beta$2 integrin (CD 18) and H-CAM (CD 44)) as described herein.

Transfected tumor cells are rendered replication incompetent by irradiation prior to their injection into an animal for the generation of monoclonal antibodies using various techniques familiar to those skilled in the art. Immunization with intact transfected tumor cells generally involves intraperitoneal injection of a dose of from $2 \times 10^6$ to $5 \times 10^7$ cells. Recipient animals may be boosted at intervals of 3–8 weeks, and fusion performed 2–4 days after the last boost.

Spleen cells from immunized animals are immortalized, commonly by fusion with a myeloma cell [see, Kohler and Milstein (1976) Eur. J. Immunol. 6:511–519; J. Goding (1986) In "Monoclonal Antibodies: Principles and Practice," Academic Press, pp 59–103]. Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted.

Spleen cells are fused with myeloma cells to generate hybridoma cell lines. One of skill in the art knows that the animals used for immunization as well as the animals used as recipients of the resulting hybridomas are preferably of the same genetic background in order to avoid rejection by the recipient animal of the hybridomas which display the histocompatibility antigens of the myeloma cells. Several myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10–15% fetal calf serum. Fusion of myeloma cells and spleen cells may be accomplished using polyethylene glycol (PEG) or by electrofusion using protocols which are routine in the art. Fused cells are distributed into 96-well plates followed by selection of fused cells by culture for 1–2 weeks in 0.1 ml DMEM containing 10–15% fetal calf serum and HAT. The supernatants are screened for antibody production using methods well known in the art. Hybridoma clones from wells containing cells which produce antibody are obtained, e.g., by limiting dilution. Cloned hybridoma cells ($4–5 \times 10^6$) are implanted intraperitoneally in recipient animals. Sera and ascites fluids are collected from animals after 10–14 days.

D. Ex Vivo and In Vivo Methods of Immunogene Therapy in Non-Human Animals and Human Patients The methods of the invention are useful for ex vivo and in vivo immunogene therapy of non-human animals as well as human patients harboring tumor cells or pathogen-infected cells. For example, ex vivo immunogene therapy of tumors involves harvesting the tumor tissue, isolating tumor cells, transfecting the isolated tumor cells with an expression vector encoding a heat shock protein, determining heat shock protein expression as well as selective cell surface expression of MHC class I molecules prior to irradiation to render the cells replication incompetent (e.g., cells are irradiated with 20,000 Rad in a $^{60}$Cobalt machine). For ex vivo immunogene therapy, non-human animals and human patients are given subcutaneous injections of approximately $2 \times 10^6$ irradiated autologous tumor cells modified to express one or more heat shock proteins. Injections are given on alternating lumbar flank regions which are marked immediately above the injection site with India ink to allow accurate localization later in the event that a local reaction is not apparent. Human patients receive 0.1 ml of vaccine injected SC at each site using a 1 ml syringe fitted with a 23 gauge needle. All vaccinations are prepared by resuspension of cells in sterile Ringer's lactate solution. Subsequent subcutaneous injections may be administered (e.g., a second and third vaccination 14 and 28 days, respectively after the first vaccination).

Subjects may be treated as outpatients and vital signs are monitored prior to immunization and every half hour for 3 hours after the subcutaneous injections. Patients are examined every hour for 3 hours for inflammation at the injection site and for evidence of rash, wheezing or edema. Provided there are no contraindications, subjects are discharged 3 hours after treatment. Should significant reactions occur, the patient is hospitalized for constant monitoring.

Patients are assessed in the clinic 3 days after vaccination and are evaluated weekly for 8 weeks and thereafter monthly for 4 months, every 3 months for 1 year and yearly thereafter. Patients are observed for any toxicities. Patients' immunologic reaction to immunogene therapy is monitored locally and systemically. Local immune response is monitored by symptoms and signs of delayed type hypersensitivity (DTH) responses at the vaccinatio sites. In addition, punch biopsies are performed at injection sites approximately 2 weeks after each vaccination (i.e., days 14, 28 and 42). These biopsies are compare to a biopsy taken from normal lumbar flank skin on day 1 (prior to initiation of therapy). Biopsies undergo standard pathologic examination for evidence of tumor cells and inflammation. In addition, immunohistochemical staining for CD45, CD4, C8 and NK cell markers is performed.

Systemic immune responses may be measured using two separate assays. Blood samples (20 ml each) are obtained on days 0, 7, 21, 35 and 49. These samples are used to isolate penipheri blood mononuclear cells (peripheral blood lymphocytes (PBLs) or peripheral blood mononuclear cells (PBMCs)) by centrifugation on a density (Hystopaque) gradient. The PBMC are then stimulated in vitro by co-incubation for 5 days with irradiated (20,00 Rad) autologous tumor cells. The stimulated PBMC are then used in the following two assays. First, a standard $^{51}$Chromium release cytotoxic T lymphocyte (CTL) assay s performed versus autologous tumor cells. Second, an ELISPOT assay for interferon-γ production after exposure to autologous tumor cells is performed [Zhang et al. (1996) Proc. Natl. Acad. Sci. USA 93:14720]. The $^{51}$Chromium release CTL assay is a standard assay for cell mediated immunity. This assay gives direct information concerning the ability of stimulated PBMC to kill tumor cells; however it has a relatively low sensitivity. To overcome this, the much more sensitive ELISPOT assay for interferon-γ production is also used. The ELISPOT assay determines the concentration of PBMC present that produce interferon-γ in response to exposure to autologous tumor cells. Since interferon-γ production is closely associated with $T_H1$ (cell mediated) immune responses, the number of PBMC producing interferon-γ in response to exposure to autologous tumor provides a measure of cell mediated immunity.

The clinical status of patients is followed by history, physical and laboratory parameters. In addition, appropriate diagnostic imaging tests (e.g., MRI scans with and without gadolinium enhancement) are obtained at 8 and 24 weeks, every 3 months for the following year, and yearly thereafter.

F. Alteration of Radiation Sensitivity

The methods provided herein are useful for selectively increasing or decreasing a cell's resistance to radiation. Data presented herein demonstrate that expression of heat shock proteins in a cell enhances the cell's resistance (i.e., reduce the cell's sensitivity) to ionizing radiation (Example 9).

Enhancing radiation resistance may be desirable, for example, where hematopoietic stem cells are isolated from the bone marrow of a patient suffering from cancer, are returned to the patient, and it is contemplated that further radiation therapy may be needed to control "break through" tumors. Using the methods of the invention, the radiation resistance of the stem cells may be increased prior to their return to the patient by transfecting the stem cells with a vector capable of expressing a heat shock protein so that subsequent irradiation treatment of the patient results in the preferential killing of cancerous cells rather than of the transfected stem cells. Target cells may be transfected with an expression vector ex vivo or in vivo as described above.

Conversely, it may be desirable to reduce the radiation resistance of, for example, tumor cells or pathogen-infected cells. Such reduction in radiation resistance may be accomplished by transfecting the target tumor cell or pathogen-infected cell with an expression vector which expresses an antisense molecule which is directed against the target cell's heat shock protein genes. Antisense sequences are used to turn off genes encoding a target cell's heat shock proteins by transfecting the target cell or tissue with expression vectors which express high levels of an antisense oligomer (e.g., 15–20 nucleotides) or larger fragment directed to the nucleic acid sequences encoding heat shock proteins. Such constructs can flood cells with untranslatable antisense sequences which inhibit expression of the heat shock protein either by inhibiting transcription of the heat shock protein gene (by preventing promoter binding to the upstream non-translated sequence) or inhibiting translation of a heat shock protein-encoding transcript (by preventing the ribosome from binding). Antisense sequences can be designed from various locations along the coding or control regions of the heat shock protein gene.

Alternatively, radiation resistance of a target cell may be achieved using an expression vector which expresses a ribosome which is capable of hybridizing to a complementary sequence in a substrate RNA encoded by the target cell's heat shock protein gene, and which cleaves the substrate RNA in a sequence specific manner at a substrate cleavage site. Target cells may be transfected ex vivo or in vivo with expression vectors which express either antisense sequences or ribosome sequences using the methods described above.

EXPERIMENTAL

The following examples serve to illustrate certain preferred embodiments and aspects of the invention and are not to be construed as limiting the scope thereof.

Example 1

Increased Level of MHC Class I Surface Antigens on Hsp72-Expressing Melanoma Cells In order to investigate whether molecular chaperone activity can influence the capacity of this cell line to present endogenous antigens in vitro, we generated stable clones of B16 which constitutively express the human heat-inducible 72 kD chaperone (FIGS. 2A and B) as follows.

A. Plasmids

The pSRαneo.hsp72 plasmid is a eukaryotic expression vector which encodes the human heat-inducible 72 kD chaperone under the transcriptional control of the strong constitutive promoter SRα (Takebe et al. (1988) Mol. Cell. Biol. 8:466). The pSRαneo.hsp72 plasmid was constructed by insertion of the 2600 bp BamH1 fragment from pG1HSP (kindly provided by Dr. William Welch), which contains the human inducible *hsp*72 cDNA sequence (SEQ ID NO:1, FIG. 1) (Hunt and Morimoto (1985) Proc. Natl. Acad. Sci. USA 82:6455) (GenBank Accession No. M11717), into the vector pSRαneo (Bukowski et al. (1995) J. Immunol. 154:998). The SRα promoter is an efficient mammalian cDNA expression system composed of the R-U5 segment of the HTLV-1 LTR fused to a heterologous SV40 early promoter-enhancer unit. Plasmids containing the SRα promoter (FIGS. 21A–21C) (SEQ ID NO:6) were constructed as previously described [Takebe et al. (1988) Mol. Cell. Biol. 8:466–472]. Briefly, a 267-bp fragment containing R and part of the U5 sequence of HTLV-1 LTR is inserted, from the exact 5' end of R (position 354) to the Sau3AI site in the U5 sequence (position 620), with a sense or antisense orientation, respectively, at the HindIII site immediately downstream of the SV40 early promoter. Transcription of cloned genes in vector pSRαneo is driven by the eukaryotic promoter SRα.

B. Generation of Stable T-Cell Transfectants Which Constitutively Express Hsp72

A number of tumor cell lines were transfected with pSRαneo or pSRαneo.hsp72. The B16 melanoma (H-2$^b$) (ATCC accession number CRLCRL-6322), the P815 mastocytoma (H-2$^d$) (ATCC accession number TIB-64) and the L929 (H-2$^k$) (ATCC accession number CCL1) fibroblastoid cell lines were provided by Dr. Joel Haynes. The RMA-S lymphoma (H-2$^b$) was provided by Dr. Peter Cresswell, and L929-D$^b$ was provided by Dr. Daniel Muller. All cell lines were cultured in RPMI supplemented with 10% FBS (Intergen, Purchase, NY, USA), 2 mM L-glutamine, 100 IU/ml of penicillin, 100 μg/ml streptomycin, 50 μg ciprofloxacin, and 25 mM HEPES. Approximately 5×10$^6$ tumor cells were transfected by electroporation (BioRad) at 300 V, 500 μF and 400 Ω with 10 μg of pSRαneo or pSRαneo.hsp72 DNA in serum-free RPMI. Transfectants were cultured in supplemented RPMI plus 0.8 mg/ml (active) G-418 (Geneticin, Life Technologies, Grand Island, N.Y., USA), and the resultant G-418-resistant colonies were picked and maintained in the presence of 0.3 mg/ml G-418 for approximately 2 weeks. Stable clones were then screened for the expression of Hsp72 by immunoblot and flow cytometric analysis as described in the following section.

C. SDS-PAGE and Immunoblot Protein Analysis

Proteins from tumor cell lysates prepared in Laemnimli buffer were resolved by SDS-PAGE and transferred to nitrocellulose membranes by semi-dry electrophoresis (Sambrook et al. (1991) Molecular Cloning: A Laboratory Manual. Cold Spring Harbor Press, New York). The membranes were incubated with varying dilutions of the monoclonal antibody C92 (StressGen, Victoria B. C., Canada) which recognizes the human and mouse heat-inducible Hsp72 gene products, but not the constitutive Hsc73. Immunoreactive proteins were visualized by incubation of the membranes with alkaline phosphatase-conjugated, affinity-purified goat anti-mouse serum (diluted 10,000-fold, Sigma, St. Louis, Mo., USA), followed by the addition of the chromogenic substrates NBT and BCIP (Boehringer Mannheim, Indianapolis, Ind., USA). Band densities (in pixels/cm$^2$) were quantified from digitized blot images using NIH Image 1.60b7 image analysis software.

The results of immunoblot analysis are shown in FIG. 2. The immunoblot revealed the presence of a single protein with an approximate molecular weight of 70 kD in lysates of B16 cells stably transfected with the plasmid pSRαneo.hsp72 (B16.pSRαneo.Hsp72; lanes 4, 5, 7 and 10; lanes 3, 6, 8 and 9 represent negative clones). No reactivity was observed in lysates of B16 clones transfected with the control plasmid pSRαneo (B16.pSRαneo; lane 1), or in lysates of B16 clones which stably express a heterologous heat shock protein, Hsp65 from *Mycobacterium tuberculosis* (not shown).

D. Flow Cytometric Analysis of Surface Intracellular Proteins

Adherent tumor, cell monolayers were harvested in PBS containing 1 mM EDTA, washed in supplemented RPMI. For cell surface staining, 2.5×10$^5$ cells were incubated with the appropriate monoclonal antibody (1 μg or 50 μl hybridoma supernatant) in a final volume of 100 μl for 30 minutes at 4° C. Cells were washed with cold PBS containing 2% calf serum and incubated with 1 μg FITC-conjugated goat anti-rat or -mouse antibody (Boehringer Mannheim, Indianapolis, Ind., USA) for 30 minutes at 4° C. In addition to monoclonal antibody C92, the monoclonal .antibodies used were M1/42 (ATCC TIB126) (Stallcup et al. (1981) J. Immunol. 127:923) which recognizes monotypic determinants of the murine H-2 (MHC class I), monoclonal antibody AF6-88.5 (Pharmingen, San Diego, Calif., USA) which is specific for K$^b$, and monoclonal antibody B22.249 (kindly provided by Dr. Alain Townsend) which recognizes a conformation-dependent determinant of the α2 domain of peptide-bound D$^b$ (Allen et al. (1984) Nature 309:279). The dilutions of M1/42, AF6-88.5 and B22.249 monoclonal antibodies used in this study represent a super-saturating concentration as determined by flow cytometric titration against the highly MHC class I-positive cell lines L929, P815 and EL4.

For intracellular staining, $2.5 \times 10^5$ cells were fixed with 1% formaldehyde in PBS and permeabilized in PBS containing 2% calf serum and 0.1% saponin. Permeabilized cells were incubated at room temperature for two hours with primary antibody (2 µg or a 5000-fold dilution of ascites), followed by a one hour incubation with FITC- or PE-conjugated goat-anti-mouse antibody or FITC-conjugated avidin (Becton-Dickinson, San Jose, Calif., USA). Fluorescence was measured using a Becton Dickinson FacScan™ flow cytometer. The dilutions of M1/42, AF6-88.5 and B22.249 monoclonal antibodies used in this study represent a super-saturating concentration as determined by flow cytometric titration against the highly MHC class I-positive cell lines L929, P815 and EL4. The results of flow cytometric analysis are shown in FIGS. 2B and 3, and Table 2.

Figure 2B:
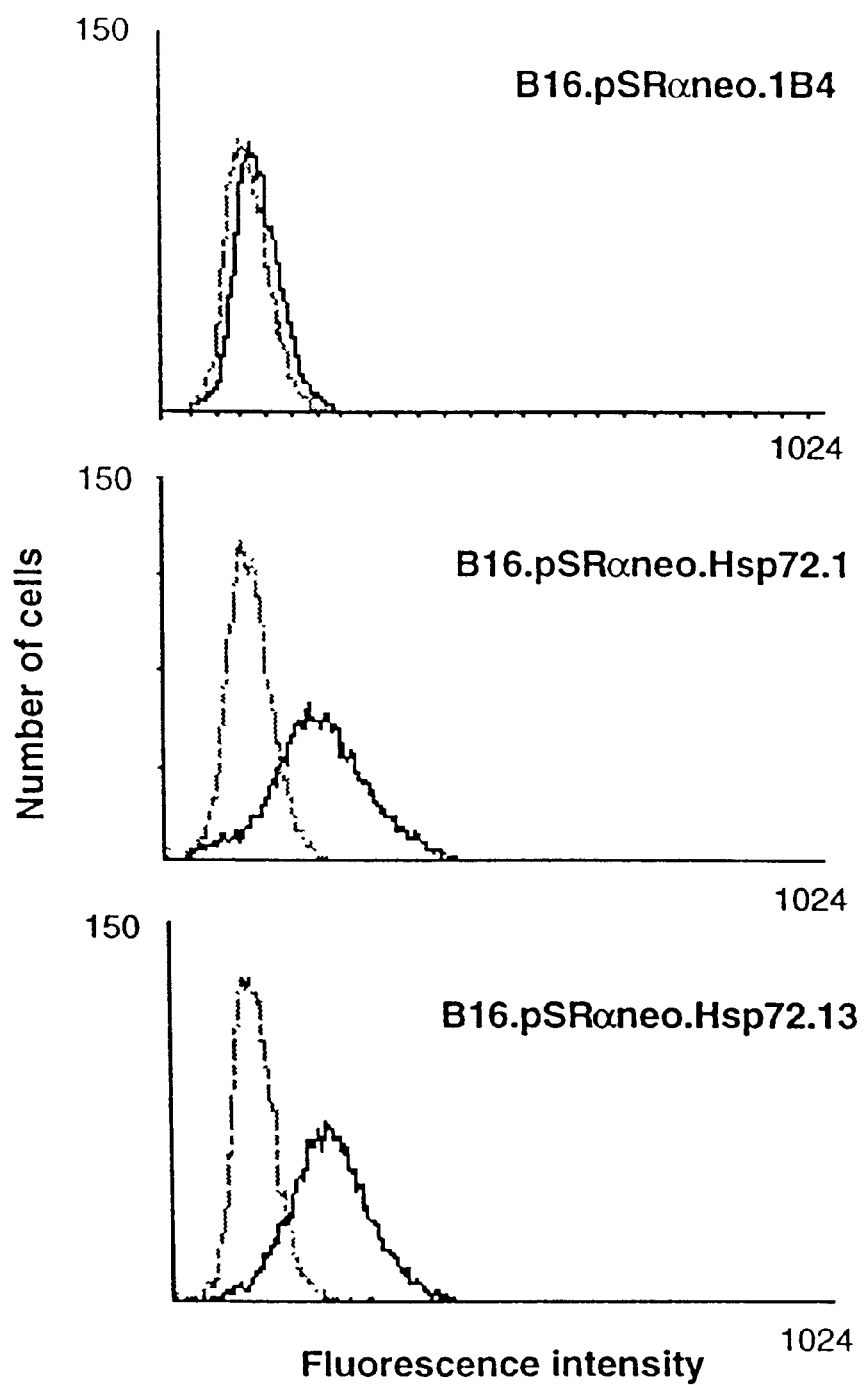

FIG. 2B showed that permeabilized B16 transfectants stained with isotype control (dotted gray lines) or C92 (solid black lines) monoclonal antibody revealed specific reactivity with B16.pSRαneo.Hsp72 cells (two representative clones, 1 and 13, are shown here), but not with B16.pSRαneo cells. This analysis also showed that essentially all of the cells in each B16.pSRαneo.Hsp72 clonal population express cytoplasmic Hsp72. No cell surface expression of Hsp72 could be detected by flow cytometry (not shown).

Figure 3A:
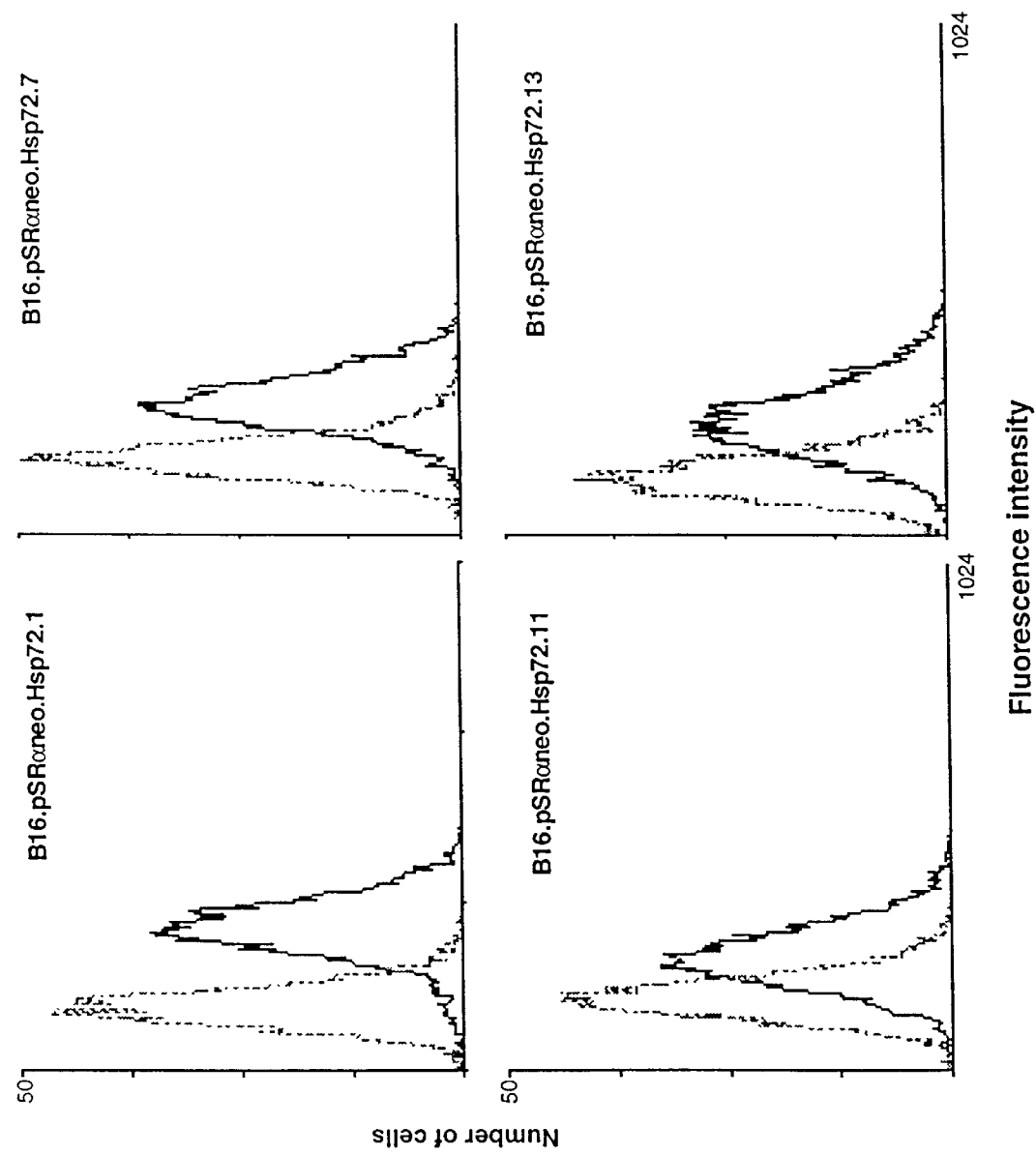
FIGS. 3A and 3B show flow cytometric analysis of B16, and various B16.pSRαneo clones using the monoclonal antibody M1/42 (A and B), AF6-88.5 (C) or B22.249 (D).
Figure 3B:
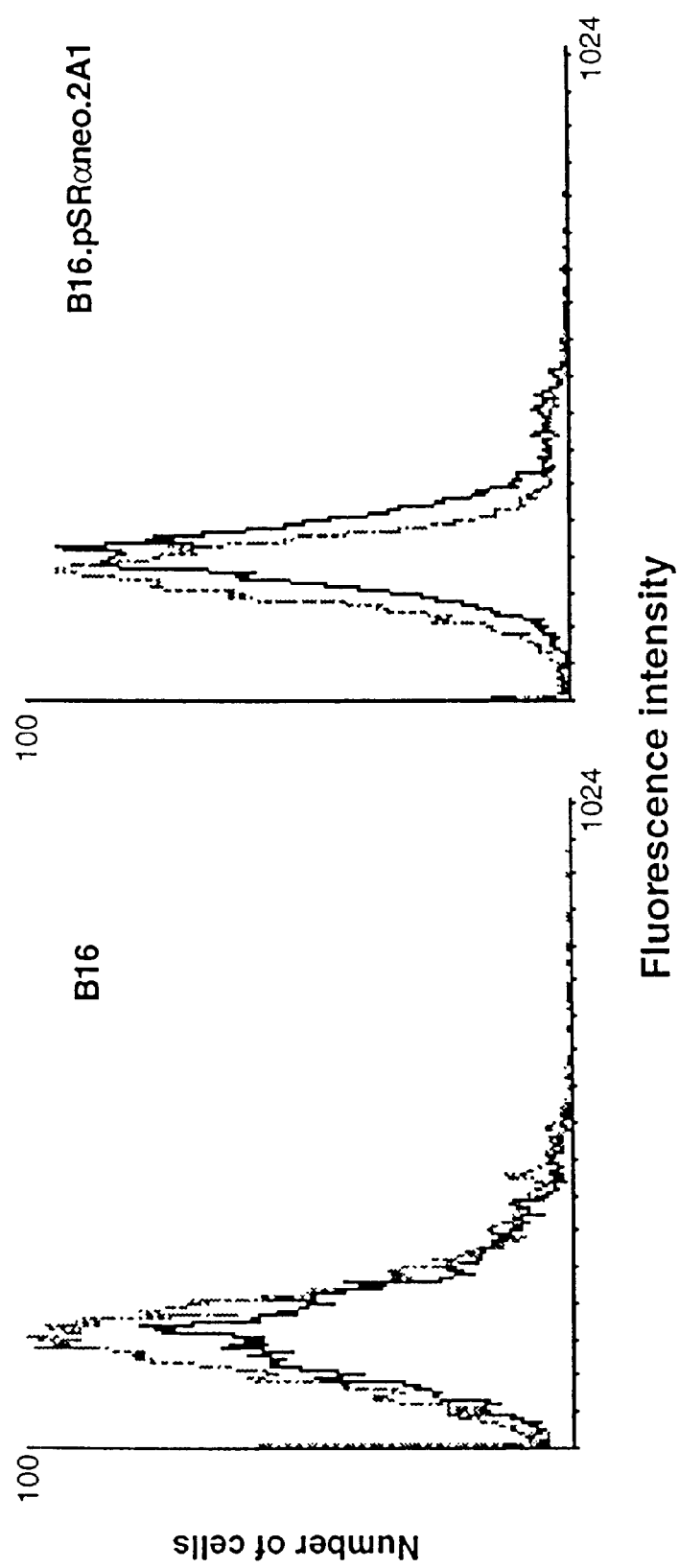
Figure 3C:
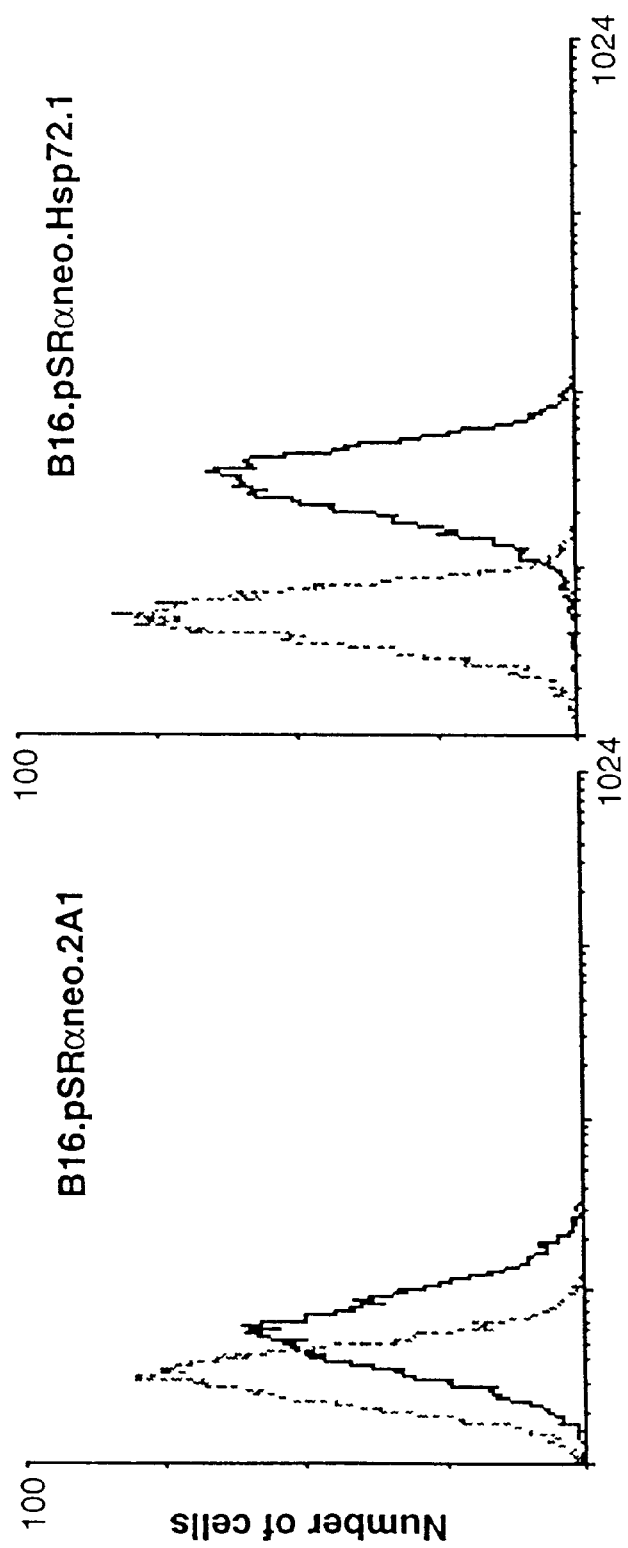
Figure 3D:
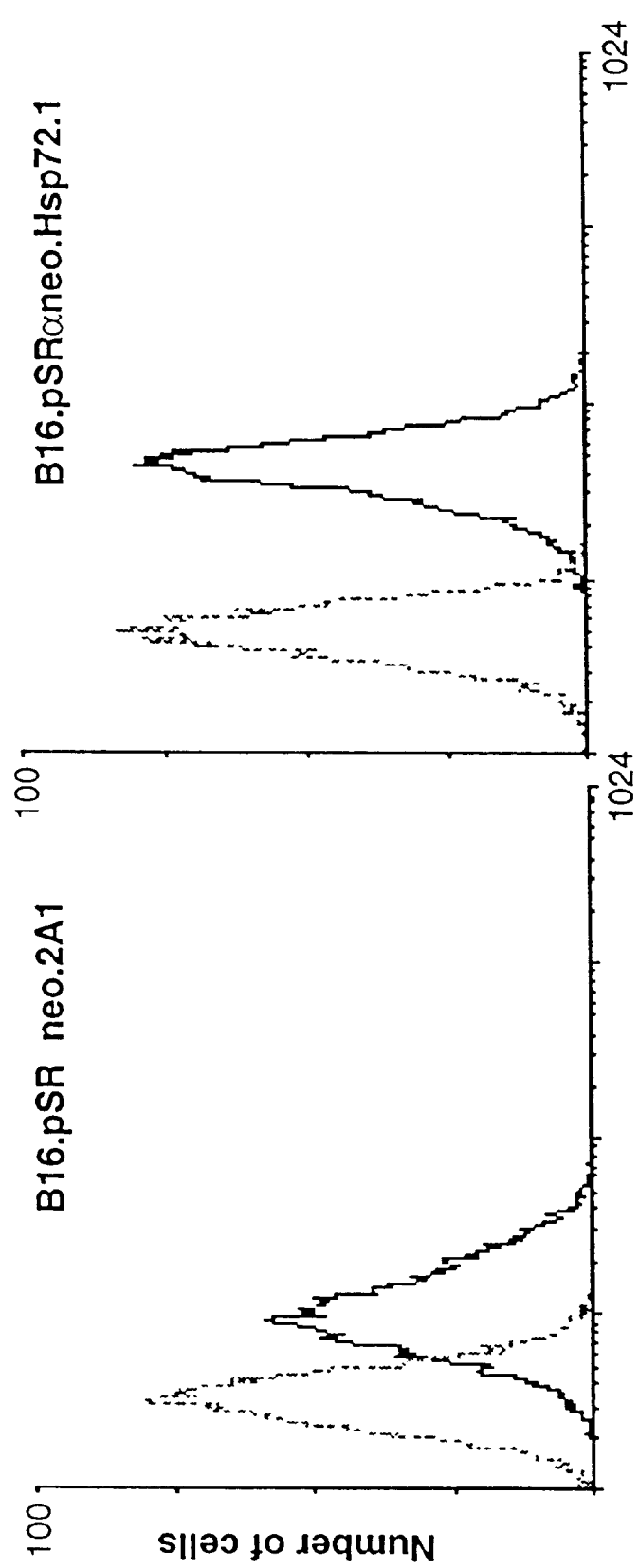

Using the monoclonal antibody M1/42, flow cytometric analysis of all B16.pSRαneo.Hsp72 clones (seven clones were examined; four representative clones, 1, 7, 11 and 13, are shown) revealed significant amounts of surface MHC class I antigen present (FIG. 3A), whereas the parent B16 melanoma line ($H-2^b$) and control B16.pSRαneo clones (clone 2A1 is shown here) displayed very little MHC class I surface antigen (FIG. 3B). Solid black lines show staining with specific antibody; dotted gray lines show staining with isotype control antibody. The mean fluorescence intensity (MFI) of B16.pSRαneo.Hsp72 cells stained with M1/42 was three- to four-fold greater than that of the parent B16 cells or the B16.pSRαneo cells stained with M1/42, or than that of B16.pSRαneo.Hsp72 cells stained with isotype control antibody. These results demonstrate that Hsp72-mediated effect is MHC class I-specific, because the surface expression of another related membrane protein, MHC class II, is not affected by Hsp72 expression (not shown).

Using the monoclonal antibodies AF6-88.5 and B22.249, B16.pSRαneo.Hsp72 expressed increased levels of both $K^b$ (FIG. 3C) and $D^b$ (FIG. 3D) as compared to B16.pSRαneo. Neither B16.pSRαneo.Hsp72 nor B16.pSRαneo clones expressed detectable levels of MHC class II (not shown).

Table 2 compares the expression of total MHC class I (M1/42), $K^b$ (AF6-88.5), and both total (28-14-8s) and stably folded (B22.249) $D^b$ antigens on control-transfected versus Hsp72-expressing B16 cells.

TABLE 2

Comparison of $D^b$, $K^b$, and total MHC class I levels on the surface of control-transfected B16, Hsp72-expressing B16 and L929 transfected with $D^b$

MFI

| | Monoclonal Antibody (specificity) | | | | |
|---|---|---|---|---|---|
| Clone | Isotype control | M1/42 (any K) | B22.249 ($D^{b*}$) | AF6-88.5 ($K^b$) | 28-14-8s ($D^{b**}$) |
| B16.pSRα ($H-2^b$) | 3.35 | 9.15 | 10.75 | 6.00 | 11.0 |
| B16.Hsp72 ($H-2^b$) | 4.82 | 41.8 | 42.4 | 27.3 | 51.2 |
| L929.pSRα ($H-2^k$) | 3.24 | 220.5 | 3.17 | 3.14 | 3.16 |
| L929.$D^b$ ($H-2^k/D^b$) | 2.41 | 132.9 | 131.7 | 2.41 | 186.9 |

*B22.249 recognizes only stably-folded $D^b$ molecules which exist as a complex with peptide and $\beta_2$M.
**28-14-8s recognizes both folded and unfolded $D^b$ molecules.

As shown in Table 2, Hsp72-expressing B16 cells exhibited a four- to five-fold increase in the mean fluorescence intensity (MFI) of antibodies specific for total MHC class I and for both $K^b$ and $D^b$ alleles as compared to control-transfected B16 cells. Similarly, Hsp72-expressing B16 cells exhibited a four-fold increase in the MFI of antibody specific for stably folded $D^b$ molecules. These data demonstrate that Hsp72 expression in B16 melanoma cells results in increased expression of surface MHC Class I molecules.

Example 2

Enhanced Presentation of Endogenous Antigens to MHC Class I-Restricted T Cells In Vitro To address whether this Hsp72-mediated increase in the surface expression MHC class I molecules on B16 melanoma cells corresponds to an enhanced capacity of these cells to present endogenous antigens, Hsp72-expressing B16 clones infected with lymphocytic choriomeningitis virus (LCMV) were used as targets for LCMV-specific, MHC class I-restricted cytotoxic T lymphocytes (CTL) in vitro. LCMV infection of mice with the $H-2^b$ haplotype induces a CTL response specific for an immunodominant epitope (GWTGSDGKTTWCSQ) (SEQ ID NO:2) derived from the viral GP gene product, as well as for several subdominant epitopes (Whitton et al. (1988) J. Virol. 62:687). The efficacy of these $H-2^b$-restricted CTL is largely dependent on the quantity of this peptide which is processed and presented in the context of the $D^b$ allele of MHC class I (Oldstone et al. (1988) J. Exp. Med. 168:559).

A. Generation of CTL Effector Populations

LCMV-specific CTL were generated as described (Salvato et al. (1991) J. Virol. 65:1863). Briefly, C57BL/6 or BALB/c mice (Harlan Sprague-Dawley (Madison, Wis.) between 6–10 weeks of age, were injected intraperitoneal with $2 \times 10^6$ pfu of the Armstrong 53b strain of LCMV. After seven days, the mice were sacrificed, the spleens were harvested, and the unfractionated splenocytes were used as effectors. Lymphokine-activated killer (LAK) were generated from allogeneic splenocytes by culture in supplemented RPMI with the addition of 1000 units/ml recombinant human IL-2 (Biological Response Modifiers Program, Washington DC, USA) for 3–5 days.

B. CTL Assay

Effectors were plated in 96-well plates at ratios of between 0 and 100 of effector cells:target cells with $^{51}$Crlabeled (100 μCi of Na$_2$[$^{51}$Cr]O$_4$ per 10$^6$ cells for one hour; ICN Biomedicals, Costa Mesa, Calif., USA) target cells, incubated at 37° C. for five hours, and the cell-free supernatants were harvested with glass fiber filter frames (Skatron Instruments, Sterling, Va., USA). LCMV-infected targets were infected with the Armstrong 53b strain at a multiplicity of one pfu/cell, two days prior to the assay. $^{51}$Cr emission was measured using a Minaxi Auto-Gamma 5000® counter (Packard, Downers Grove, Ill., USA) and % specific lysis was calculated as described (Malkovsky et al. (1982) Nature 300:652). The results are shown in FIG. 4.

Figure 4A:
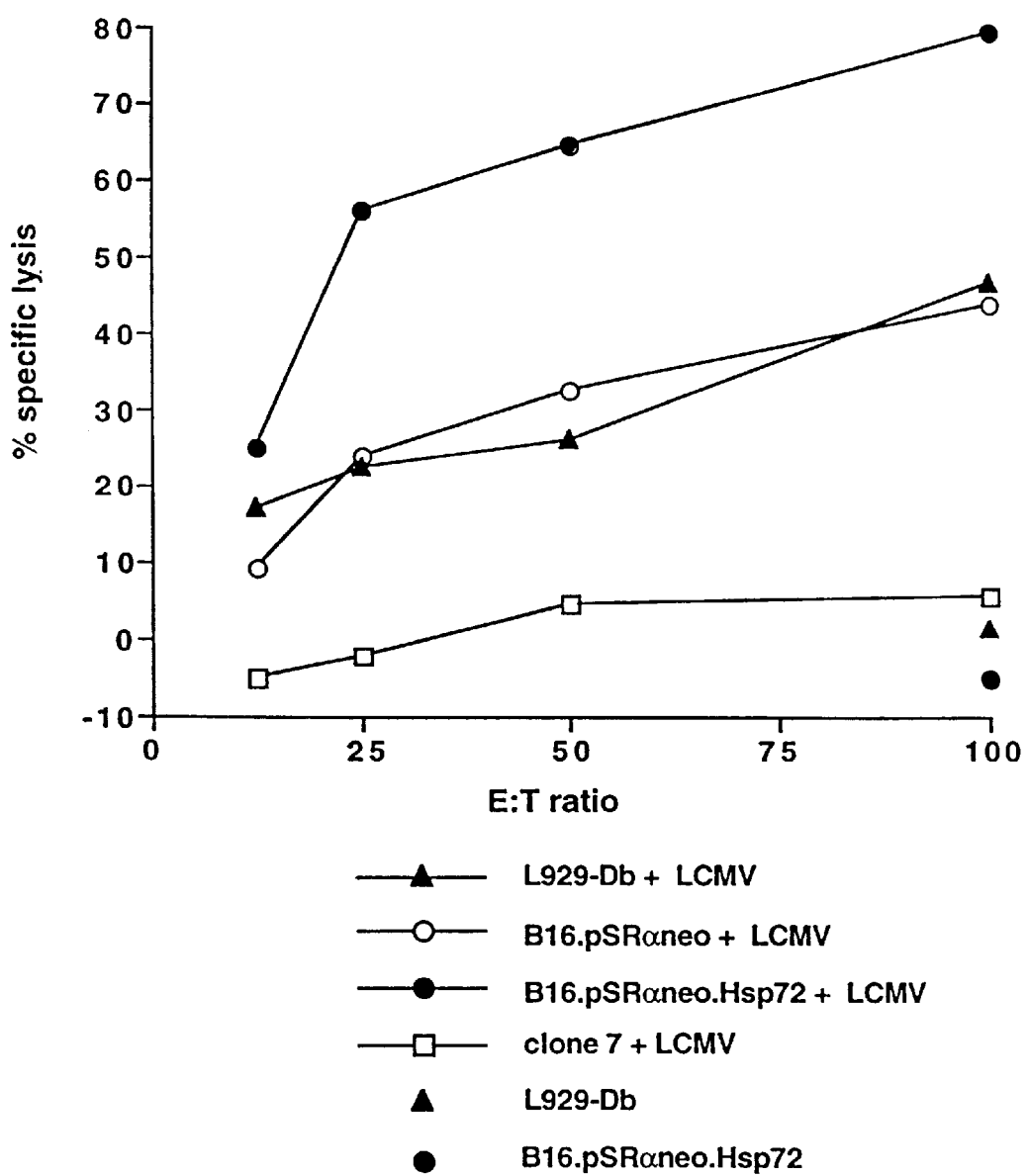
FIGS. 4(A) and (B) show the results of a LAK cell-mediated cytotoxicity assay in which the cytolytic activity of CTL populations from two separate LCMV-infected mice was measured against LCMV- or mock-infected targets.
Figure 4B:
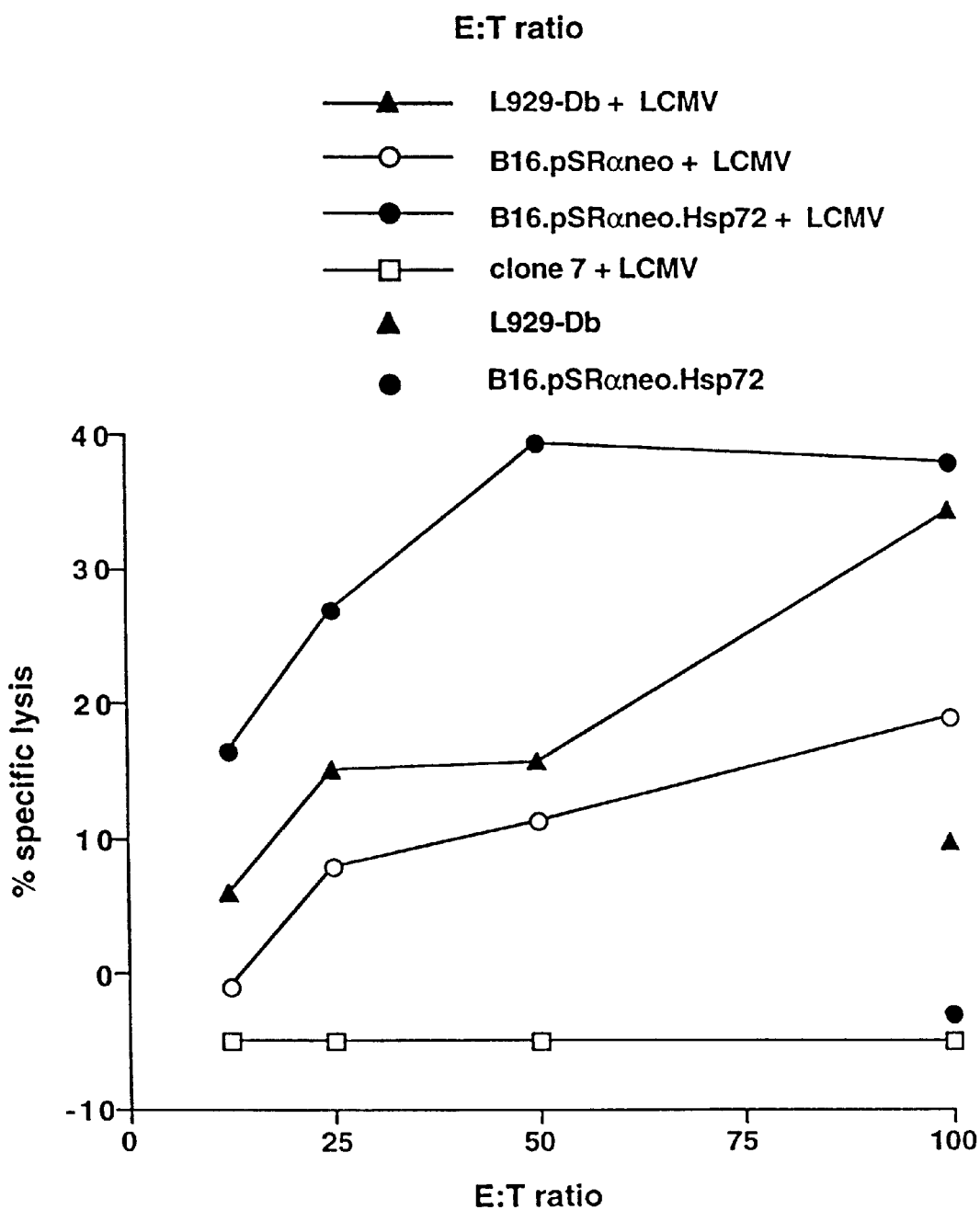

FIGS. 4A and 4B depict a representative cytotoxicity assay in which the cytolytic activity of CTL populations from two separate LCMV-infected mice was measured against LCMV- or mock-infected targets. L929-D$^b$ is a fibroblast cell line of C3H (H-2$^k$) origin which has been transfected with D$^b$, and, when infected with LCMV, is susceptible to D$^b$-restricted, LCMV-specific CTL lysis. LCMV-infected B16.pSRαneo.Hsp72 cells (closed circles) were consistently lysed by LCMV-specific CTL two- to four-fold more efficiently than LCMV-infected B16.pSRαneo.2A1 (open circles), or LCMV-infected L929-D$^b$ (closed triangles). Infected, MHC-mismatched clone 7 fibroblasts (H-2$^d$) (open squares) were not lysed, nor were mock-infected L929-D$^b$ (closed triangle at E:T of 100) or B16.pSRαneo.Hsp72 (closed circle at E:T of 100) clones. Separate experiments using B16.pSRαneo.Hsp72 clone 13 gave similar results (not shown). In addition, no lysis of LCMV-infected L929-D$^b$ or B16.pSRαneo.hsp72 cells was observed when CTL derived from LCMV-infected, allogeneic mice (BALB/c, H-2$^d$) were used as effectors (not shown). LCMV infection of targets was confirmed by immunoblot analysis using a GP-specific antiserum (not shown). Spontaneous release was <23%.

These results demonstrate that LCMV-infected, Hsp72-expressing B16 cells are recognized and killed by LCMV-specific CTL to a greater degree (approximately 1.8 fold) than control-transfected B16 cells, and that this killing is MHC-restricted (FIG. 4). In addition, LCMV-infected, Hsp72-expressing B16 cells also show greater than 5-fold susceptibility to killing by MHC I-restricted, LCMV-specific CTL as compared to control, LCMV-infected B16 clones. Lysis of Hsp72-expressing B16 cells exceeded that of L929 (H-2$^k$) cells transfected with D$^b$, even though L929-D$^b$ cells express three-fold more functionally conformed D$^b$ molecules on their surface than do Hsp72-expressing B16 cells (Table 2).

Figure 5:
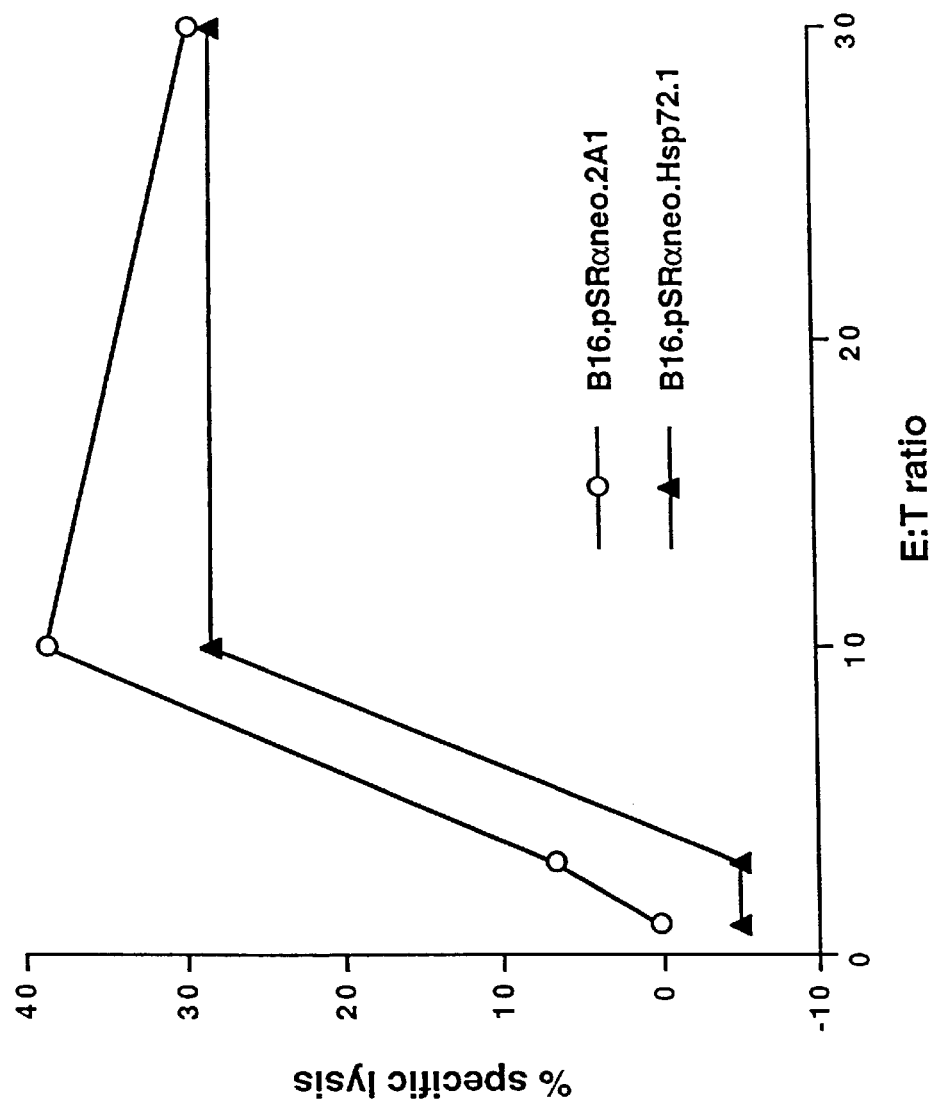
FIG. 5 shows the results of LAK cell-mediated cytotoxicity assay using B16.pSRαneo.2A1 or B16.pSRαneo.Hsp72.1 cells.

To investigate the possibility that the expression of Hsp72 merely made the cells more susceptible to lysis by non-specific cytotoxic effector mechanism, Hsp72-expressing clones were incubated with LAK cells. Data in FIG. 5 show that B16.pSRαneo.Hsp72 cells (closed triangles) were no more susceptible to non-specific, LAK cell-mediated cytotoxicity than are B16.pSRαneo control cells (open circles). Spontaneous release was <21%.

These data demonstrate that it is unlikely that the expression of Hsp72 merely made the cells more susceptible to lysis by cytotoxic effector mechanisms because non-specific, lymphokine-activated killer (LAK) cells lysed the Hsp72-expressing clones to the same degree as control clones (FIG. 5).

In addition, the enhanced reactivity of Hsp72-expressing B16 cells to MHC class I-specific antibodies, as well as the enhanced susceptibility of these cells to lysis by MHC class I-restricted CTL, suggests that the expression of Hsp72 results in a substantial increase in the amount of immunologically functional MHC class I molecules on the cell surface. Hsp72 expression enhanced the surface levels of both K$^b$ and D$^b$ MHC class I alleles, as well as the level of peptide-bound D$^b$ antigens. Hsp72-expressing B16 cells were lysed to a greater degree by MHC class I-restricted CTL than were L929-D$^b$ cells, even though L929-D$^b$ cells express substantially more functionally conformed D$^b$ molecules on their surface than do Hsp72-expressing B16 cells. These data suggest that the presentation of subdominant epitopes in the context of K$^b$ or D$^b$ contributes significantly to the enhanced lysis of Hsp72-expressing B16 cells by LCMV-specific CTL.

Example 3

TAP Mutation Prevents the Enhancement of MHC Class I Surface Expression and Endogenous Antigen Presentation by Hsp72

In order to further understand the mechanism by which Hsp72 influences MHC class I surface expression and endogenous antigen presentation, we employed the TAP-mutant cell line RMA-S (Ljunggren et al. (1989) J. Immunol. 142:2911), which is deficient in the supply of cytosolic peptides into the ER. This cell line lacks functional surface MHC class I expression and endogenous antigen presentation due to an inability to assemble MHC-peptide complexes (Townsend et al. (1989) Nature 340:443).

Figure 6A:
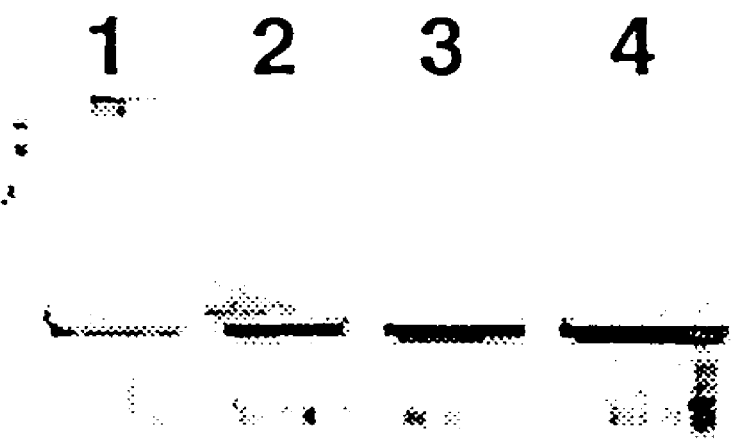
FIG. 6 shows (A) an immunoblot of lysates derived from stable RMA-S.pSRαneo (lane 1), RMA-S.pSRαneo.Hsp72 (lanes 2 and 3) and B16.pSRαneo.Hsp72.1 (lane 4) clones using the monoclonal antibody C92, and (B) pPixel densitometric quantitation of the bands in lanes 1–4 in the immundblot of (A).
Figure 6B:
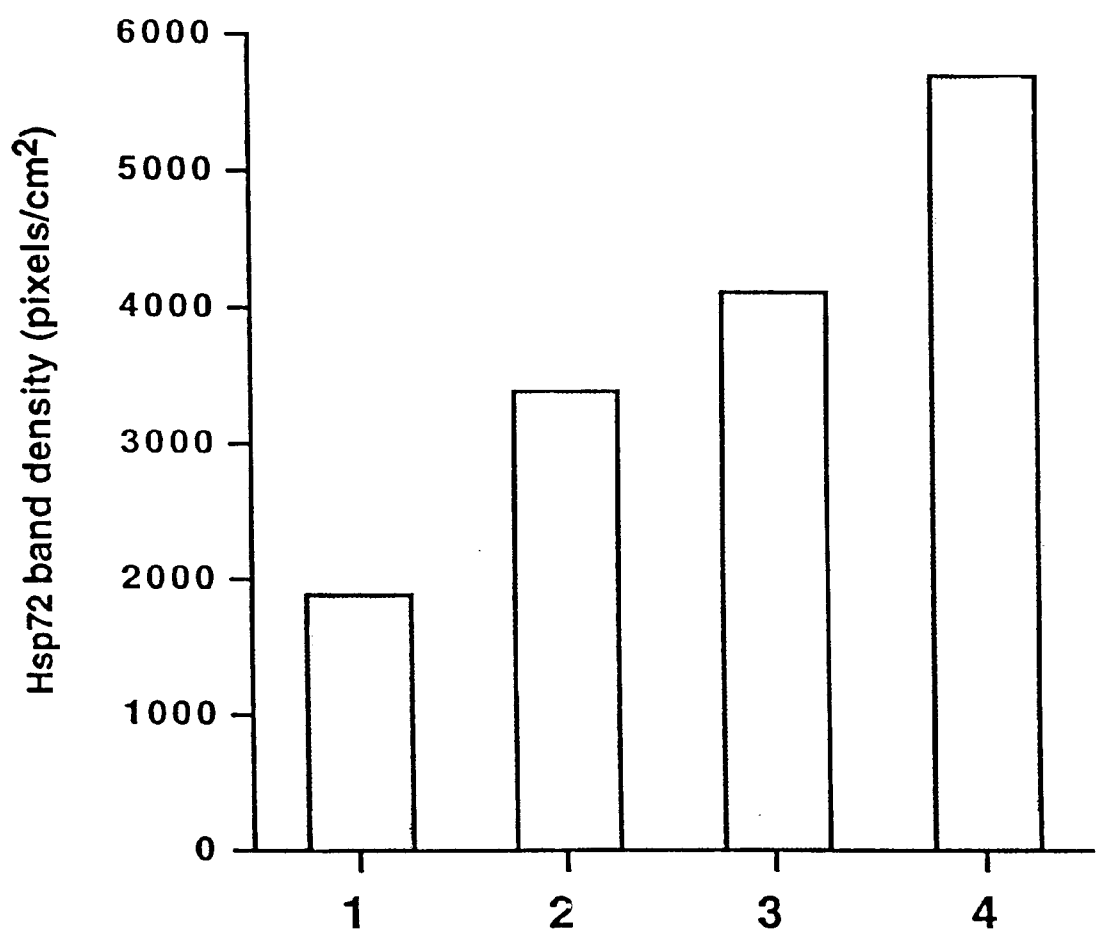

Overexpression of Hsp72 by RMA-S melanoma cells stably transfected with pSRαneo.hsp72 was measured by using the monoclonal antibody C92. The results of immunoblotting are shown in FIG. 6A while pixel densitometric quantitation is shown in FIG. 6B. FIG. 6A shows immunoblot analysis of lysates derived from stable RMA-S.pSRαneo (lane 1), RMA-S.pSRαneo.Hsp72 (lanes 2 and 3) and B16.pSRαneo.Hsp72.1 (lane 4) clones. 2 μg of total protein was loaded in each lane. FIG. 6B shows densitometric quantitation of the bands in lanes 1–4 in (A) using NIH Image processing software. Similar results were obtained when the levels of Hsp72 was normalized against the levels of Hsc73 in each lysate (data not shown).

The results show that stable transfectants of RMA-S which constitutively express Hsp72 at levels comparable to those exhibited by Hsp72-transfected B16 clones (FIG. 6) did not exhibit an increase in the amount of functionally conformed MHC class I molecules on the cell surface compared to control-transfectants (Table 3).

TABLE 3

Effect of TAP mutation on Hsp72-mediated MHC class I surface upregulation: levels of stably folded D$^b$ antigens or K$^b$ antigens on the surface of control-transfected v. Hsp72-transfected RMA-S clones

| | Relative MFI* | |
| --- | --- | --- |
| RMA-S clone | D$^b$ | K$^b$ |
| pSRαneo.1A1 | 3.86 | 3.33 |
| pDTαneo.1A3 | 4.02 | 2.85 |
| pSRαneo.Hsp72.2B3 | 3.08 | n.d. |
| pSRαneo.Hsp72.2C2 | 2.78 | 2.24 |
| pSRαneo.Hsp72.2C3 | 3.21 | 2.92 |
| pSRαneo.Hsp72.3A4 | 3.72 | 1.90 |

*Expressed as the fold-increase of B22.249 (D$^b$) or AF6-88.5 (K$^b$) staining over that of the isotype control.
n.d. = not determined.

Figure 7:
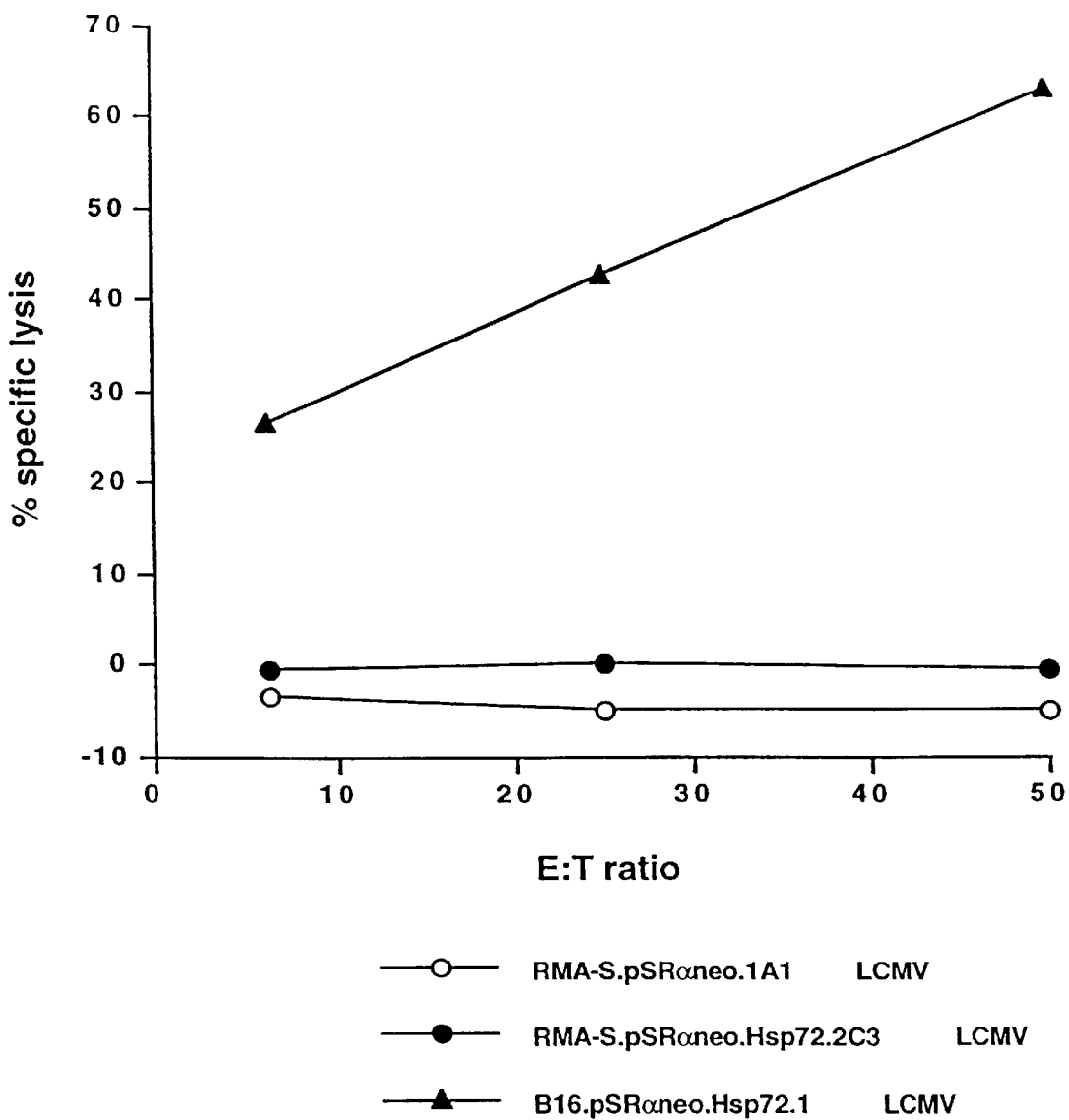
FIG. 7 shows the results of LAK cell-mediated cytotoxicity assay in a mouse infected with LCMV together with RMA-S.pSRαneo.1A1 (open circles), RMA-S.pSRαneo.Hsp72.2C3 (filled circles), or B16.pSRαneo.Hsp72.1 (filled triangles).

In order to determine the effect of TAP mutation on the capacity of Hsp72 to enhance endogenous antigen presentation, the susceptibility of LCMV-infected control-transfected RMA-S (open circles), Hsp72-expressing RMA-S (closed circles), and Hsp72-expressing B16 cells to lysis by LCMV-specific CTL was assessed, as shown in FIG. 7. FIG. 7 shows that RMA-S cells expressing Hsp72 were unable to present endogenous antigens to MHC class I-restricted T cells. Neither uninfected, nor infected, haplotype-mismatched targets were lysed by LCMV-specific CTL in this experiment (data not shown).

Example 4

Enhanced Immunogenicity of Hsp72 Chaperone-Expressing Melanoma Cells In Vivo

Wild type B16 melanoma cells are unable to elicit a specific immune response when injected into mice. To address whether Hsp72-expressing B16 cells could elicit an immune response in vivo, we assessed the capacity of Hsp72-expressing B16 cells to immunize mice against a subsequent challenge with wild type B16 cells, which do not express Hsp72 constitutively.

For the in vivo immunization and tumor rejection assay, B16 transfectants to be used as an immmunogen were growth-inhibited by treatment with mitomycin C (25 μg/ml for 3 hours; Boehringer Mannheim), harvested in PBS containing 1 mM EDTA, and washed in PBS. Mitomycin C-treated tumor cell suspensions were then γ-irradiated (5000 rad), washed in PBS, and resuspended at $5 \times 10^6$ cells per 0.2 ml PBS. At days 0 and 10 of each experiment, C57BL/6 mice (4–5 per group) were injected either intraperitoneal or subcutaneously with 0.2 ml PBS, or with inactivated tumor cell suspensions ($5 \times 10^6$ cells) in 0.2 ml PBS. Immunized mice were then challenged on day 20 by subcutaneous injection of $2 \times 10^4$ wild type B16 tumor cells (viability >98%) suspended in 0.1 ml PBS. The 50% tumorigenic dose of the B16 melanoma cells used in these studies was determined to be approximately $2 \times 10^3$ cells. Doses of $5 \times 10^3$, $10^4$ and $2 \times 10^4$ cells lead to progressively growing tumors in 100% of naive mice challenged subcutaneously. Incidence of the challenge tumor was assessed by palpation of the challenged flank, and was scored as positive on the day that the established tumor reached 25 mm² as measured by tissue calipers. Mice were sacrificed before challenge tumors reached 500 mm², or if mice developed ascites from the immunizing tumor cell dose. The results are shown in FIG. 8.

Figure 8:
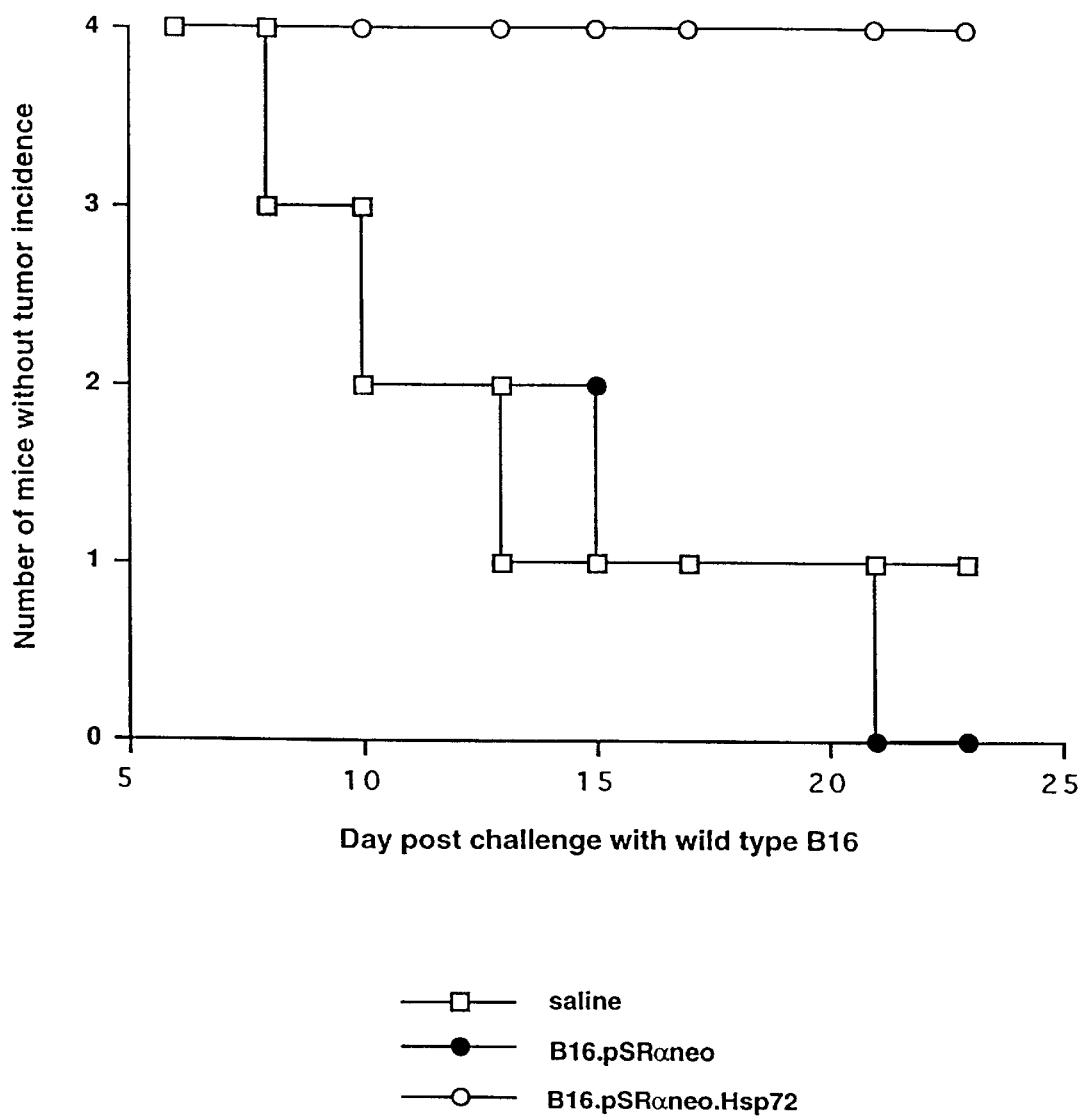
FIG. 8 shows the tumor incidence in syngeneic C57BL/6 (H-2$^b$) mice immunized intraperitoneally with either saline (open squares), B16.pSRαneo cells (closed circles) or B16.pSRαneo.Hsp72 cells (open circles), followed by subcutaneous challenge with live, wild type B16.
Figure 10A:
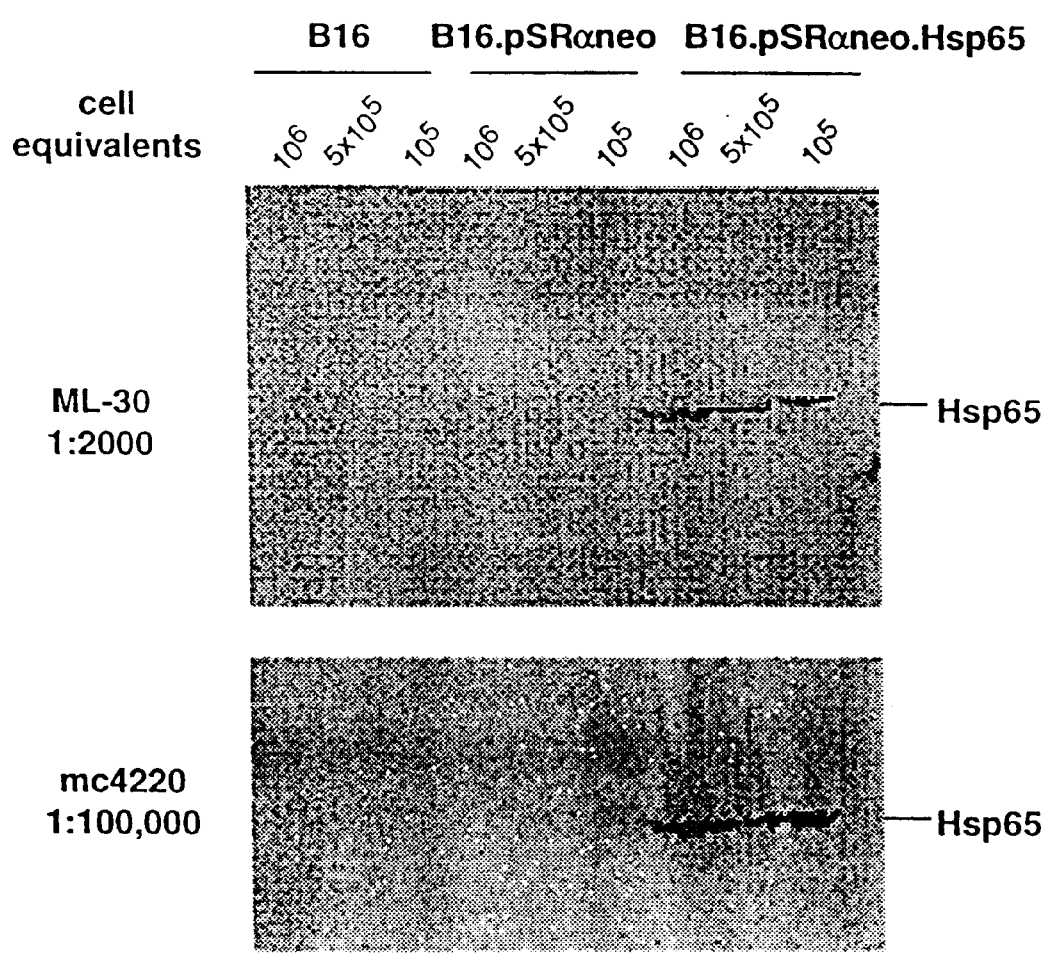
FIGS. 10A and 10B show an immunoblot of extracts from B16, B16.pSRαneo, and B16.pSRαneo.Hsp65 cells using the monoclonal antibody ML-30 and mc4220 (A), an immunoblot of extracts from P815.pSRαneo.Hsp65 clones using mc4220 (B), flow cytometric analysis of permeabilized B16 transfectants (C) or (D) p815 transfectants.
Figure 10B:
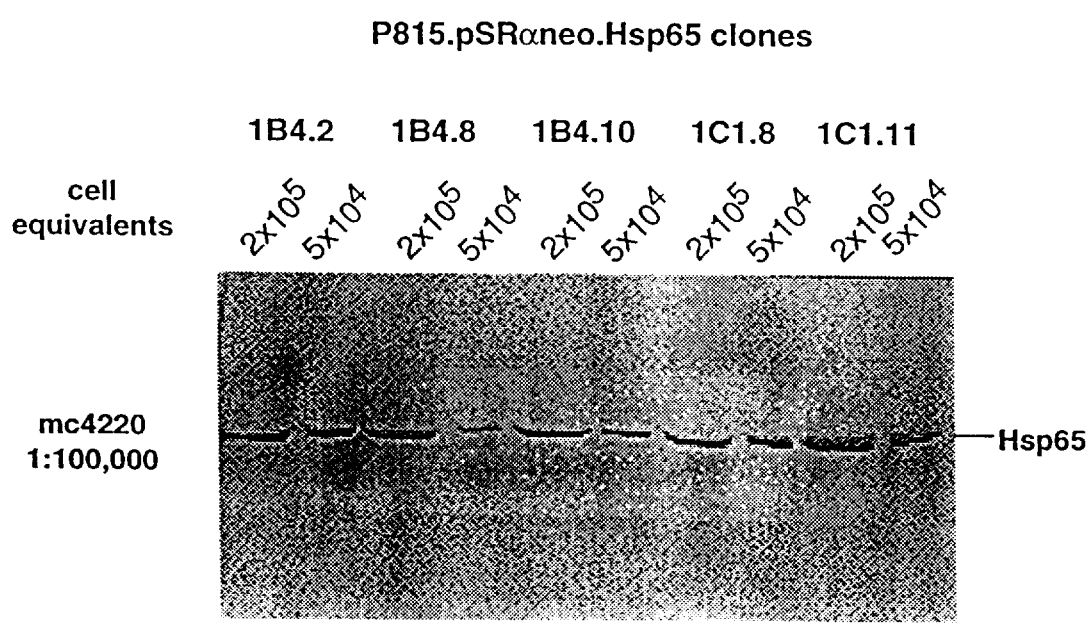
Figure 10C:
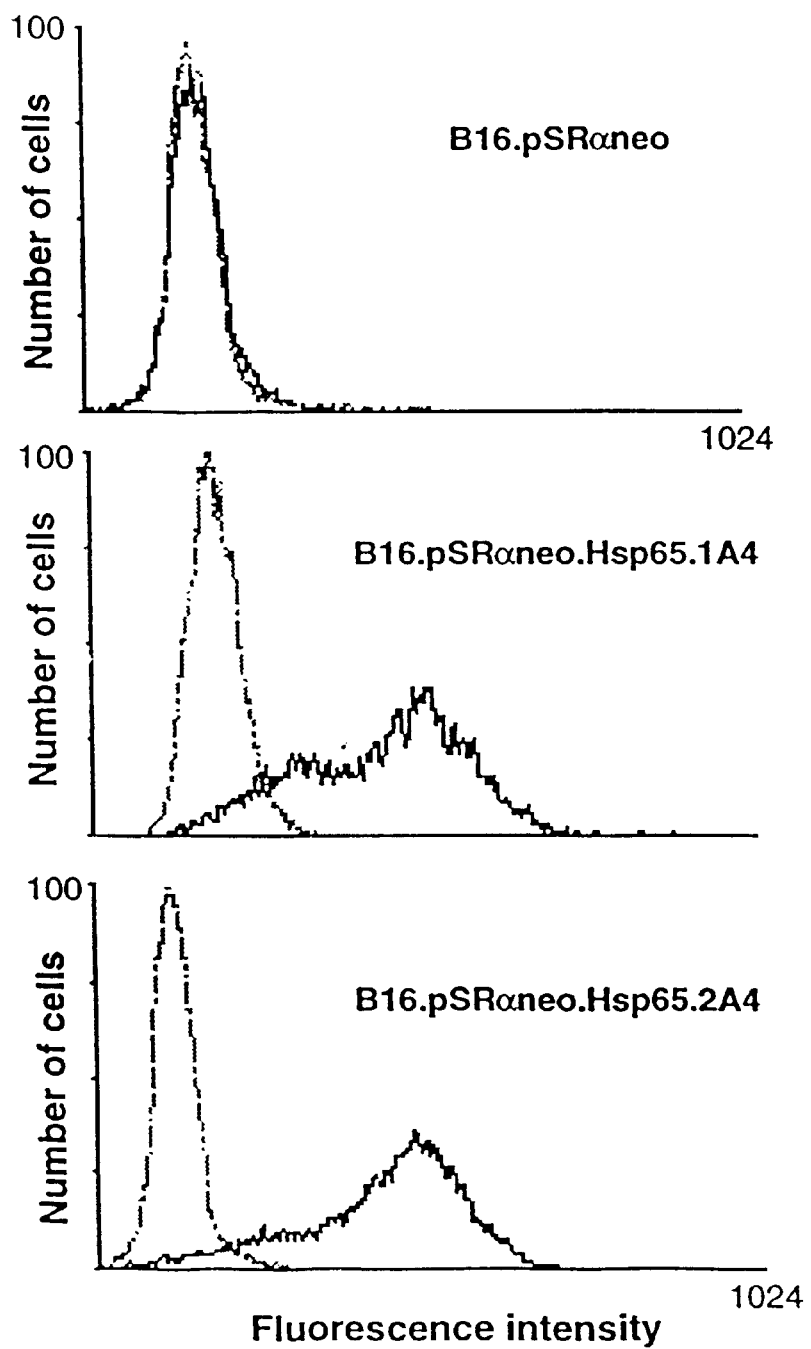
Figure 10D:
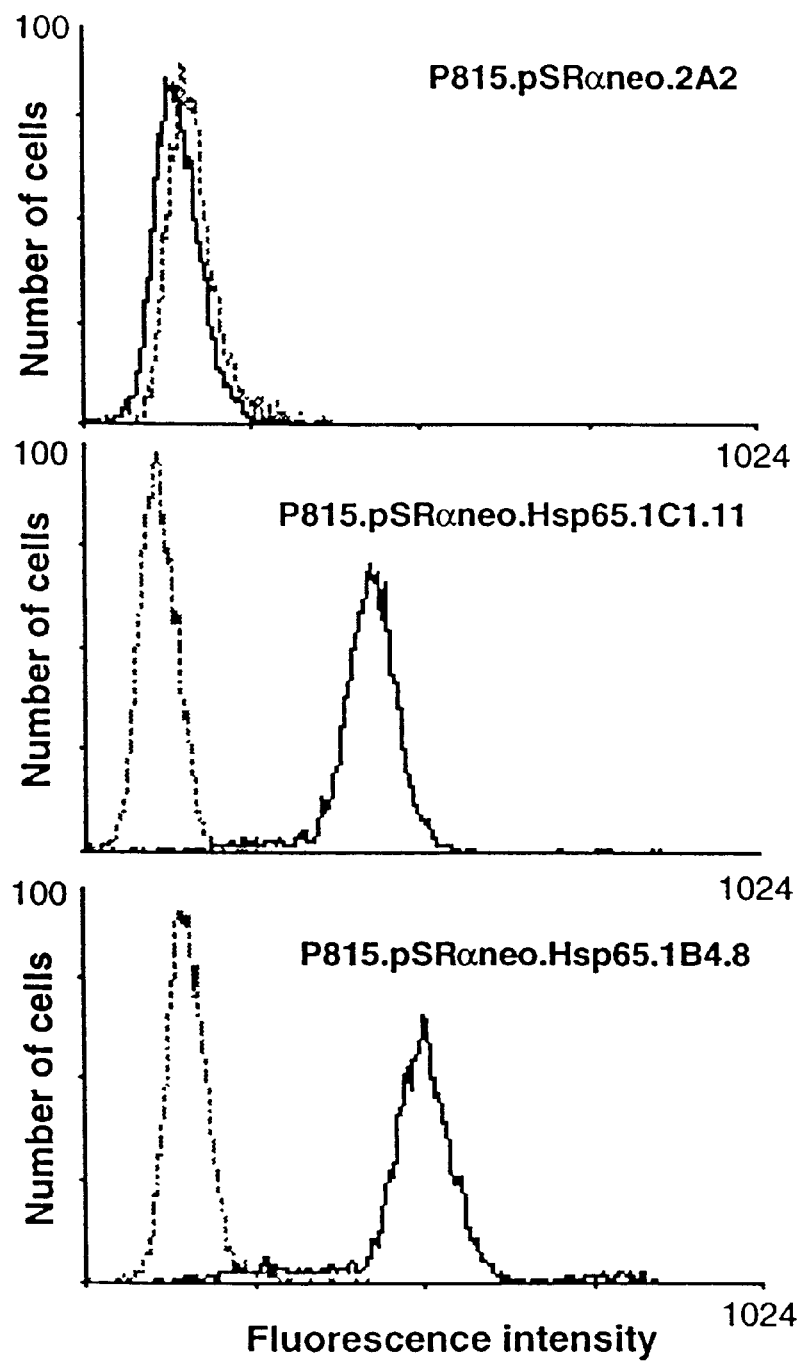

FIG. 8 shows the tumor incidence in syngeneic C57BL/6 ($H-2^b$) mice immunized intraperitoneal with either saline (open squares), B16.pSRαneo cells (closed circles) or B16.pSRαneo.Hsp72 cells (open circles), followed by subcutaneous challenge with live, wild type B16. All mice which scored positive for incidence went on to develop progressively growing challenge tumors. The tumor incidence exhibited by mice immunized with B16.pSRαneo.Hsp72 cells compared to mice immunized with either saline or B16.pSRαneo cells is significantly different, as measured by Log-Rank test (p<0.05). The results in FIG. 8 demonstrate the enhanced immunogenicity of chaperone-expressing tumor cells in vivo. Whereas pre-exposure of mice to control-transfected B16 cells did not afford protection against challenge with wild type B16 as compared to treatment with PBS alone, mice immunized with Hsp72-expressing B16 cells were significantly more resistant to wild type B16 challenge (FIG. 8).

Example 5

Increased Level of Surface MHC Class I Antigens on B16 Melanoma Cells Expressing Hsp65 but not on P815 Mastocytoma Cells Expressing Hsp65

P815 and B16 are highly malignant tumor cell lines which arose spontaneously in DBA/2 ($H-2^d$) and C57BL/6 ($H-2^b$) mice, respectively [Tahara et al. (1995) J. Immunol. 154:6466–6474; Tepper and Mule (1994) Hum. Gene. Ther. 5:153–164]. P815 is MHC class I-positive and is able to present endogenous antigens to MHC class I-restricted cytotoxic T lymphocytes (CTL) in vitro, whereas B16 expresses very little surface MHC class I and is phenotypically defective in the presentation of endogenous antigens to CTL [Huang et al. (1994) Science 264:961–965]. Both P815 and B16 lack the expression of costimulatory ligands, and thus fail to induce T cell responses when administered to syngeneic mice [Tepper and Mule (1994) Hum. Gene. Ther. 5:153–164; Huang et al. (1994) Science 264:961–965]. To address whether expression of a chaperone can enhance the immunogenicity of poorly immunogenic tumors in vivo, stable clones of P815 and B16 which express the 65 kD chaperonin/GroEL homolog (Hsp65) of *Mycobacterium tuberculosis* were generated and the effect on surface MHC I Levels was measured as follows.

A. Plasmids

The pSRαneo.RL13 plasmid is a eukaryotic expression vector which encodes the human heat-inducible 65 kD chaperone under the transcriptional control of the strong constitutive promoter SRα. The pSRαneo.RL13 plasmid was derived by cloning a 4.4 kb EcoRI-XbaI DNA fragment that included the complete coding region of the *Mycobacterium tuberculosis hsp65* gene (SEQ ID NO:3) (FIGS. 9A–9D) (Shinnick (1987) J. Bact. 169:1080; Shepherd et al. (1993) Cell 74:577–584) (kindly provided by Thomas Shinnick, CDC, Atlanta, Ga.) into the pSRαneo vector [Hock et al. (1993) Proc. Natl. Acad. Sci. USA 90:2774–2778]. Transcription of cloned genes in this vector is driven by the strong eukaryotic promoter SRα [Urban and Schreiber (1992) Ann. Rev. Immunol. 10:617–644].

B. Generation of Stable Tumor Cell Transfectants Expressing Hsp65

The B16 melanoma ($H-2^b$) and the P815 mastocytoma ($H-2^d$) cell lines were cultured in RPMI supplemented with 10% FBS (Intergen, Purchase, N.Y., USA), 2 mM L-glutamine, 100 IU/ml of penicillin, 100 μg/ml streptomycin, 50 μg ciprofloxacin, and 25 mM HEPES.

For transfection, tumor cell monolayers or settled suspensions were transfected with 10 μg of pSRαneo or pSRαneo.RL13 coated onto gold particles using Accel™ particle bombardment (AgraCetus, Inc., Middleton, Wis., USA) [Greenberg (1991) Adv. Immunol. 49:281–355]. Transfectants were cultured in supplemented RPMI plus 0.8 mg/ml (active) G-418 (Geneticin, Life Technologies, Grand Island, N.Y., USA), and the resultant G-418-resistant colonies were picked and maintained in the presence of 0.3 mg/ml G-418. Stable clones were then screened for the expression of Hsp65 by immunoblot and flow cytometric analysis.

C. SDS-PAGE and Immunoblot Protein Analysis

Proteins from tumor cell lysates prepared in Laemmli buffer were resolved by SDS-PAGE and transferred to nitrocellulose membranes by semi-dry electrophoresis [Melief (1992) Adv. Cancer Res. 58:143–175]. The membranes were incubated with the indicated dilution of monoclonal antibody ML-30 (provided by Dr. Juraj Ivanyi) or monoclonal antibody mc4220 (provided by Dr. Thomas Shinnick) which each recognize mycobacterial Hsp65. Equivalent antibodies may be purchased from StressGen, Victoria B. C., Canada. Immunoreactive proteins were visualized by incubation of the membranes with alkaline phosphatase-conjugated, affinity-purified goat anti-mouse serum (diluted 10,000-fold, Sigma, St. Louis, Mo., USA), followed by the addition of the chromogenic substrates 4-nitroblue tetrazolium chloride (NBT) and 5-bromo-4-chloro-3-indolyl-phosphate (BCIP) toluidine salt in 67% DMSO (v/v) (Boehringer Mannheim, Indianapolis, Ind.). The results are shown in FIG. 10.

Immunoblot analysis using two different monoclonal antibodies specific for mycobacterial Hsp65 (ML-30 and mc4220) revealed the presence of a single protein with an apparent molecular weight of 65 kD in lysates of B16 (FIG. 10A) and P815 (FIG. 10B) cells stably transfected with the plasmid pSRαneo.RL13 (denoted P815.pSRαneo.Hsp65 and B16.pSRαneo.Hsp65, respectively). No reactivity was observed in lysates of either untransfected parent cell line, or of P815 or B16 clones transfected with the negative control vector, pSRαneo (denoted P815.pSRαneo and B16.pSRαneo, respectively). As a positive control, actin could be detected in all lysates (not shown). Immunoprecipitation of lysates, but not supernatants, from radiolabeled B16.pSRαneo.Hsp65 cells gave similar results (not shown).

D. Flow Cytometric Analysis of Surface and Intracellular Proteins

Adherent tumor cell monolayers were harvested in PBS containing 1 mM EDTA, suspensions were washed in supplemented RPMI, and $2.5 \times 10^5$ cells were incubated with the appropriate monoclonal antibody (1 µg purified antibody, a 1/1000 dilution of ascites, or 50 µl hybridoma supernatant) in a final volume of 100 µl for 30 minutes at 4° C. Cells were washed with cold PBS containing 2% calf serum and incubated with 1 µg FITC-conjugated goat anti-rat or -mouse antibody (Boehringer Mannheim, Indianapolis, Ind., USA) for 30 minutes at 4° C. The monoclonal antibodies used were M1/42 (ATCC TIB126) [Boon and van der Bruggen (1996) J. Exp. Med. 183:725–729] and MS/114 (ATCC TIB120) which recognize monotypic determinants of the murine H-2 (MHC class I) and I-A (MHC class II) antigens, respectively; monoclonal antibody B22.249 (kindly provided by Dr. Alain Townsend) which recognizes a conformation-dependent determinant of the α2 domain of peptide-bound $D^b$ [Hellstrom and Hellstrom (1969) Adv. Cancer Res. 12:167–223]; the biotin-conjugated monoclonal antibody 28-8-6 (Pharmingen, San Diego, Calif., USA) which recognizes H-2 $K^b$ and $D^b$ independently of conformation; and AF6-88.5 (Pharmingen, San Diego, Calif., USA) which is specific for $K^b$. The dilutions of M1/42, AF6-88.5 and B22.249 monoclonal antibodies used in this investigation represent a super-saturating concentration as determined by flow cytometric titration against the highly NMC class I-positive cell lines L929 ($H-2^k$), P815 ($H-2^d$) and EL4 ($H-2^b$).

For intracellular staining, $2.5 \times 10^5$ cells were fixed with 1% formaldehyde in PBS and permeabilized in PBS containing 2% calf serum and 0.1% saponin. Permeabilized cells were incubated at room temperature for two hours with primary antibody (2 µg or a 5000-fold dilution of ascites), followed by a one hour incubation with FITC- or PE-conjugated goat-anti-mouse antibody or FITC-conjugated avidin (Beckton-Dickinson, San Jose, Calif., USA). Fluorescence was measured using a Becton Dickinson FacScan™ flow cytometer. The results are shown in FIGS. 10C and 10D and FIGS. 11A–11SS.

Cytometric analysis of permeabilized P815 and B16 transfectants stained with isotype control (dotted gray lines) or mc4220 (solid black lines) monoclonal antibody revealed specific reactivity with B16.pSRαneo.Hsp65 (FIG. 10C) and P815.pSRαneo.Hsp65 (FIG. 10D) clones (two representative clones of each are shown), but not with P815.pSRαneo or B16.pSRαneo clones. This analysis also shows that essentially all of the cells in each clonal population express Hsp65. No surface expression of Hsp65 could be detected by flow cytometry (not shown). These data demonstrate that MHC Class I levels were increased as a result of Hsp65 expression of the surface of B16 cells but not on P815 cells.

Figure 11A:
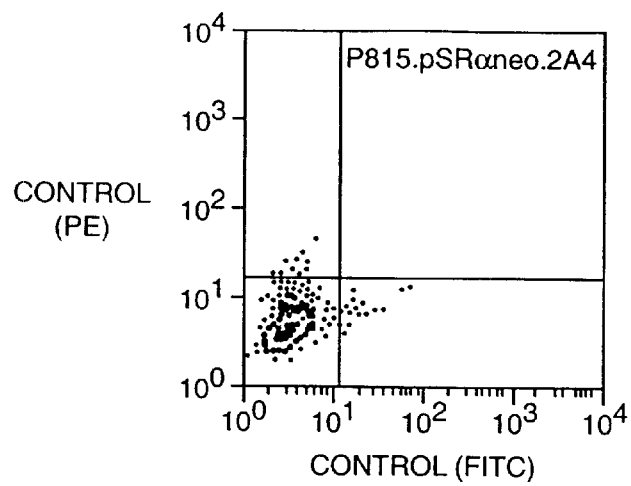
FIGS. 11A through 11SS show dual color flow cytometric analysis of P815.pSRαneo.Hsp65 (FIGS. 11A–11R) and B16.pSRαneo.Hsp65 (FIGS. 11S–11GG) clones for expression of surface MHC compared to cytoplasmic Hsp65, histogram representations of M1/42 reactivity exhibited by the B16.pSRαneo.Hsp65 clones (FIGS. 11HH–11KK) and by control B16.pSRαneo clones (FIGS. 11LL and 11MM), B16.pSRαneo.Hsp65 and B16.pSRαneo clones with the monoclonal antibodies M1/42, AF6-88.5 and B22.249 (FIGS. 11NN and 11OO), with AF6-88.5 alone (FIGS. 11PP and 11QQ), and with B22.249 alone (FIGS. 11RR and 11SS).
Figure 11B:
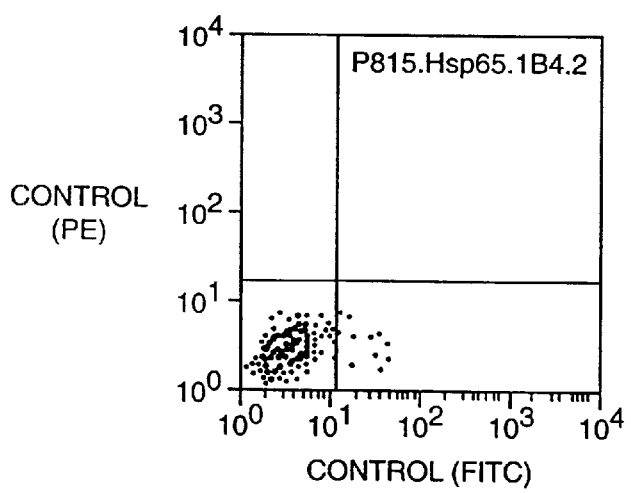
Figure 11C:
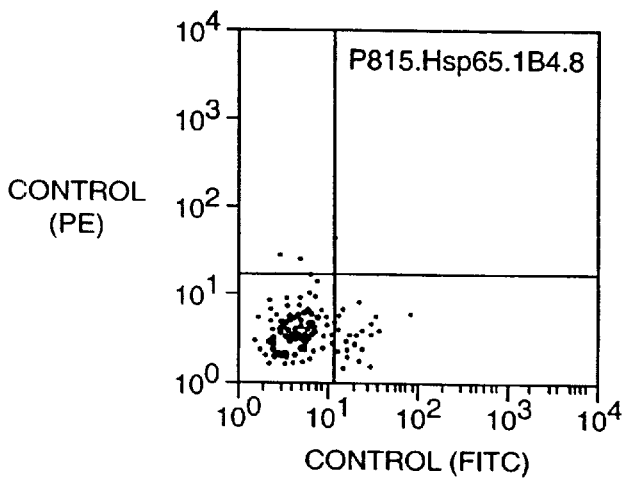
Figure 11D:
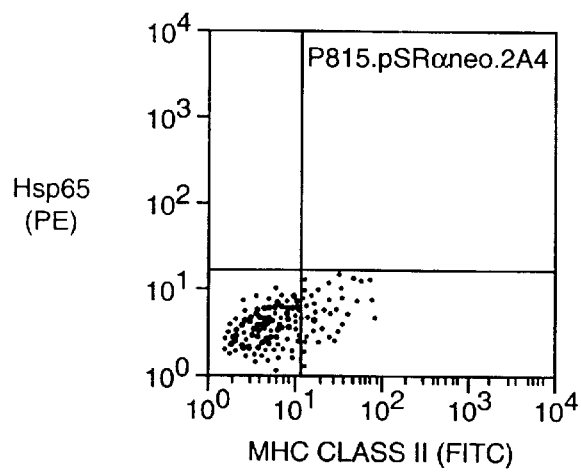
Figure 11E:
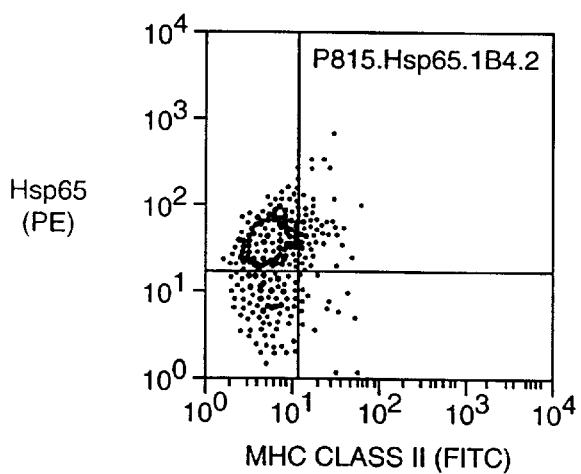
Figure 11F:
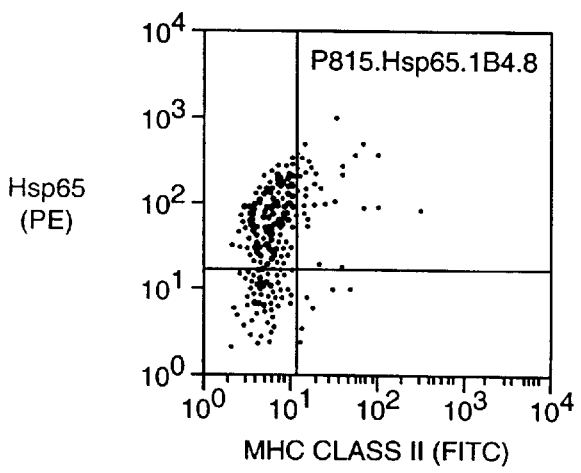
Figure 11G:
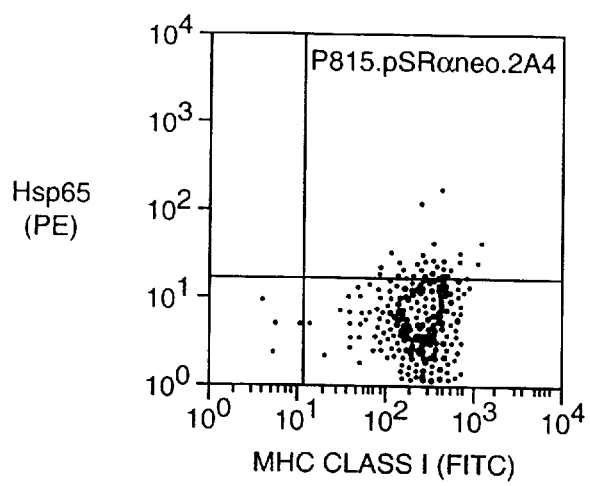
Figure 11H:
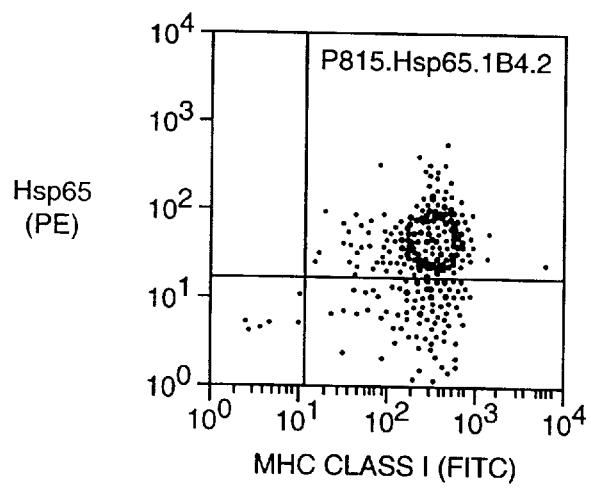
Figure 11I:
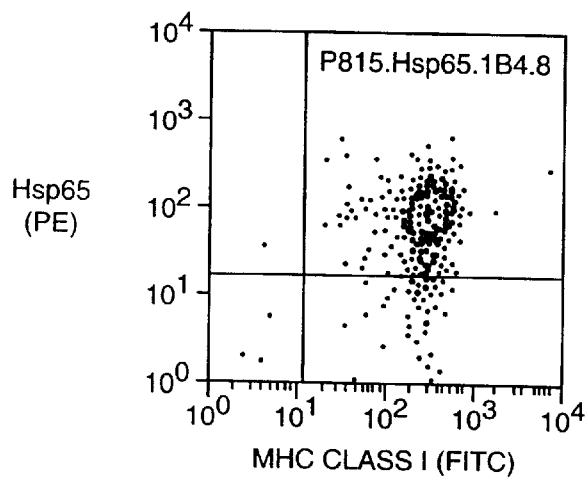
Figure 11J:
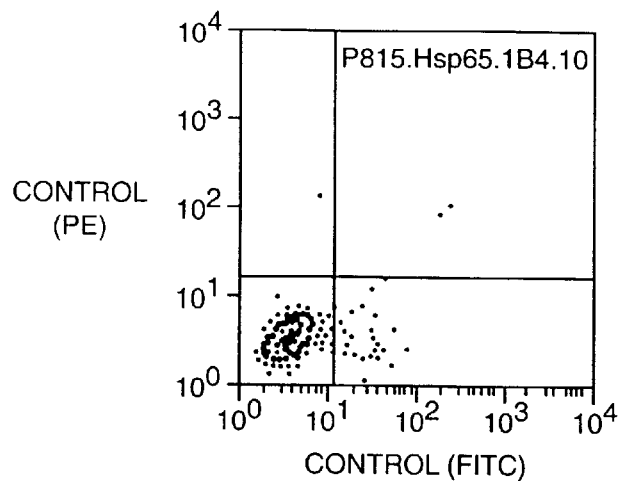
Figure 11K:
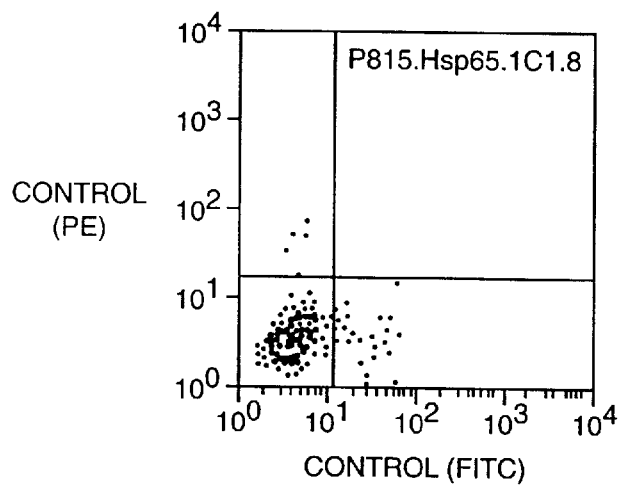
Figure 11L:
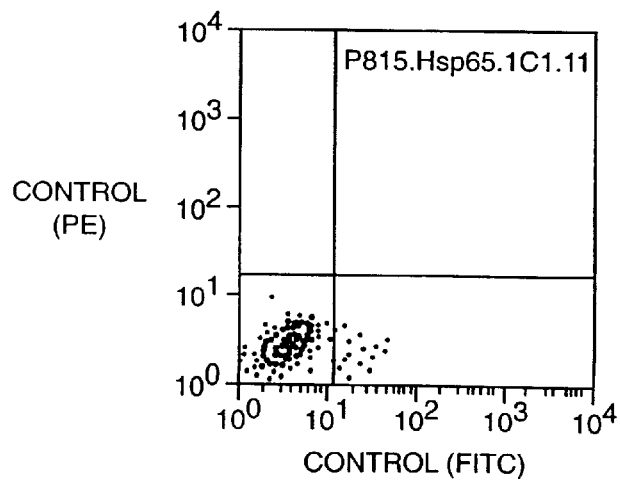
Figure 11M:
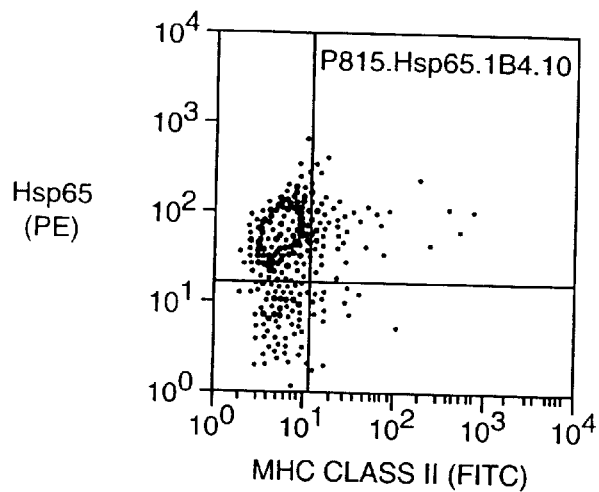
Figure 11N:
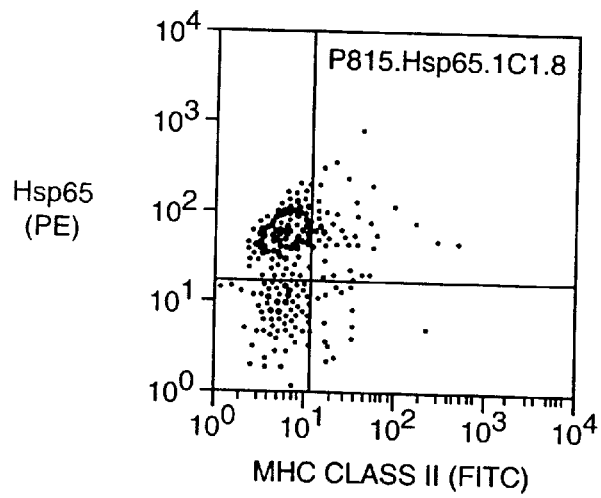
Figure 11O:
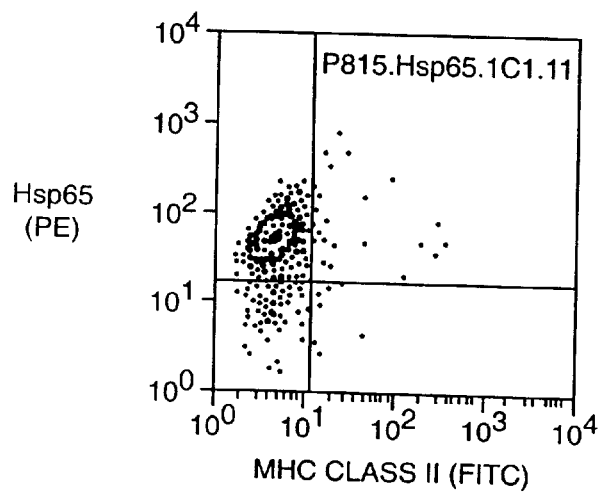
Figure 11P:
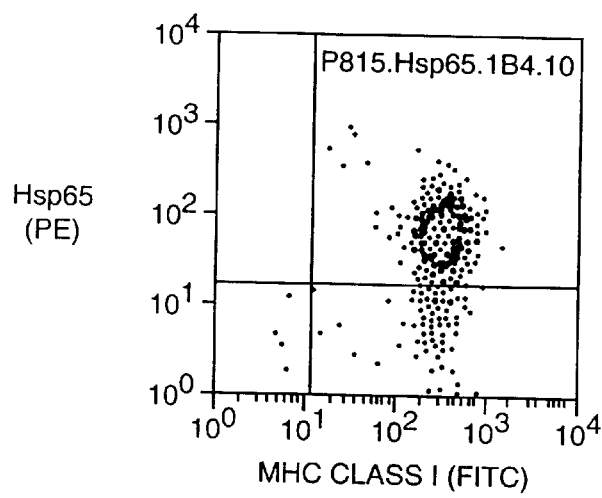
Figure 11Q:
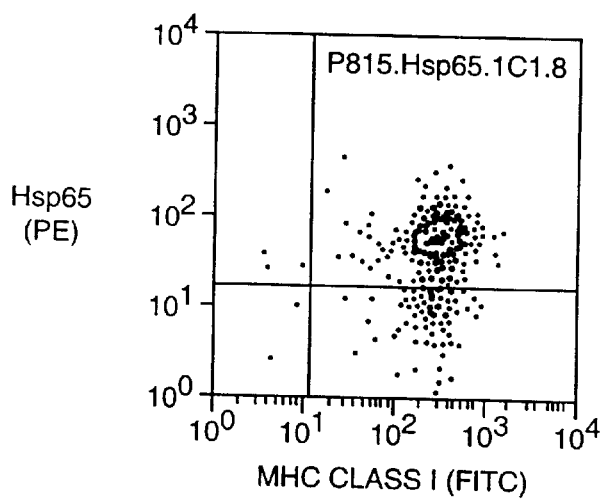
Figure 11R:
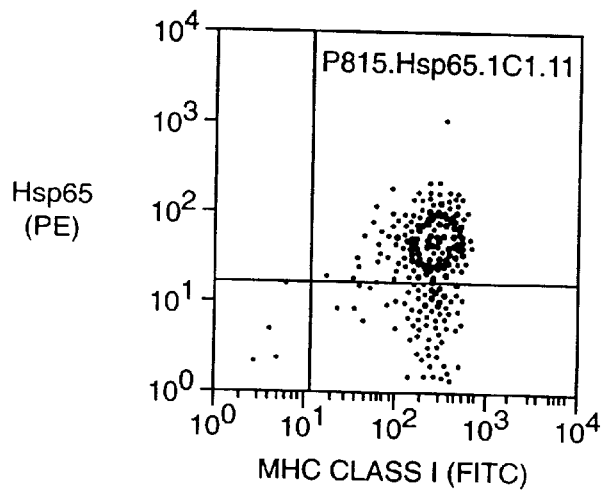
Figure 11S:
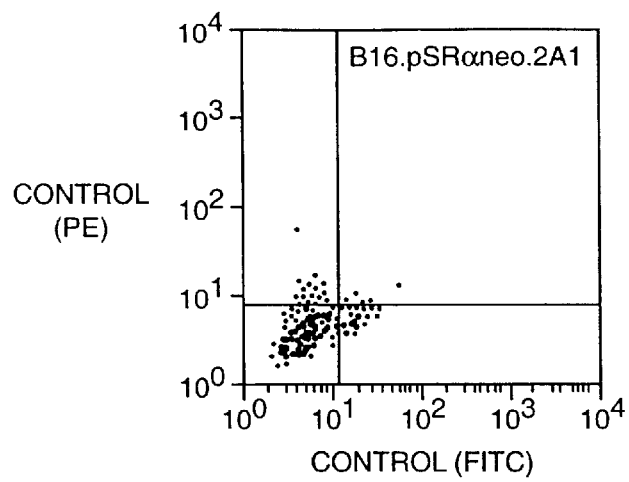
Figure 11T:
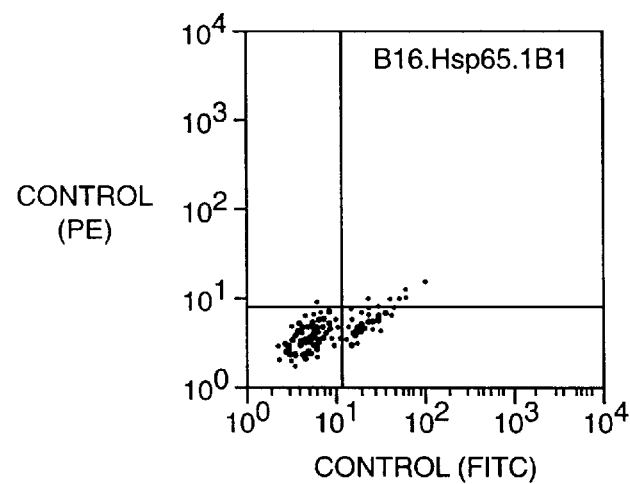
Figure 11U:
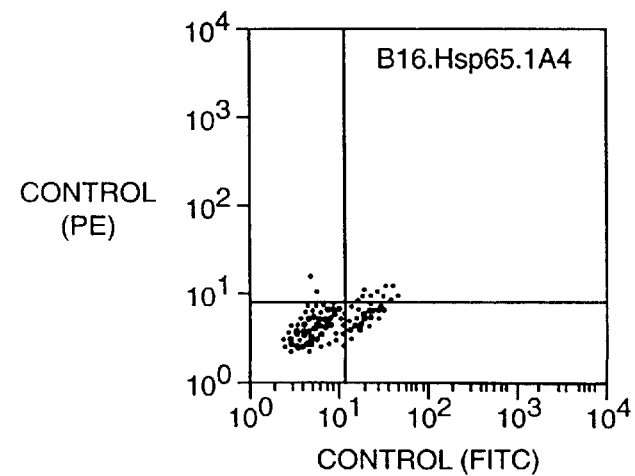
Figure 11V:
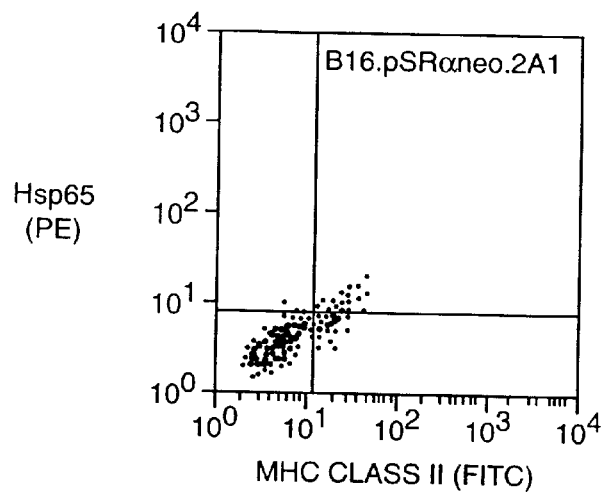
Figure 11W:
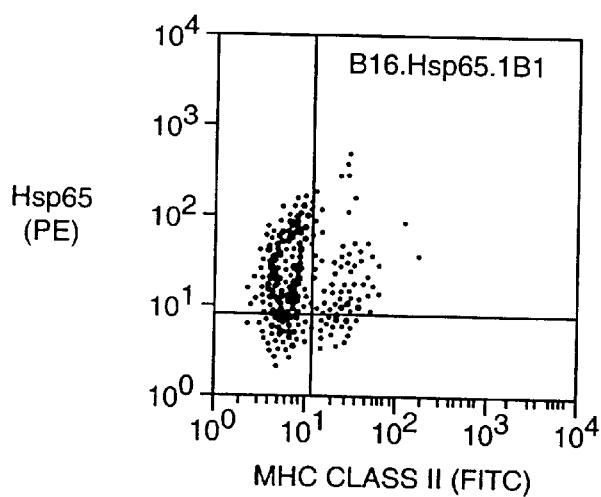
Figure 11X:
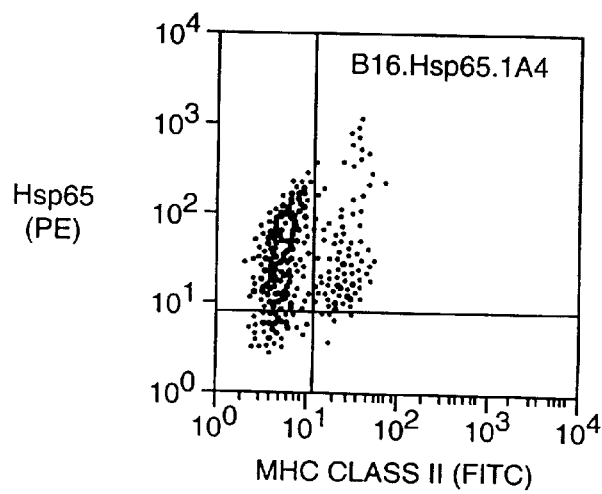
Figure 11Y:
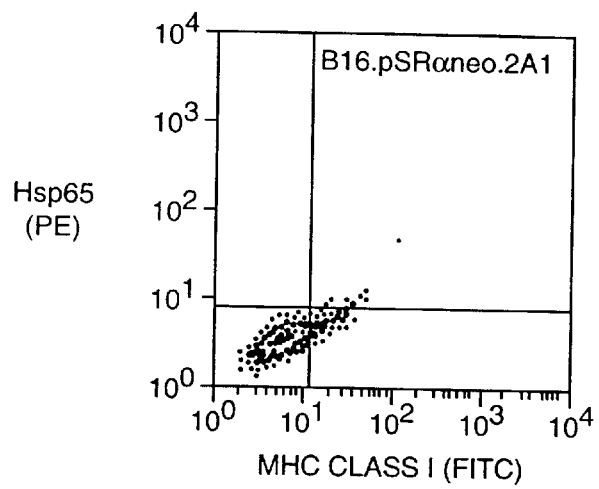
Figure 11Z:
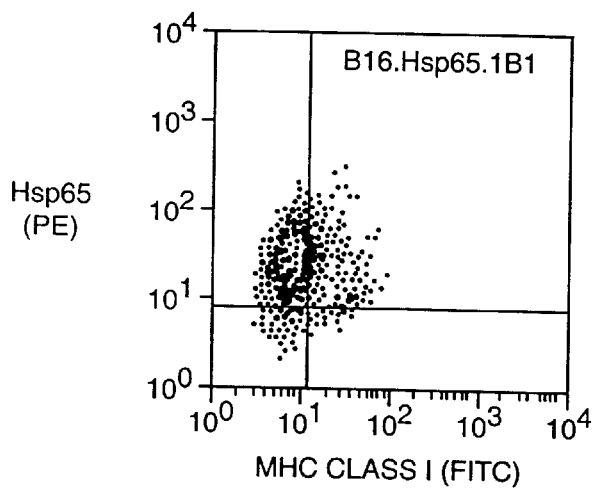
Figure 11A:
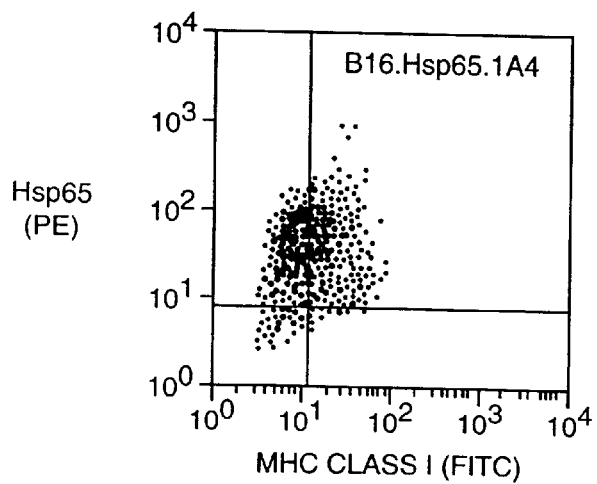
Figure 11B:
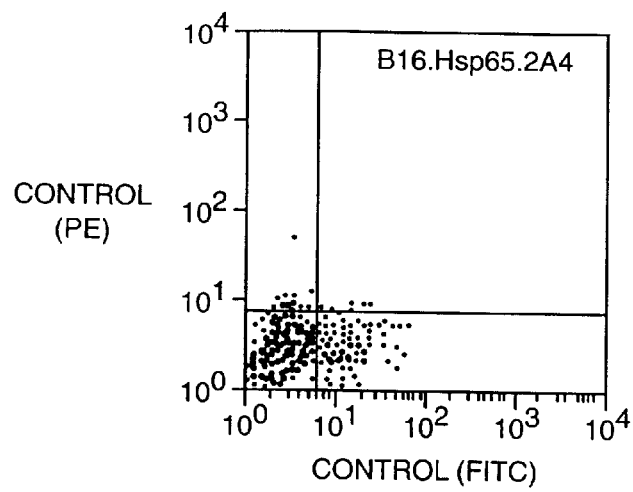
Figure 11C:
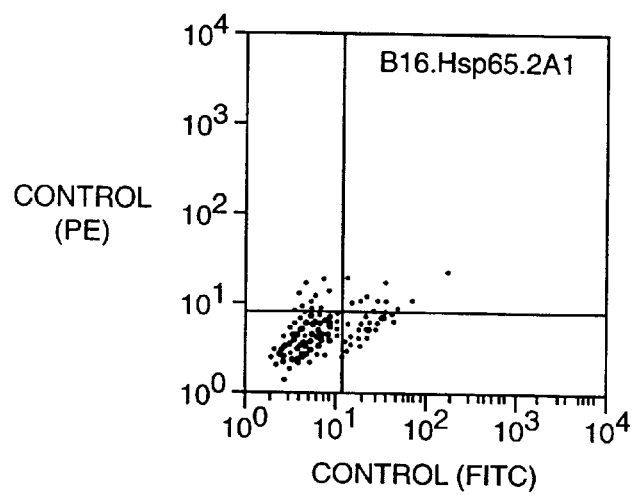
Figure 11D:
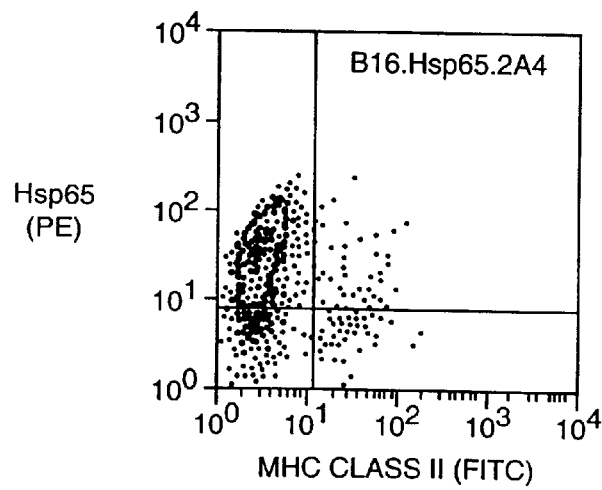
Figure 11E:
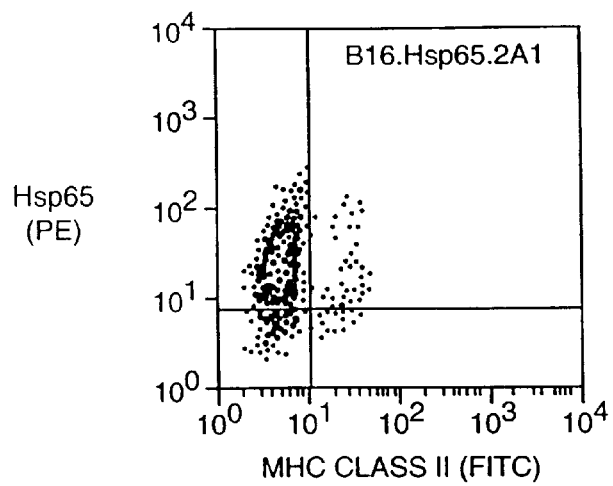
Figure 11F:
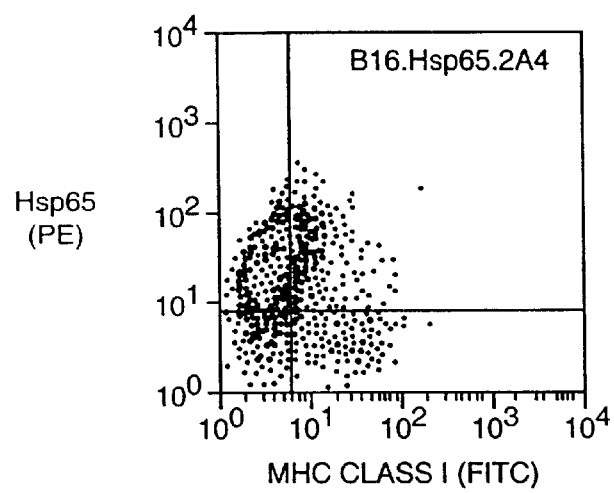
Figure 11G:
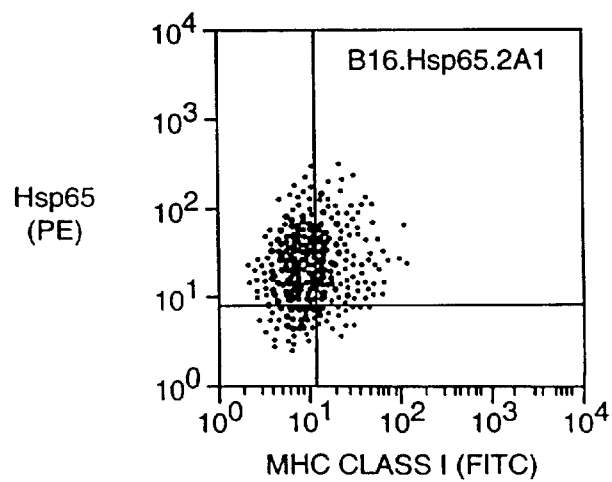
Figure 11H:
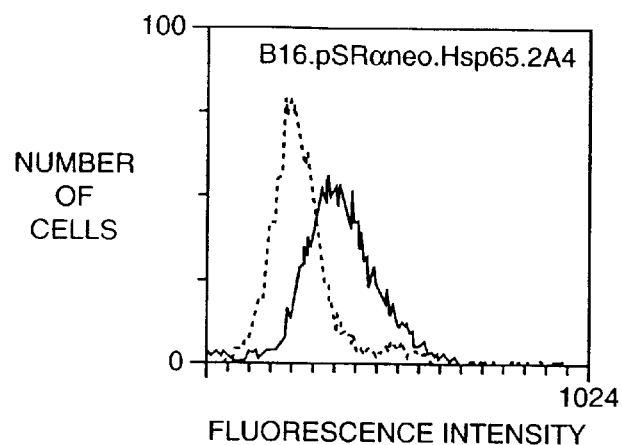
Figure 11I:
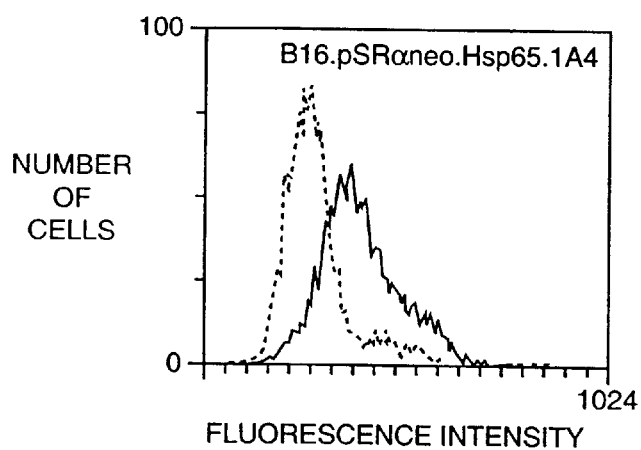
Figure 11J:
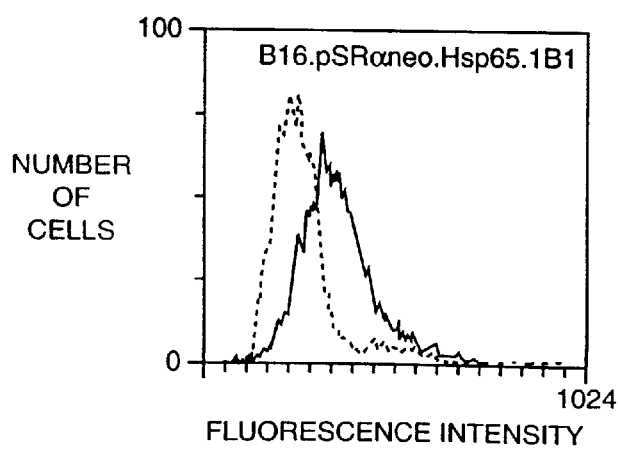
Figure 11K:
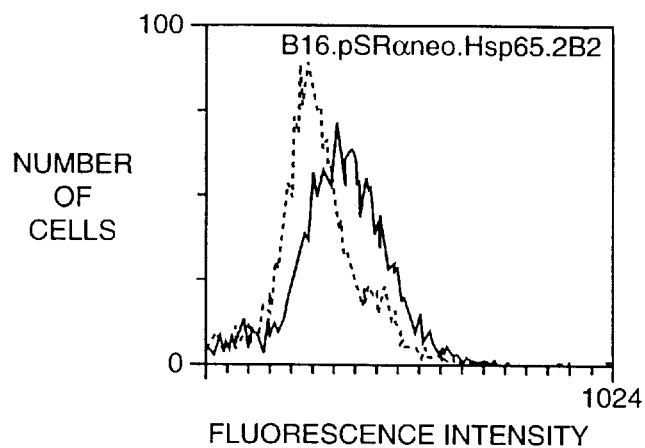
Figure 11L:
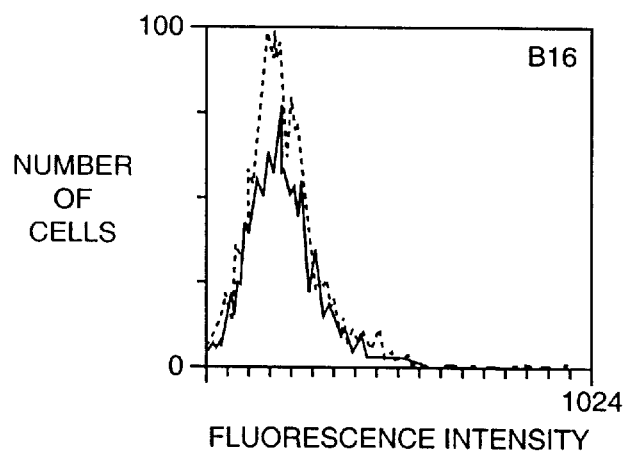
Figure 11M:
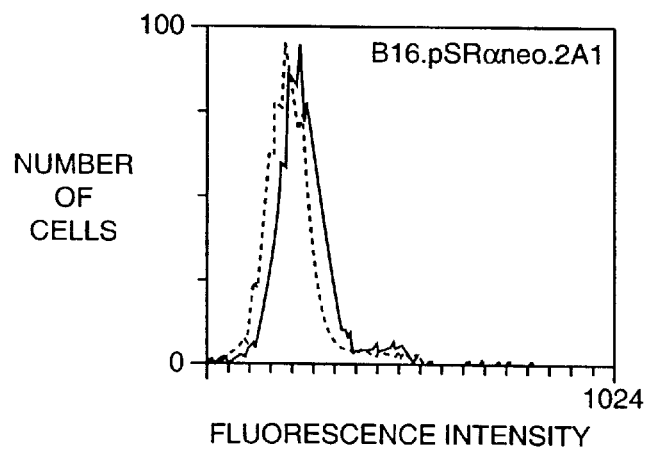
Figure 11N:
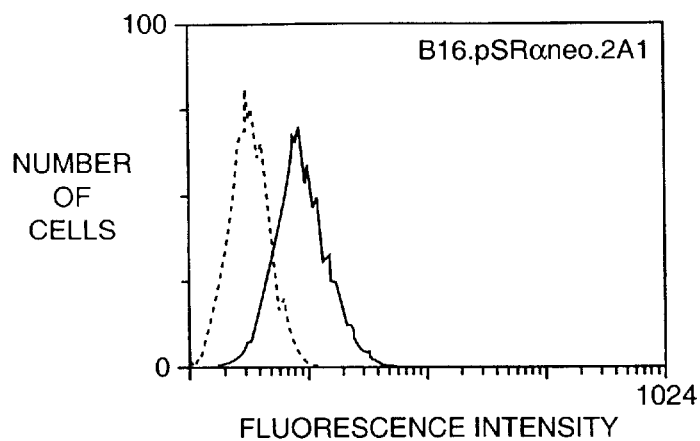
Figure 11O:
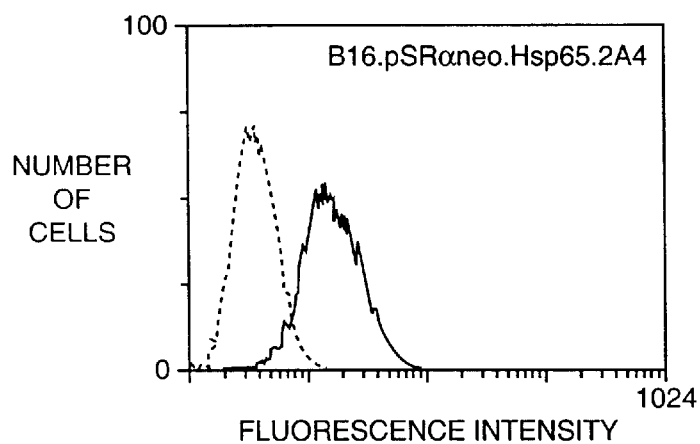
Figure 11P:
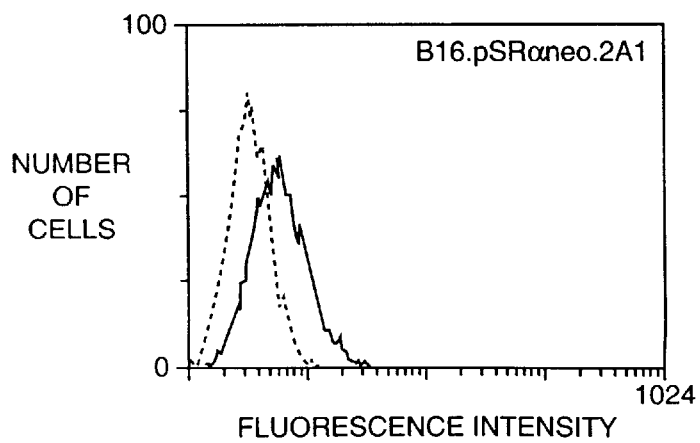
Figure 11Q:
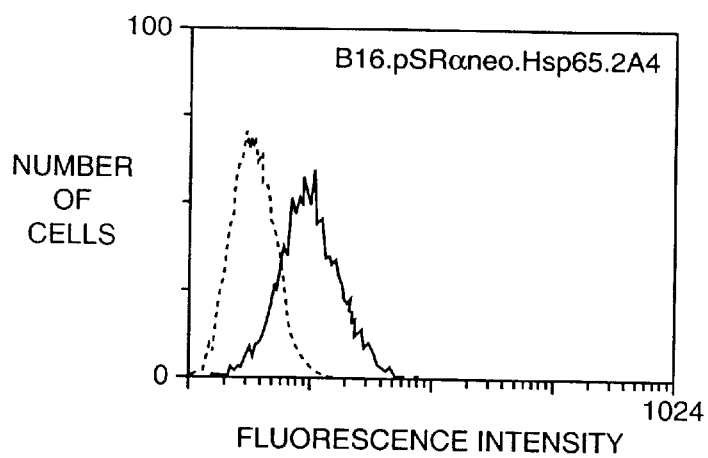
Figure 11R:
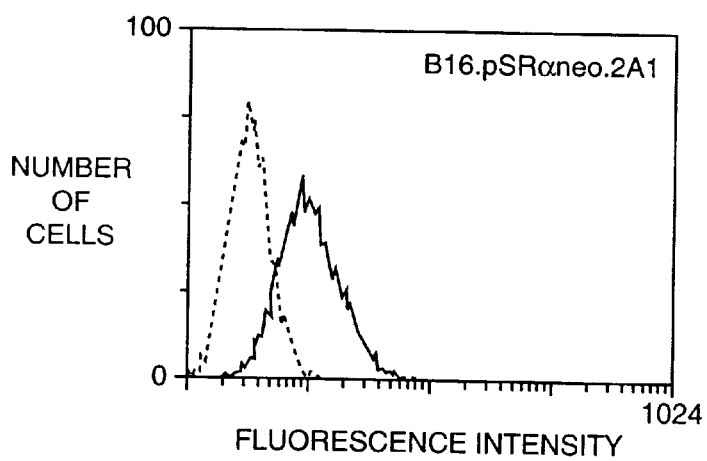
Figure 11S:
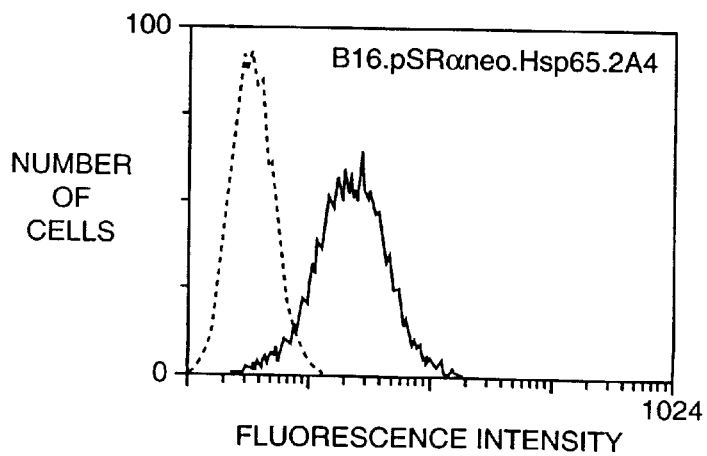

FIGS. 11A–11SS show the results of an analysis of MHC class I and II surface antigen expression by P815.pSRαneo.Hsp65 and B16.pSRαneo.Hsp65 clones. Dual color flow cytometric analysis for expression of surface MHC compared to cytoplasmic Hsp65 of the P815.pSRαneo.Hsp65 clone is shown in FIGS. 11A–11R and for the B16.pSRαneo.Hsp65 clone in FIGS. 11S–11GG. MHC class I and II were visualized by staining live cells with M1/42 or MS/114, respectively, followed by FITC-conjugated goat-anti-rat secondary antibody. Monoclonal antibody M1/42 (ATCC TIB126) [Boon and van der Bruggen (1996) J. Exp. Med. 183:725–729] and MS/114 (ATCC TIB120) recognize monotypic determinants of the murine H-2 (MHC class I) and I-A (MHC class II) antigens, respectively. Cells were then fixed and permeabilized and intracellular Hsp65 was visualized with mc4220 followed by PE-conjugated goat-anti-mouse antibody. Density plots of one P815.pSRαneo clone (2A4) and five P815.pSRαneo.Hsp65 clones (1B4.2, 1B4.8, 1B4.10, 1C1.8 and 1C1.11) are shown in FIGS. 11A–11R. Density plots of one control B16.pSRαneo clone (2A1) and four B16.pSRαneo.Hsp65 clones (1B1, 1A4, 2A1, and 2A4) are shown in FIGS. 11S–11GG. No significant MHC class II expression was exhibited by any clone of P815 or B16. Also, the mean fluorescence intensity (MFI) of MHC class I staining exhibited by P815.pSRαneo.Hsp65 clones did not differ significantly from that of P815.pSRαneo clones.

FIGS. 11HH–11KK show histogram representations of M1/42 reactivity exhibited by the B16.pSRαneo.Hsp65 clones shown in FIGS. 11S–11GG revealed significant amounts of surface MHC class I antigen present, whereas the parent B16 melanoma line and control B16.pSRαneo clones (clone 2A1 is shown here) displayed little or no MHC class I surface antigen (FIGS. 11LL–11MM). Solid black lines show staining with specific antibody; dotted gray lines show staining with isotype control antibody. The MFI of B16.pSRαneo.Hsp65 clones stained with M1/42 is two- to three-fold greater than that of the parent B16 cells or the B16.pSRαneo clones stained with M1/42, or than that of B16.pSRαneo.Hsp65 clones stained with isotype control antibody. In separate experiments, staining of live-gated B16.pSRαneo.Hsp65 and B16.pSRαneo clones with the monoclonal antibodies M1/42, AF6-88.5 and B22.249 revealed increased levels of total MHC class I (FIGS. 11NN–11OO) as well as increased levels of the individual $K^b$ (FIGS. 11PP–11QQ) and $D^b$ (FIGS. 11RR–11SS) gene products on B16.pSRαneo.Hsp65 clone 2A4 compared to the levels present on the B16.pSRαneo control. The B16.pSRαneo.Hsp65 and B16.pSRαneo clones express comparable levels of other membrane surface proteins such as $β_2$ integrin (CD18) and H-CAM (CD44) (not shown).

Analysis of B16 revealed significant levels of stably folded MHC class I antigen on the surface of B16 clones expressing Hsp65 (FIGS. 11S–11GG, 11HH–11KK, and 11NN–11OO), and both $K^b$ and $D^b$ gene products were shown to be upregulated (FIGS. 11PP–11QQ and 11RR–11SS). This increase in surface MHC class I was not observed in corresponding control clones which express the foreign bacterial protein aminoglycoside phosphotransferase (neo), as these clones exhibit MHC class I profiles similar to that of parent B16 (FIGS. 11S–11GG and 11HH–11KK). This effect appears to be specific for MHC class I, because Hsp65 expression did not affect the levels of MHC class II (FIGS. 11S–11GG) or of other surface proteins such as $\beta_2$ integrin or CD44 (not shown).

E. MHC Class I α Chain mRNA and Protein Determination

In order to determine if enhanced surface expression was due to increased synthesis of MHC Class I, the steady state levels of MHC Class I α chain mRNA and protein were measured (FIG. 12).

mRNA transcripts of MHC Class I MHC a chain were measured by semi-quantitative RT-PCR as follows. To design a primer set which specifically amplifies a region from both the $K^b$ and $D^b$ transcripts, the cDNA sequences of the murine $K^b$ (GenBank accession #J00400) and $D^b$ (GenBank accession #K00129) alleles of MHC class I were aligned using the Clustalw 1.5 Multiple Sequence Alignment Program [Janeway and Bottomly (1994) Cell 76:275–286]. Primers corresponding to sequences within regions of 100% identity between the two alleles were designed: 5'-GCGATTACATCGCCCTGAACG-3' (sense) (SEQ ID NO:4), representing base pairs 119 to 140 of the $K^b$ sequence, and 5'-AGGTCCGTCGACAGAAGTGC-3' (antisense) (SEQ ID NO:5), complementary to base pairs 870 to 890 of the $K^b$ sequence. Total RNA was isolated from lysates of B16 transfectants using RNeasy purification columns (Qiagen), and cDNA was generated using M-MuLV reverse-transcriptase (Gibco BRL) primed with oligo $dT_{15}$ (10 uM; Boehringer Mannheim). Various amounts of the RT reaction were then titered into separate PCR reactions as template for the amplification of either $K^b/D^b$ or G3PDH (control). Amplified products were subjected to agarose electrophoresis and visualized by ethidium bromide staining. Band densities (in pixels/cm$^2$) were quantified from digitized gel photographs using NIH Image 1.60b7 image analysis software. The results are shown in FIG. 12.

Figure 12A:
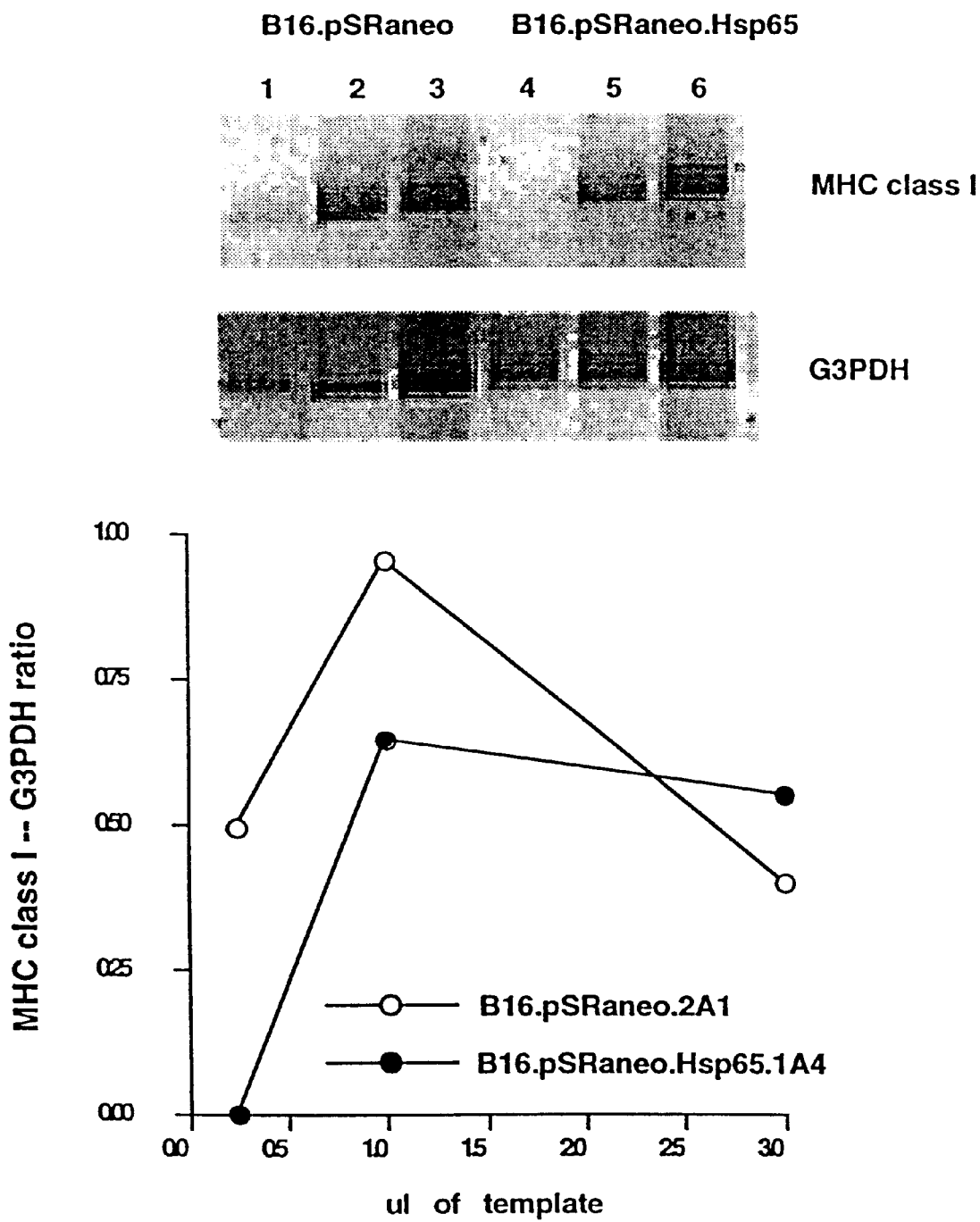
FIG. 12(A) upper panel shows the negative image of an ethidium bromide-stained agarose gel in which MHC class I α chain-specific and G3PDH-specific sequences were amplified from varying amounts of cDNA template from B16.pSRαneo and B16.pSRaneo.Hsp65.

FIG. 12A depicts the negative image of an agarose gel in which MHC class I α chain-specific and G3PDH-specific sequences were amplified from 0.25 ul (lanes 1 and 4), 1.0 ul (lanes 2 and 5), or 3.0 ul (lanes 3 and 6) of cDNA template. Note that the amplification achieved from 0.25 ul (lanes 1 and 4) or 1.0 ul (lanes 2 and 5) of cDNA template has not reached saturation (compared to lanes 3 and 6), therefore products derived from these reactions can be compared semi-quantitatively. The graph (lower panel) represents the α chain-specific band densities (in pixels/cm$^2$) normalized to the G3PDH internal control for each starting quantity of template. Analyzed in this manner, the steady-state levels of MHC class I mRNA present in B16.pSRαneo.Hsp65 cells are no higher than steady-state levels present in B16.pSRαneo control cells.

Figure 12B:
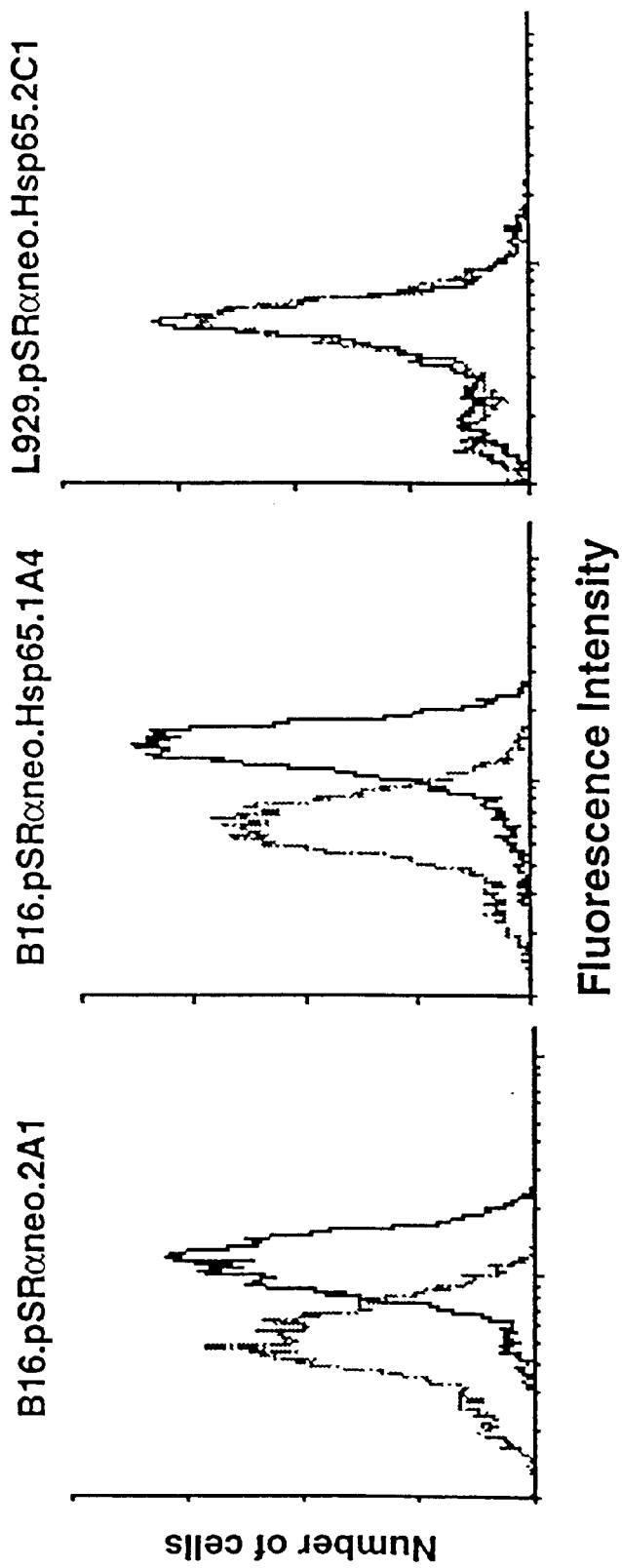

Monoclonal antibody 28-8-6, which recognizes the H-2 $K^b$ and $D^b$ gene products independently of conformation, was used to quantify total cellular MHC class I α chain protein by flow cytometric analysis of permeabilized cells. FIG. 12B shows the quantification of total cellular MHC class I α chain protein by flow cytometric analysis of permeablized cells using monoclonal antibody 28-8-6. Solid black lines show staining with 28-8-6; dotted gray lines show staining with isotype control antibody. The relative geometric mean fluorescence intensities (MFI) of B16.pSRαneo.Hsp65.1A4 and B16.pSRαneo.2A1 stained with 28-8-6 (expressed as a percentage of the isotype control MFI) were 280% and 274%, respectively. This method of quantification is specific for H-$2^b$ α chains, because 28-8-6 exhibited no reactivity against a tumor cell of the H-$2^k$ haplotype which also expresses Hsp65 (L929.pSRαneo.Hsp65.2C1).

This data shows that Hsp65-expressing B16 clones and control B16 clones contain comparable steady-state levels of total MHC class I α chain mRNA (FIG. 12A). Also, permeabilized Hsp65-expressing B16 cells exhibited no increase in total cellular MHC class I protein as measured by flow cytometry with a monoclonal antibody specific for the $K^b$ and $D^b$ gene products (FIG. 12B). These data show that the enhanced surface expression was not due to increased synthesis of MHC class I.

Example 6

Enhanced Processing and Presentation of Endogenous Antigens to MHC Class I-Restricted CTL In Vitro This Example addressed whether the increase in MHC class I antigen on the surface of Hsp65-expressing B16 tumor cells is immunologically significant, i.e., whether the expression of Hsp65 influences the capacity of these cells to process and present endogenous antigens to MHC class I-restricted CTL. The viral infection model described above (i.e., in which mice of the H-$2^b$ haplotype are infected with LCMV) was employed. CTL effector cells were prepared and the CTL assay was carried out as described in Example 2. The results are shown in FIG. 13.

Figure 13A:
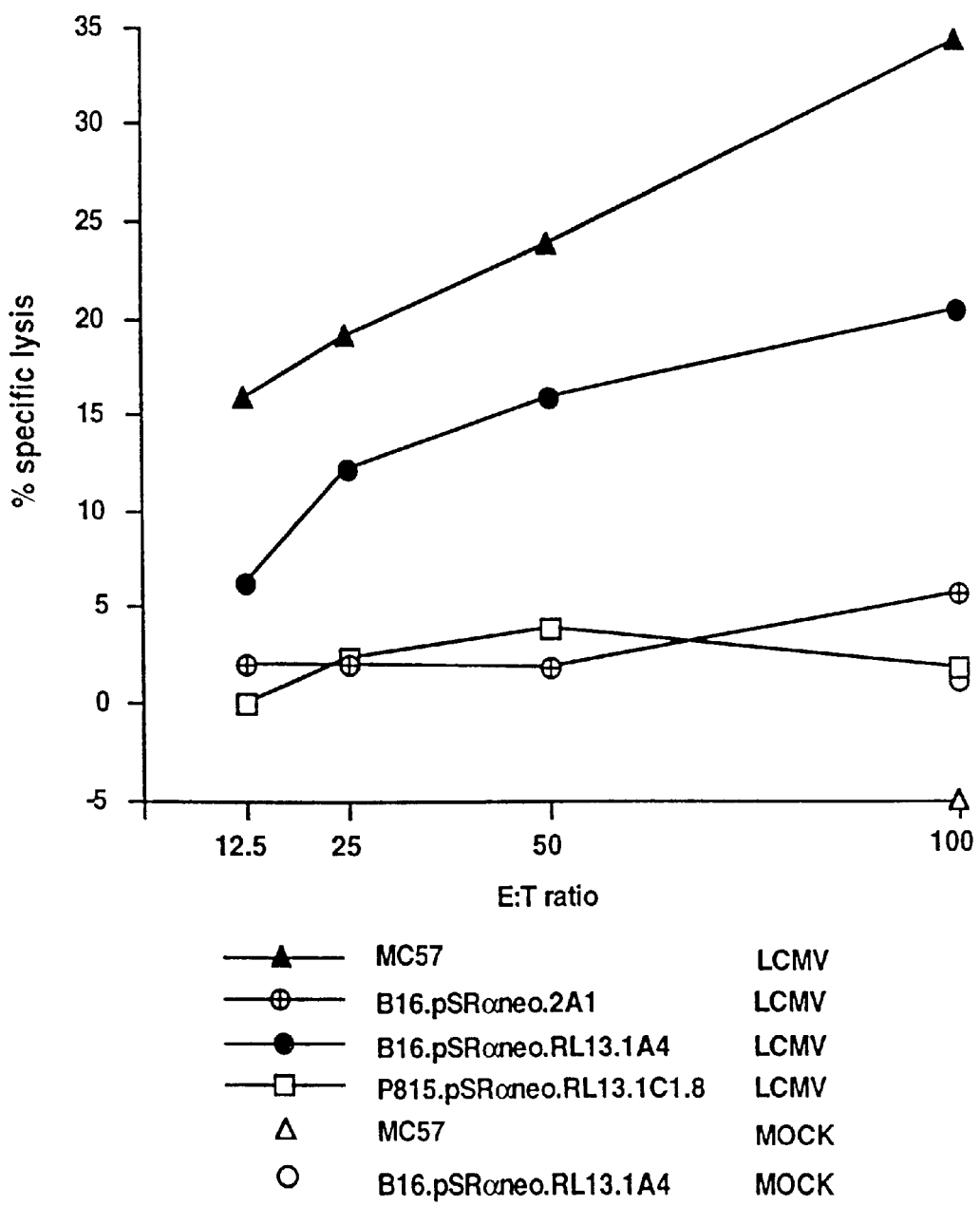
FIG. 13 shows the results of cytotoxicity assays in which the cytolytic activity of CTL populations from two separate LCMV-infected mice (A) and (B) was measured against LCMV- or mock-infected targets. The LCMV-infected targets included MC57, B16.pSRαneo.2A1, B16.pSRαneo.RL13.1A4, P815.pSRαneo.RL13.1C1.8. Mock-infected targets included MC57 and B16.pSRαneo.RL13.1A4.
Figure 13B:
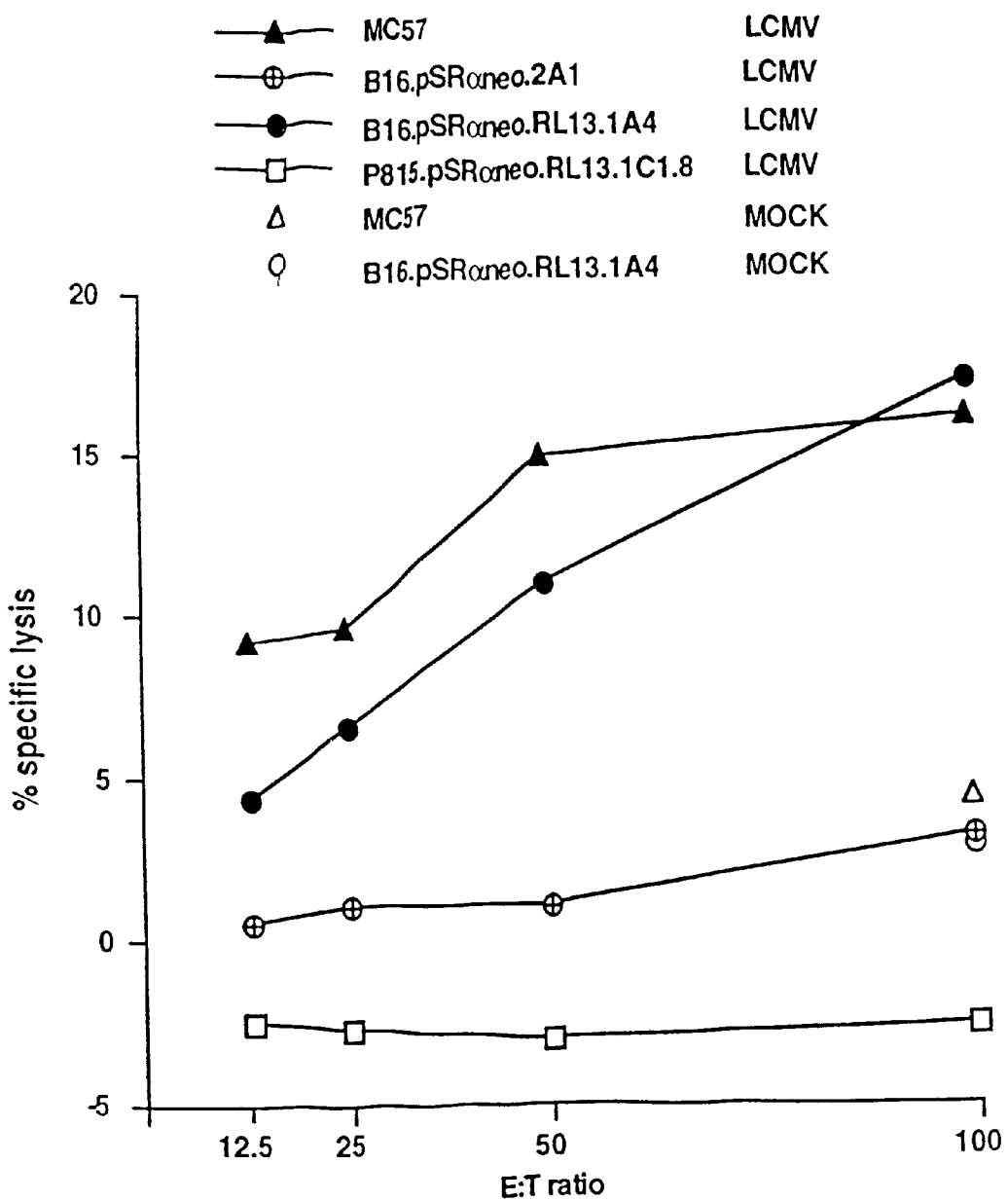

FIGS. 13A and 13B depict a representative cytotoxicity assay in which the cytolytic activity of CTL populations from two separate LCMV-infected mice was measured against LCMV- or mock-infected targets. MC57 is a MHC class I$^+$ fibroblast cell line of C57BL/6 origin which, when infected with LCMV, is highly susceptible to LCMV-specific CTL lysis. LCMV-infected B16.pSRαneo.Hsp65 clone 1A4 (i.e., the B16.pSRαneo.RL13.1A4 of FIG. 13) (closed circles) was lysed by LCMV-specific CTL to levels approaching those exhibited by LCMV-infected MC57 (closed triangles). B16.pSRαneo.2A1 (crossed circles) and P815.pSRαneo.Hsp65 (open squares) (i.e., the p815.pSRαneo.RL13.1C1.8 of FIG. 13) clones were not lysed, nor were mock-infected MC57 (open triangles) and B16.pSRαneo.Hsp65 (open circles) (i.e., the B16.pSRαneo.RL13.1A4 of FIG. 13) clones. Separate experiments as in FIGS. 13A and 13B using B16.pSRαneo.Hsp65 clone 2A4 gave similar results (not shown). In addition, no lysis of LCMV-infected MC57 or B16.pSRαneo.Hsp65 cells was observed when CTL derived from LCMV-infected, allogeneic mice (BALB/c, H-$2^d$) were used as effectors (not shown). LCMV infection of targets was confirmed by immunoblot analysis using a GP-specific antiserum (not shown). Spontaneous release was <17%.

These data demonstrate that LCMV-infected, Hsp65-expressing B16 cells, but not control cells, are recognized and killed in an MHC-restricted, antigen-specific manner.

Example 7

Enhanced Recognition of Hsp65-Expressing Tumor Cells by MHC Class I-Restricted T Cells In Vitro The enhanced resistance of mice immunized with Hsp65-expressing tumor cells compared to mice immunized with control cells suggests that Hsp65-expressing tumor cells are recognized more efficiently by tumor-specific T cells in vivo. To specifically address the recognition of Hsp65-expressing tumor cells by T cells in vitro, Hsp65-expressing clones were used as targets for allospecific CTL-mediated lysis. Enhanced susceptibility of P815.pSRαneo.Hsp65 and B16.pSRαneo.Hsp65 clones to lysis by allospecific T lymphocyte effectors was investigated by using mixed lymphocyte reactions (MLR) as a source of CTL effectors directed against either the H-$2^d$ or the H-$2^b$ haplotype of MHC class I as described above. The results are shown in FIGS. 14 and 15.

FIG. 14A depicts two representative experiments in which the cytolytic activity of two separate allospecific CTL populations was measured against P815, P815.pSRαneo, P815.pSRαneo.Hsp65, LPS-activated H-$2^d$ splenocytes and B16.pSRαneo.Hsp65 targets (experiment #1, upper panel). P815.pSRαneo.Hsp65 clone 1C1.11 (closed circles) was lysed to a greater degree than P815 (open circles) and LPS-activated DBA/2 splenocytes (open triangles). A clone of B16.pSRαneo.Hsp65 (H-$2^b$) (open diamonds) was not lysed. In a separate experiment with CTL effectors obtained from a different MLR (experiment #2, lower panel), four additional P815.pSRαneo.Hsp65 clones (1B4.2, 1B4.8, 1B4.10 and 1C1.8; closed symbols) and the H-$2^b$ tumor EL4 (open diamonds) were tested for their susceptibility to allospecific CTL-mediated cytotoxicity at very low effector-to-target ratios.

The results in FIG. 14A show that CTL specific for the H-$2^d$ haplotype of MHC class I lysed parent and control-transfected P815 cells efficiently. On the other hand, P815 clones expressing Hsp65 were still lysed to a greater degree. Lysis of Hsp65-expressing P815 clones by the H-$2^d$-specific CTL was MHC-restricted, because B16 cells expressing Hsp65 were not lysed.

Figure 14B:
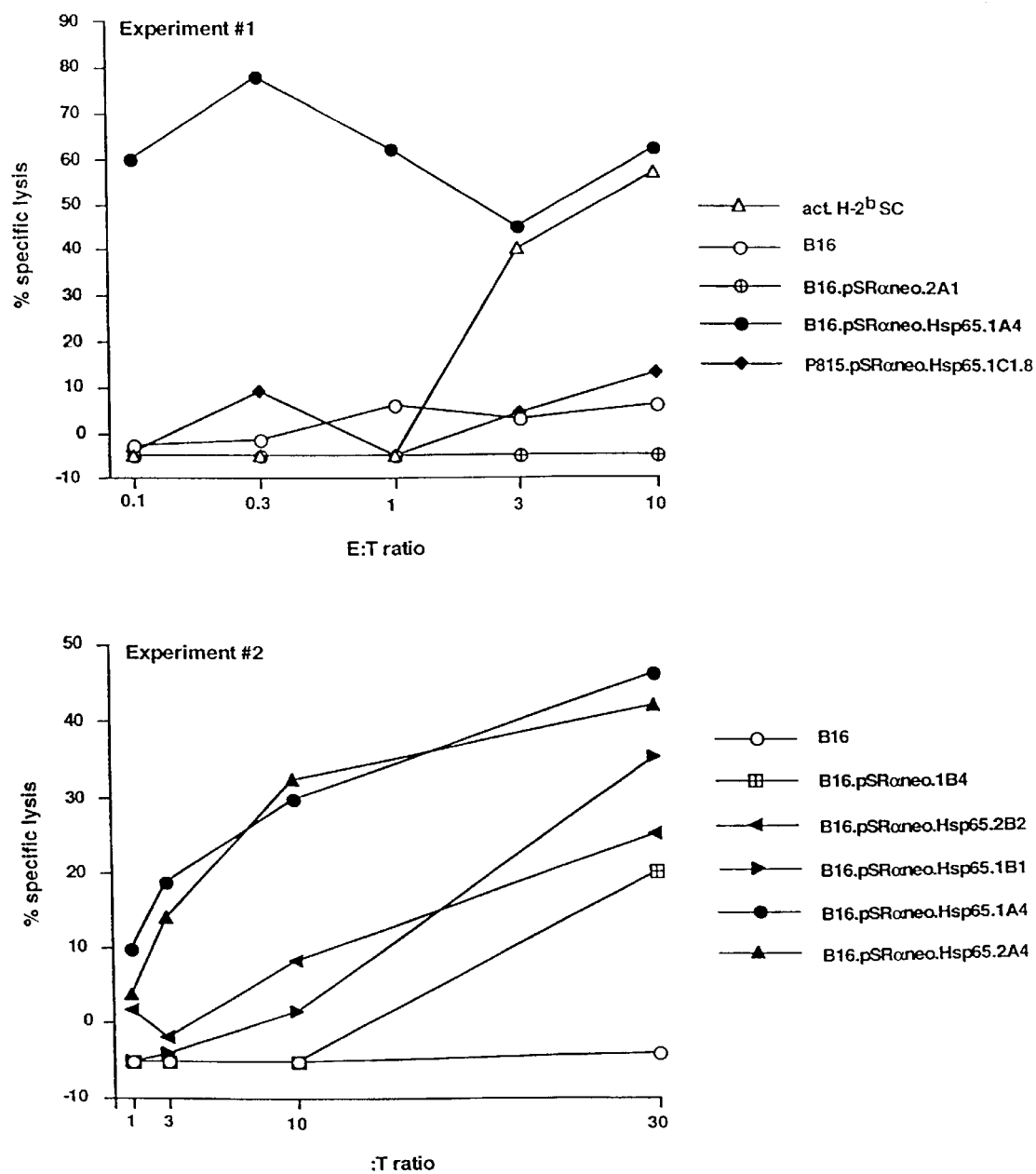
FIG. 14(B) is a graph of the cytolytic activity obtained from two separate experiments (upper and lower panel) in which the cytolytic activity of two separate allospecific CTL populations was measured against B16, B16.pSRαneo, B16.pSRαneo, Hsp65, LPS-activated H-2$^b$ splenocytes and P815.pSRαneo.Hsp65 targets.

FIG. 14B depicts two representative experiments in which the cytolytic activity of two separate allospecific CTL populations was measured against B16, B16.pSRαneo, B16.pSRαneo.Hsp65, LPS-activated H-$2^b$ splenocytes and P815.pSRαneo.Hsp65 targets. Neither B16 (open circles) nor B16.pSRαneo (crossed circles) were lysed efficiently by allospecific CTL (experiment #1, upper panel). A clone of P815.pSRαneo.Hsp65 (H-$2^d$) (closed diamonds) was also not lysed. B16.pSRαneo.Hsp65 clone 1A4 (closed circles) was lysed to a high degree and with high efficiency as compared to LPS-activated H-$2^b$ splenocytes (open triangles). In a separate experiment with CTL effectors obtained from a different MLR (experiment #2, lower panel), three B16.pSRαneo.Hsp65 clones in addition to 1A4 (2A4, 1B1 and 2B2) were tested for their susceptibility to allospecific CTL-mediated cytotoxicity. Clones 1A4 (closed circles) and 2A4 (closed vertical triangles) were lysed efficiently. Clones 1B1 and 2B2 (closed horizontal triangles) showed an intermediate level of lysis as compared to 1A4 and 2A4, but were consistently lysed with greater efficiency than B16.pSRαneo clones. The susceptibility of B16.pSRαneo.Hsp65 clones to allospecific CTL lysis appears to correlate with the quantity of MHC class I expressed, in that clones 1A4 and 2A4 express slightly higher levels of surface MHC class I antigen than do clones 2B2 and 1B1.

The results in FIG. 14B show that CTL specific for the H-$2^b$ haplotype of MHC class I were not able to effectively recognize either parent B16 cells (H-$2^b$) or control-transfected B16 clones (FIG. 14B). However, B16 clones which express Hsp65 were lysed efficiently (FIG. 14B). As with the anti-H-$2^b$ effectors, the enhanced lysis of the Hsp65-expressing clones was MHC-restricted, because P815 (H-$2^d$) cells expressing Hsp65 were not lysed.

Figure 15A:
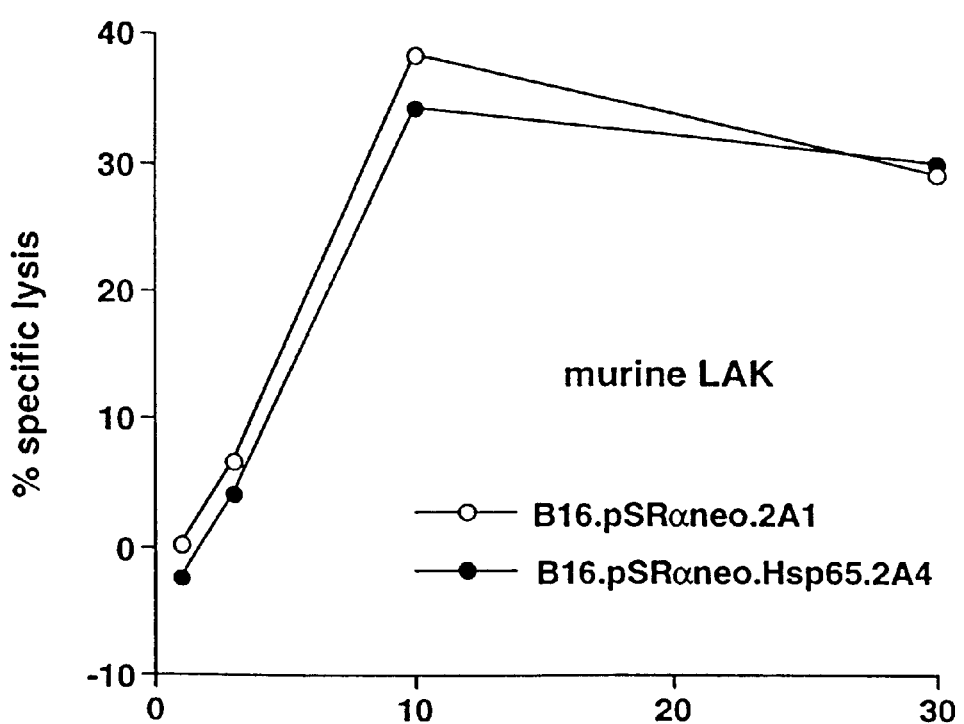
FIG. 15 shows the results of murine (A and C) and human (B) LAK cell-mediated cytotoxicity assay.
Figure 15B:
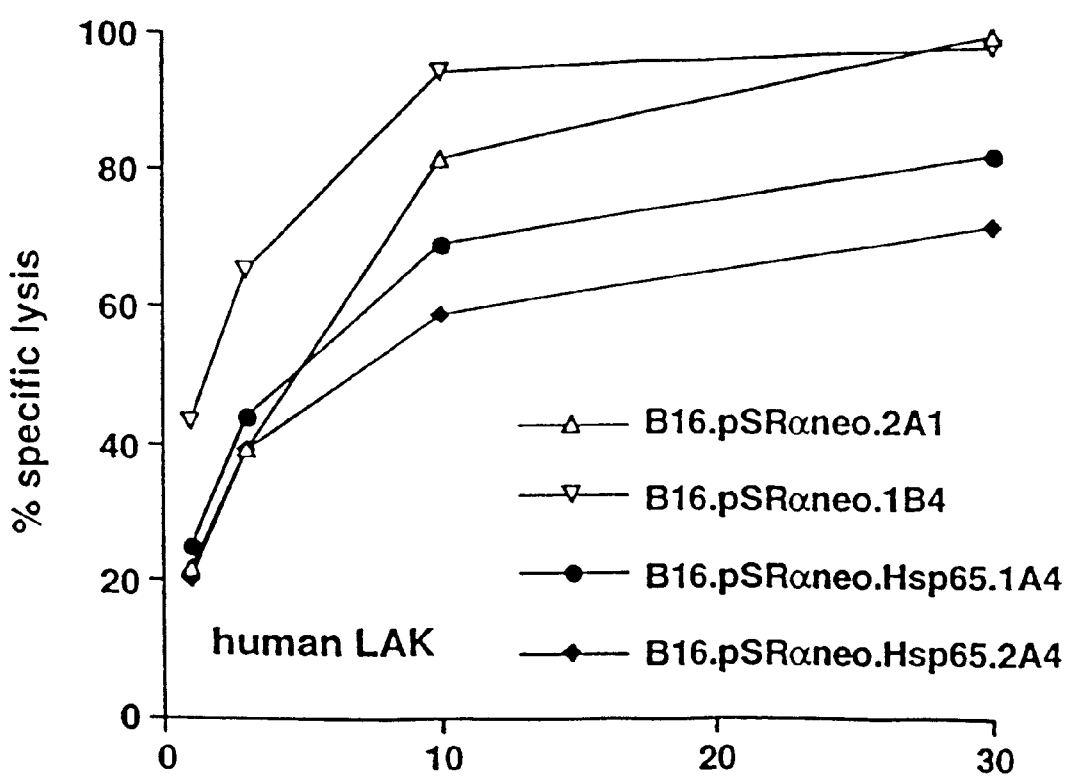
Figure 15C:
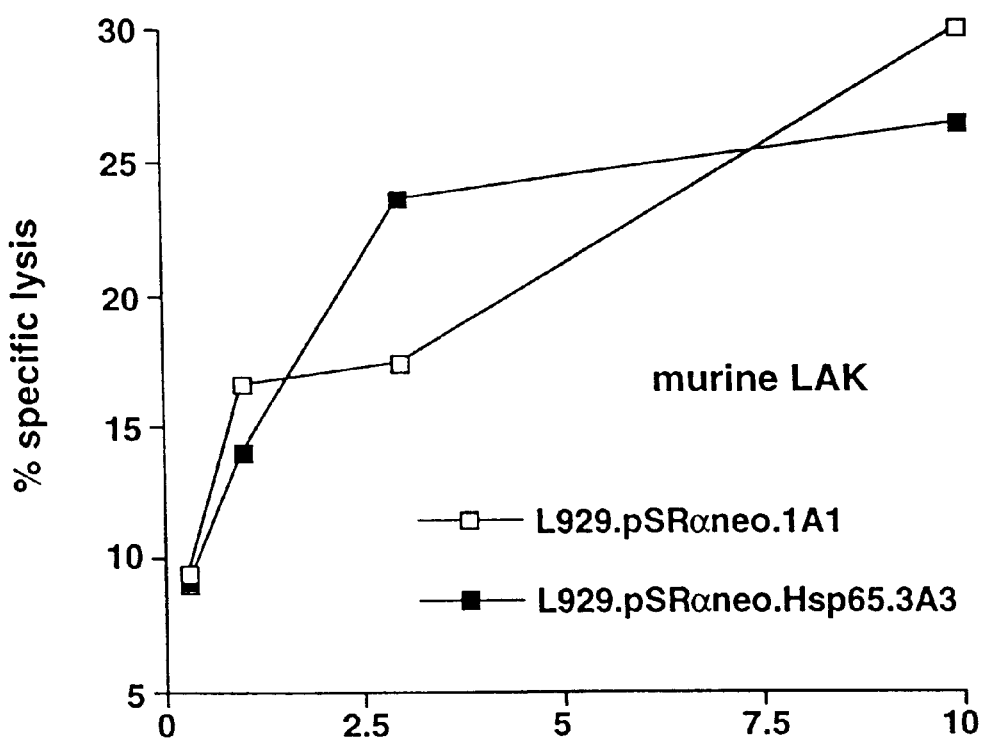

The possibility that the expression of Hsp65 merely made the cells more susceptible to lysis by cytotoxic effector mechanisms is unlikely, because lymphokine-activated killer (LAK) cells lysed the Hsp65-expressing clones as, or slightly less, efficiently than control clones (FIG. 15). FIG. 15 shows that B16.pSRαneo.Hsp65 clones (closed symbols) were no more susceptible to non-specific, murine (FIG. 15A) or human (FIG. 15B) LAK cell-mediated cytotoxicity than are control clones (open symbols). FIG. 15C shows that expression of Hsp65 in L929 (closed squares) does not affect the sensitivity of these cells to LAK cell-mediated cytotoxicity as compared to control clones (open squares). These observations are compatible with the known role of surface MHC class I molecules on target cells in downregulating LAK cell cytotoxicity [Chen et al. (1992) Cell 71:1093–1102].

Example 8

Enhanced Immunogenicity of Hsp65 Expressing Tumor Cells In Vivo

The capacity of Hsp65-expressing P815 and B16 cells to immunize mice against a subsequent challenge with parental, wild type tumor cells, which do not express Hsp65, was assessed using a transplantation/rejection model in which mice were immunized in vivo with Hsp65-expressing tumor cells or with inactivated tumor cells, followed by subsequent challenge with wild-type tumor cells followed by measurement of tumor incidence. This model was selected since rejection of wild type challenge tumor would show that T cell responses are effectively generated against endogenous tumor-associated antigens during immunization, not against the heat shock protein itself.

Prior to using the transplantation/rejection model, the tumorigenicity of Hsp65-expressing cells was determined. Expression of Hsp65 did not affect the tumorigenicity of either B16 or P815 in either immunocompetent or nude mice (data not shown). These results are in contrast to those of Lukacs et al. (1993) J. Exp. Med., 178: 343–348, who observed a complete abrogation of tumiongenicity in the monocytic tumor cell line J774 upon stable transfection with mycobacterial Hsp65.

In vivo immunization and tumor rejection assays were carried out as follows. B16 and P815 transfectants to be used as immunogens were growth-inhibited by treatment with mitomycin C (25 μg/ml for 3 hours; Boehringer Mannheim), harvested in PBS containing 1 mM EDTA (for B16), and washed in PBS. Mitomycin C-treated tumor cell suspensions were then γ-irradiated (5000 rad), washed in PBS, and resuspended at $5 \times 10^6$ cells per 0.2 ml PBS. At days 0 and 10 of each experiment, C57BL/6 (Harlan Sprague-Dawley, Madison, Wis.) aged between 6–10 weeks, or DBA/2 mice (Harlan Sprague-Dawley, Madison, Wis.) aged between 6–10 weeks (4–5 per group) were injected either intraperitoneal or subcutaneously with 0.2 ml PBS, or with inactivated tumor cell suspensions ($5 \times 10^6$ cells) in 0.2 ml PBS. Immunized mice were then challenged on day 20 by subcutaneous injection of $2 \times 10^4$ wild type tumor cells (viability >98%) suspended in 0.1 ml PBS. The 50% tumorigenic dose of the B16 and P815 tumor cells used in these studies was determined to be approximately $10^3$ and $2 \times 10^3$ cells, respectively. Doses of $5 \times 10^3$, $10^4$ and $2 \times 10^4$ cells lead to progressively growing tumors in 100% of naive mice challenged subcutaneously. Incidence of the challenge tumor was assessed by palpation of the challenged flank, and was scored as positive on the day that the established tumor reached 25 mm² as measured by tissue calipers. Mice were sacrificed before challenge tumors reached 500 mm², or if mice developed ascites from the immunizing tumor cell dose. The results are shown in FIG. 16.

Figure 16C:
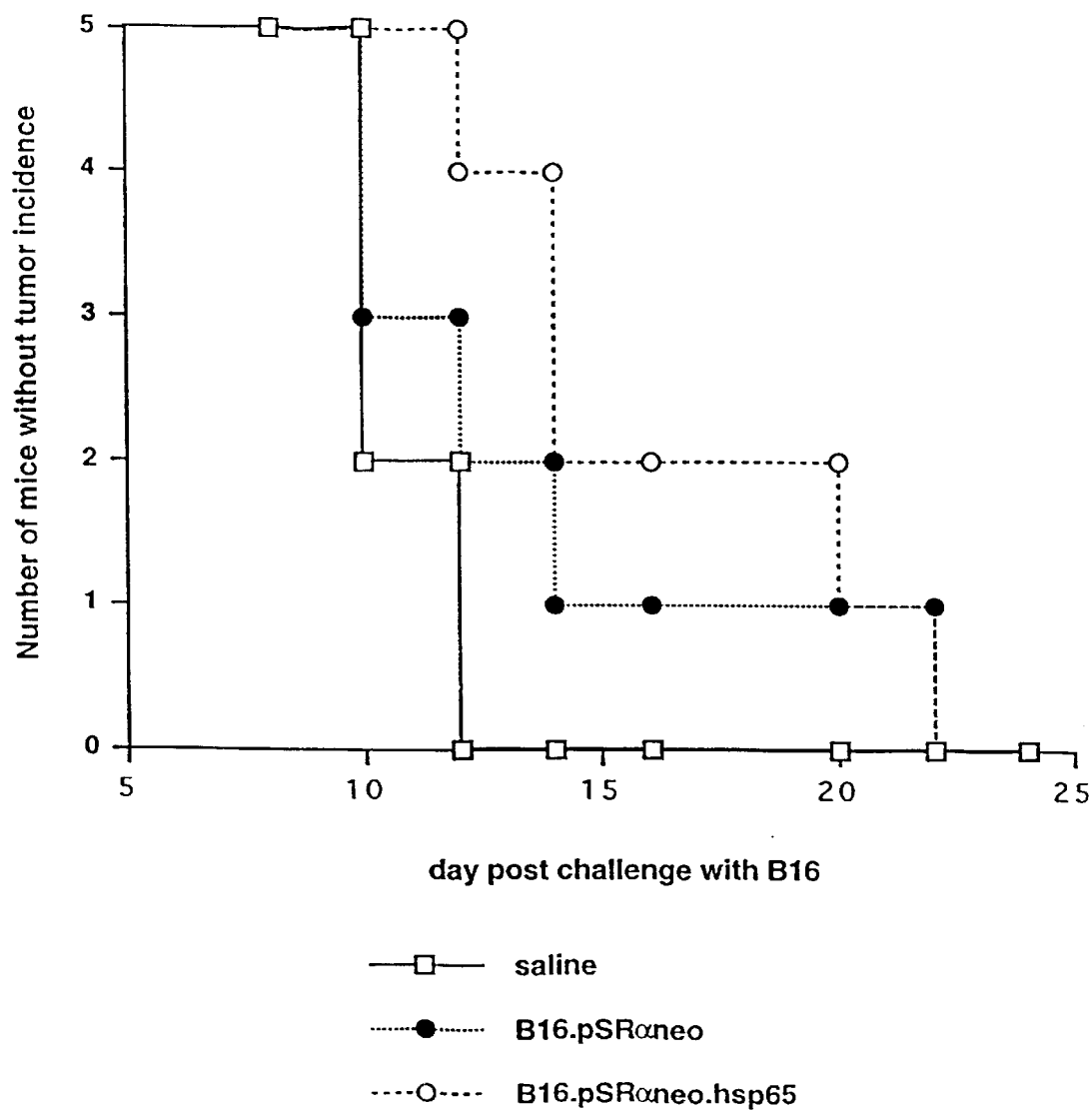
Figure 16D:
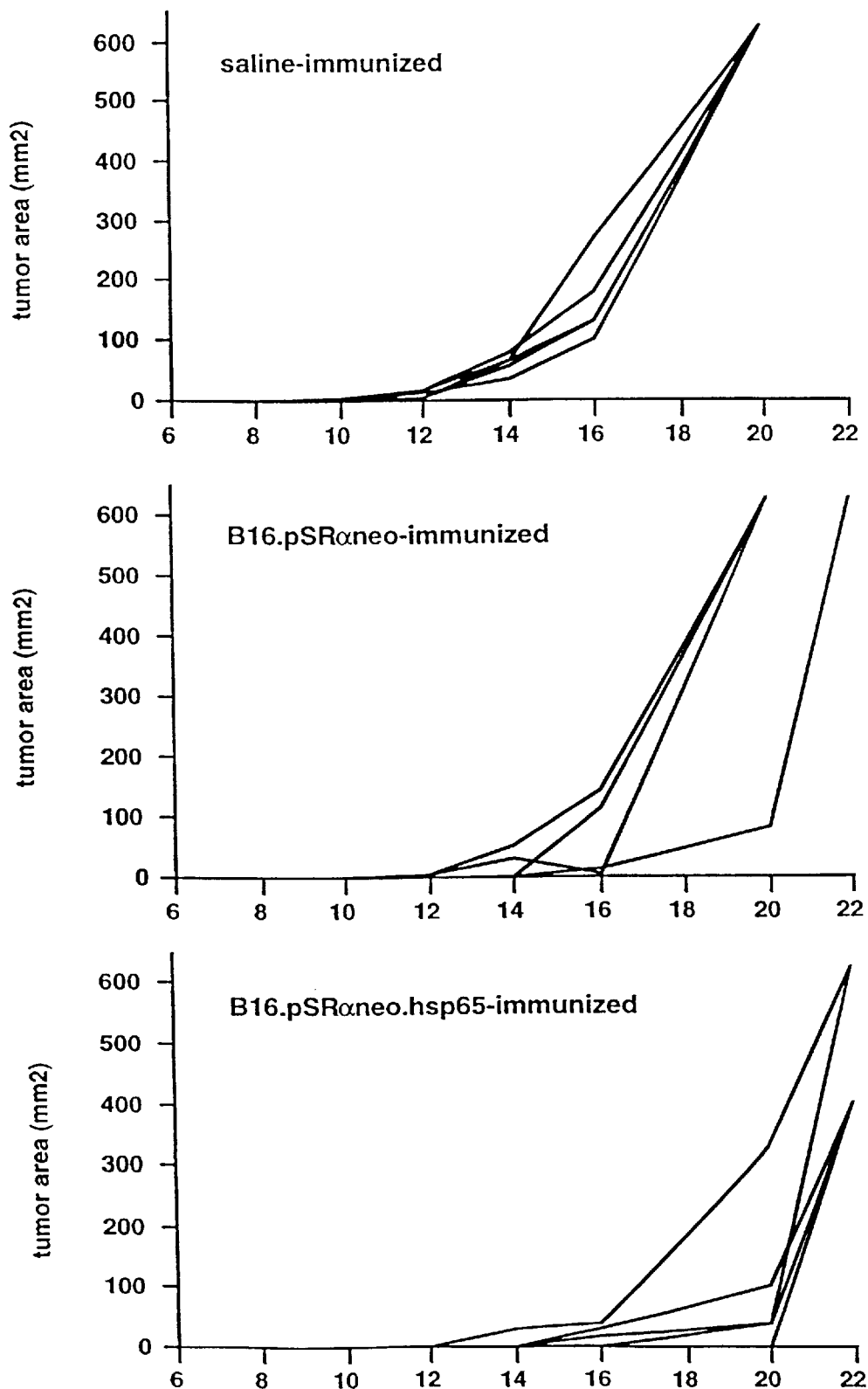

FIG. 16(A) tumor incidence in syngeneic DBA/2 (H-2$^d$) mice immunized intraperitoneal with either saline (open squares), P815.pSRαneo cells (closed circles) or P815.pSRαneo.Hsp65 cells (open circles), followed by subcutaneous challenge with live, wild type P815. FIG. 16(B) shows the tumor incidence in syngeneic C57BL/6 (H-2$^b$) mice immunized intraperitoneal with either saline (open squares), B16.pSRαneo cells (closed circles) or B16.pSRαneo.Hsp65 cells (open circles), followed by subcutaneous challenge with live, wild type B16. Two separate experiments for each tumor are shown. All mice which scored positive for incidence went on to develop progressively-growing challenge tumors. The tumor incidence exhibited by mice immunized with P815.pSRαneo.Hsp65 or B16.pSRαneo.Hsp65 compared to mice immunized with either saline or pSRαneo controls are significantly different as measured by Log-Rank test ($p<0.05$ for all experiments shown). FIG. 16C shows the tumor incidence in syngeneic C57BL/6 (H-2$^b$) mice immunized subcutaneously with either saline (open squares), B16.pSRαneo cells (closed circles) or B16.pSRαneo.Hsp65 cells (open circles), followed by subcutaneous challenge with live, wild type B16. FIG. 16D shows the growth kinetics of wild type challenge tumors in the mice depicted in FIG. 16C. Each line represents the tumor growth in an individual mouse.

The results in FIG. 16 show that whereas pre-exposure of mice to control-transfected tumor cells did not afford protection against challenge with wild type tumors as compared to treatment with PBS alone, mice immunized with Hsp65-expressing tumor cells were significantly more resistant to wild type tumor challenge. Additionally, the route of immunization was important, as intraperitoneal (FIGS. 16A and BE), but not subcutaneous (FIGS. 16C and 16D) immunization induced significant resistance to tumor challenge.

The above data demonstrate that expression of Hsp65 can enhance the capacity of tumor cells to present alloantigens and viral antigens to MHC class I-restricted CTL in vitro. Hsp65 may function similarly to enhance the presentation of endogenous tumor-associated antigens in vivo, as suggested by the capacity of Hsp65-expressing tumor cells, but not control-transfected cells, to induce an immune response capable of recognizing and rejecting wild type tumors, which do not express Hsp65. This immunity was systemic, as mice immunized intraperitoneal were able to reject a subcutaneous tumor challenge at a distant site. Furthermore, exposure of these Hsp-expressing tumor cells to very high doses of ionizing radiation (>10,000 rad) reduced or abrogated their immunogenicity in vivo (not shown). This suggests that the protective effect is dependent on the antigen presentation capacity of the tumor cells themselves, and not on the function of host APC which have phagocytized and presented antigens released by dying tumor cells.

Whereas pre-exposure of mice to control-transfected tumor cells did not afford protection against challenge with wild type tumors as compared to treatment with PBS alone, mice immunized with Hsp65-expressing tumor cells were significantly more resistant to wild type tumor challenge (FIG. 16). The route of immunization was important, as intraperitoneal (FIGS. 16A and B), but not subcutaneous (FIGS. 16C and D) immunization induced significant resistance to tumor challenge.

Example 9

Enhanced In Vitro Radioresistance of Hsp65-Expressing Tumor Cells

The B16 melanoma is a relatively radiation-resistant murine tumor cell. During investigation of the effects of heat shock protein expression on the tumorigenicity and immunogenicity of B16 in mice, it was observed that Hsp65-expressing B16 clones were refractory to growth inhibition after treatment with ionizing radiation. Mice injected with irradiated Hsp65-expressing B16 clones consistently suffered an increased incidence of "breakthrough" tumors than mice injected with irradiated control or parent B16 clones. This phenomenon was further investigated in vitro in order to determine the effect of Hsp65 expression on short term and long term survival of tumor cells subjected to ionizing radiation.

A. Conditions for Exposure to Ionizing Radiation

Control and Hsp65-expressing B16 transfectants generated and characterized as described in chapter 2 of this dissertation were harvested, and cell suspensions were subjected either to doses of ionizing radiation ranging from 500 to 10,000 rad using a Cs-137 source, or to mitomycin C (2 hours, 50 µg/ml). Mitomycin is a drug which inhibits cell division by inducing detachment of chromosomes from mitotic spindles. Irradiated cells were then washed once in serum-free medium and plated in 96-well culture plates at 1000 cells per well. Cultures were pulsed at various time points for 18 hours with H-3 thymidine ($^3$H-TdR, 1 µCi per well) and cell lysates were harvested onto glass fiber filter mats for subsequent determination of $^3$H-TdR incorporation. Cell monolayers were also monitored microscopically for their general appearance.

Figure 17A:
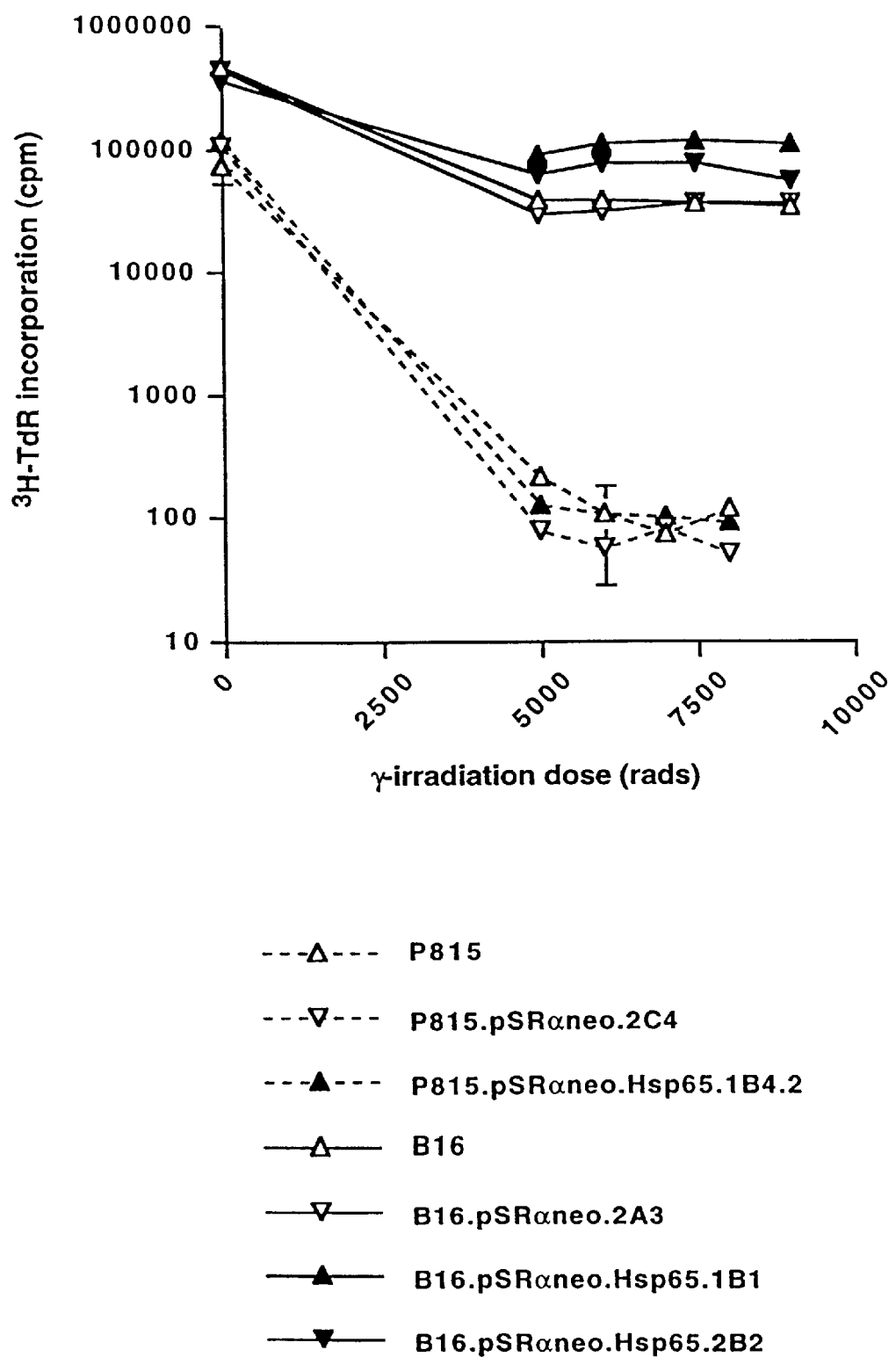
FIGS. 17A–C show (A) $^3$H-TdR incorporation of B16 and P815 tumor transfectants, $^3$H-TdR incorporation of B16 tumor cells two days post-irradiation (B) and four days post-irradiation (C), and the relative decrease in $^3$H-TdR incorporation of B16 transfectants (D).
Figure 17B:
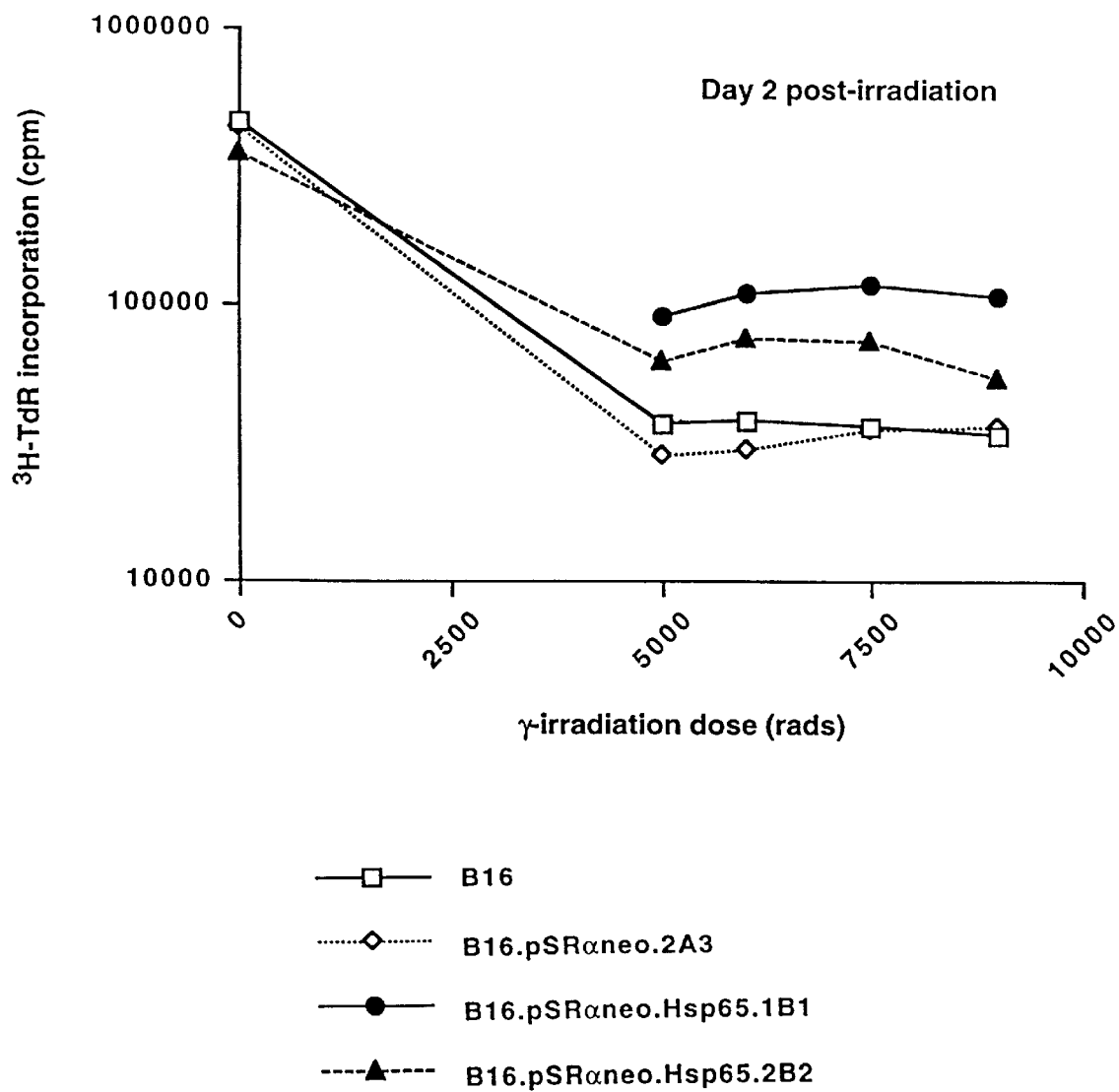
Figure 17C:
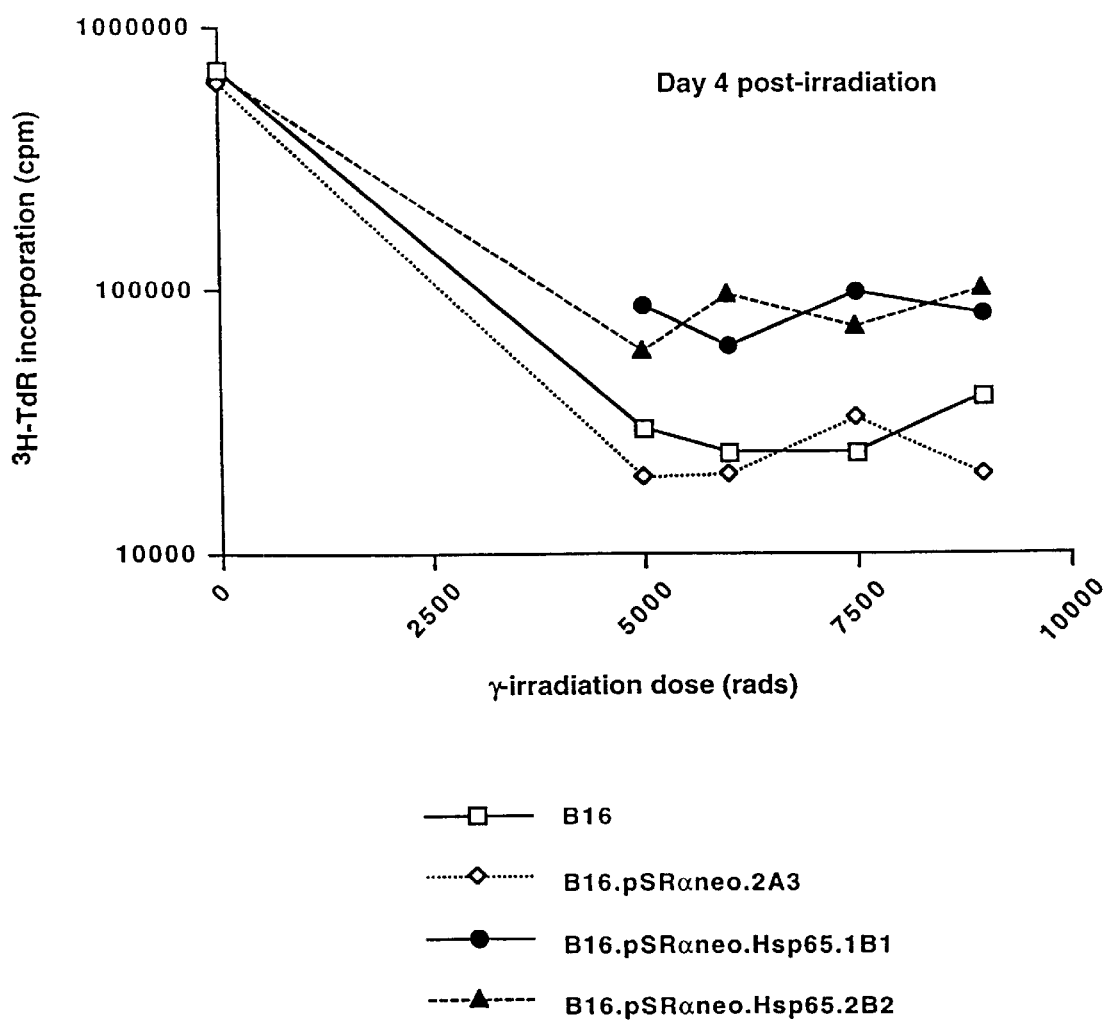
Figure 17D:
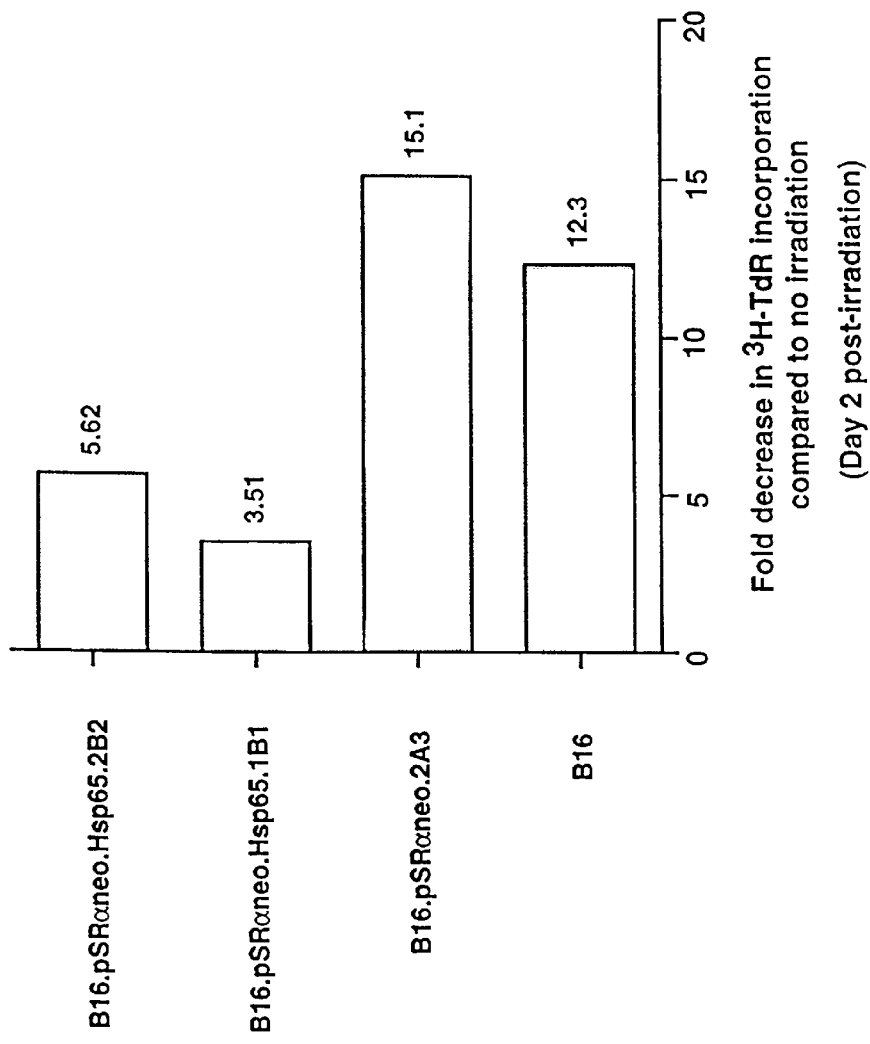

B. Expression of Hsp65 Enhances Short Term Survival and Long Term Recovery of B16 Cells Following Low Doses of Ionizing Radiation FIG. 17A shows $^3$H-TdR incorporation of B16 and P815 tumor transfectants after no treatment (0 rad), or following treatment with doses of ionizing (γ) radiation ranging from 5000 to 8000 rad. Parent tumor cell lines (open triangles), control-transfected tumor cell clones (open inverted triangles) and Hsp65-expressing tumor cell clones (closed triangles) were irradiated as cell suspensions. FIG. 17B and C shows $^3$H-TdR incorporation of B16 tumor cells (open squares), control B16 transfectants (open diamonds) and two separate Hsp65-expressing B16 clones (closed symbols) was monitored two days post-irradiation (FIG. 17B) and four days post-irradiation (FIG. 17C). The relative decrease in the $^3$H-TdR incorporation of B16 transfectants exposed to 7500 rad as compared to the same clones receiving 0 rad is shown in FIG. 17D.

Parental B16 melanoma cells suffered approximately a 15-fold decrease in $^3$H-TdR incorporation two days following doses of ionizing radiation ranging from 5000 to 8000 rad, whereas P815 cells suffered approximately a 1000-fold decrease in $^3$H-TdR incorporation after irradiation at these same doses (FIG. 17A). The expression of Hsp65 had no effect on the radiation sensitivity of P815 as measured by $^3$H-TdR incorporation, however, Hsp65-expressing B16 clones did exhibit an enhanced level of $^3$H-TdR incorporation at both two days (FIG. 17B) and four days (FIG. 17C) following irradiation. B16.pSRαneo.Hsp65 clones 1B1 and 2B2 suffered only a 5.6-fold and 3.5-fold decrease, respectively, in $^3$H-TdR incorporation two days following a 7500 rad dose of irradiation, as compared clones receiving no irradiation, whereas the parental B16 line and the B16.pSRαneo clone suffered a 12.3-fold and 15.1-fold decrease in $^3$H-TdR incorporation (FIG. 17D). In a separate experiment, B16.pSRαneo and B16.pSRαneo.Hsp65 clones were subjected to doses of radiation ranging from 500 to 10,000 rad, and $^3$H-TdR incorporation was measured after two and six days and expressed as a percentage of the $^3$H-TdR incorporation exhibited by corresponding clones which received no radiation treatment.

Figure 18A:
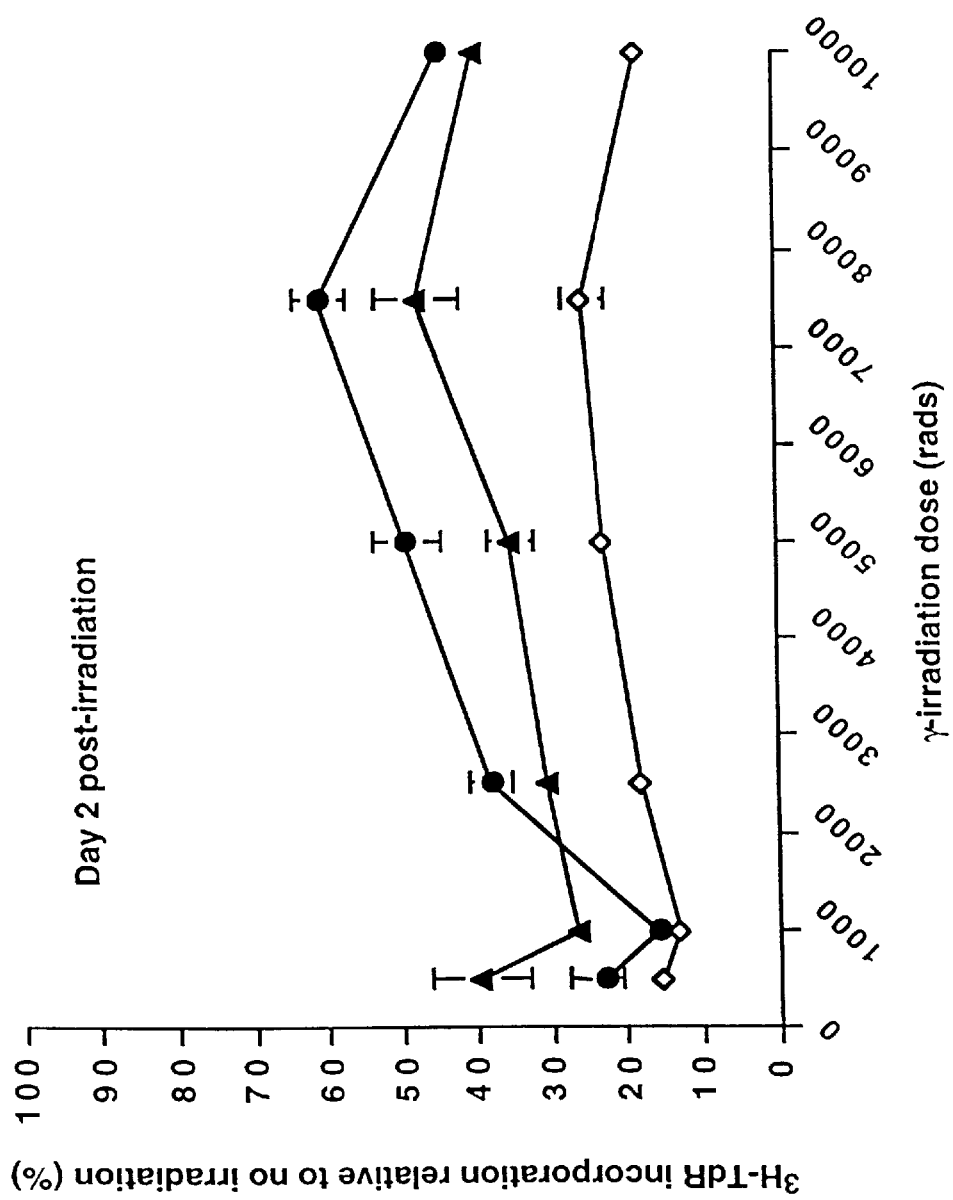
FIG. 18 shows $^3$H-TdR incorporation at day 2 (A) and day 6 (B) post-irradiation.
Figure 18B:
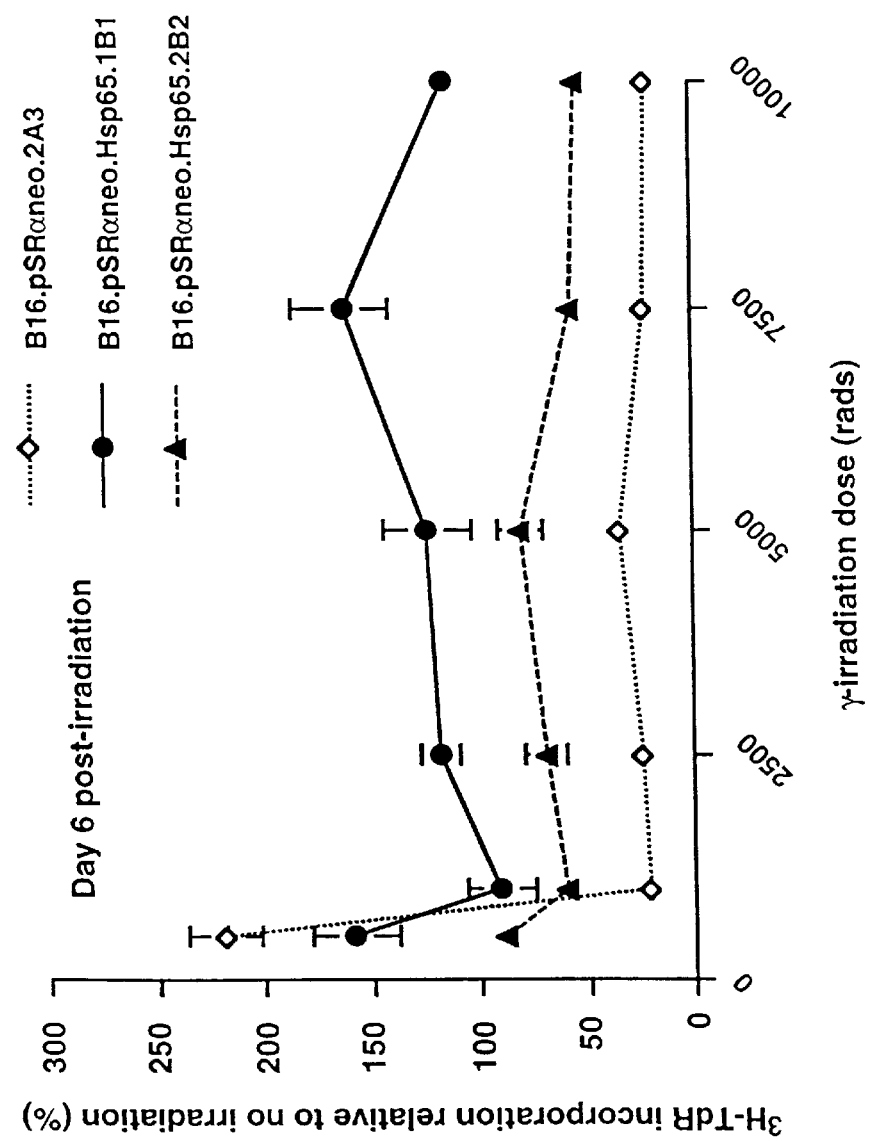

FIG. 18 shows the short term versus long term effects on the $^3$H-TdR incorporation of a control B16 transfectant (open diamonds) and two Hsp65-expressing B16 clones (closed symbols) exposed to doses of ionizing radiation ranging from 500 to 10,000 rad. $^3$H-TdR incorporation was measured at day 2 (FIG. 18A) and day 6 (FIG. 18B) post-irradiation, and values are expressed as the incorporation of irradiated clones relative to the same clones receiving 0 rad.

Expression of Hsp65 appeared to enhance the short term (two days post-irradiation) resistance of cells subjected to low dose (500 rad) irradiation (FIG. 18A), however, this effect was no longer seen by day six post-irradiation, as B16.pSRαneo cells had recovered and entered a phase of strong $^3$H-TdR incorporation (FIG. 18B). At doses of ionizing radiation in excess of 1000 rad, Hsp65 expressing clones exhibited a 3- to 6-fold increase in radiation resistance at both timepoints compared to the control clone, which incorporated $^3$H-TdR at below 20% of the untreated control (FIGS. 18A and B). Furthermore, B16.pSRαneo.Hsp65 clone 1B1 was consistently more resistant to the effects of ionizing radiation than clone 2B2 (FIGS. 18A and B).

Figure 19A:
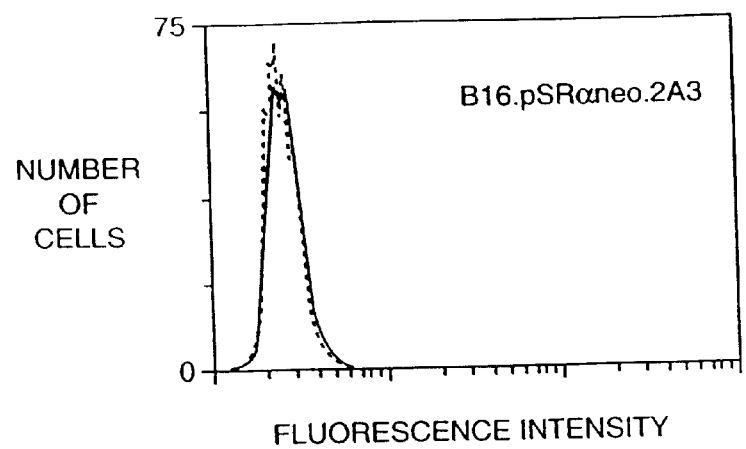
FIGS. 19A–19C show histograms for the quantitation of Hsp65 expression by B16 transfectants.
Figure 19B:
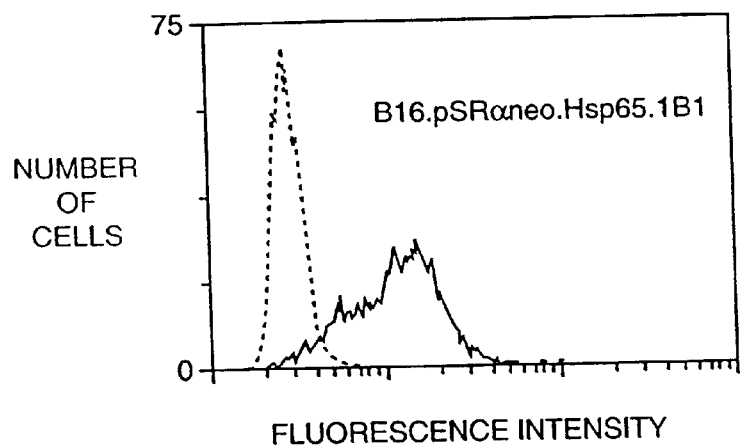
Figure 19C:
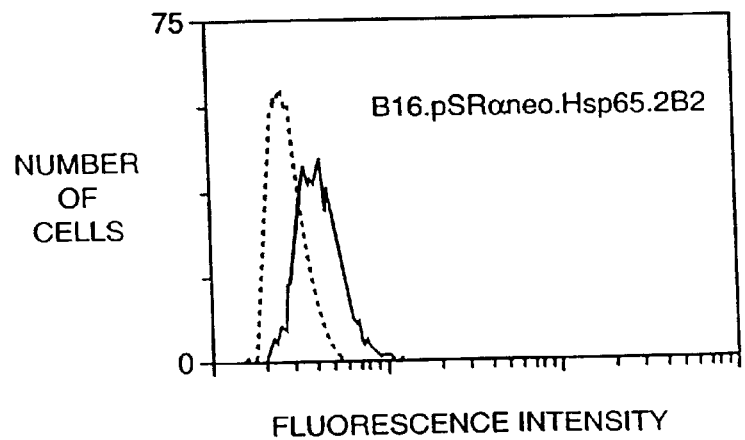

FIGS. 19A–19C the quantitation of Hsp65 expression by B16 transfectants. Histograms represent the mean fluorescence intensity of permeabilized cells stained with either isotype control antibody (dotted gray lines) or mc4220 (solid black lines), followed by FITC-conjugated secondary antibody. Interestingly, clone 1B1 was shown to express approximately four-fold more Hsp65 than clone 2B2 (FIGS. 19A–19C), suggesting that the radiation-protective effect of Hsp65 was dose-dependent.

Figure 20:
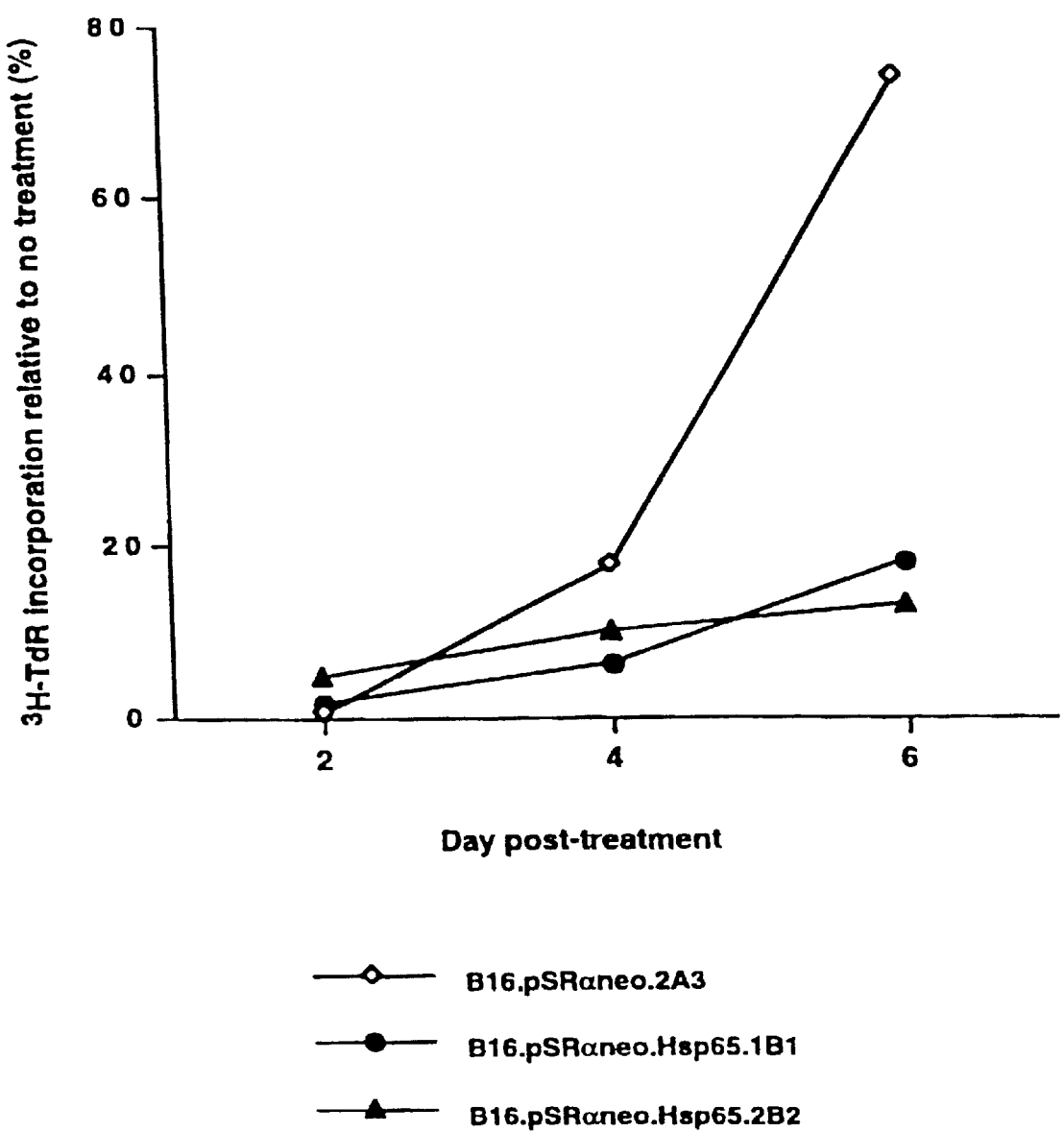
FIG. 20 shows relative $^3$H-TdR incorporation of a B16 control transfectant (open diamonds) and two Hsp65-expressing B16 clones (closed symbols) following mitomycin C treatment.

FIG. 20 shows the relative $^3$H-TdR incorporation of a B16 control transfectant (open diamonds) and two Hsp65-expressing B16 clones (closed symbols) following mitomycin C treatment. The results in FIG. 20 show that the protective effect of Hsp65 expression appeared to be selective for the growth-inhibiting effects of radiation, as opposed to the inhibition of cell division in general, as Hsp65-expressing B16 clones were not resistant (and in fact were more susceptible) to treatment with mitomycin C, a drug which inhibits cell division by inducing detachment of chromosomes from mitotic spindles.

In the above these experiments, $^3$H-TdR incorporation most likely represents DNA synthesis resulting from cell proliferation, rather than from DNA repair. Indeed, by empirical observation of monolayers, irradiated Hsp65-expressing clones showed a definite increase in healthy, adherent cell mass over time in culture, whereas monolayers derived from irradiated control cells did not become confluent, and a significant amount of dead, lifted cells could be observed beginning five days after culture (data not shown).

These results demonstrate that expression of Hsp65 enhances both the short term survival of B16 cells subjected to relatively low doses of ionizing radiation, as well as the long term recovery of B16 cells subjected to doses of ionizing radiation as high as 10,000 rad. This suggests that expression of Hsp65 in, e.g., stem cells, may increase the tolerance of these cells to therapeutic doses of radiation, while inhibition of the expression of Hsp65 in radioresistant tumors may increase the radiosensitivity of these tumors, thus increasing the probability of selective killing of tumor cells as compared to normal cells.

It is clear from the above that the methods of the present invention provide effective means for increasing the immunogenicity of any cell or antigen, thus enhancing the generation of antibodies to an otherwise poorly immunogenic antigen or poorly immunogenic cell and ultimately offering candidate approaches to immunogene therapy in non-human animals and in human patients. It is also clear that the methods provided herein further furnish approaches to reduce or increase the radiation sensitivity of a cell, thus improving the prognosis of patients treated with ionizing radiation therapy.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

What is claimed is:

1. A method of specifically increasing expression of an MHC class I molecule in an isolated target cell, comprising:
   a) providing:
      i) said isolated target cell, wherein said cell is infected with a pathogen that is processed by the MHC class I endogenous pathway; and
      ii) an expression vector encoding a heat shock protein; and
   b) introducing said expression vector into said target cell under conditions such that said heat shock protein is expressed and a transfected cell is produced having increased expression of at least one MHC class I molecule.

2. The method of claim 1, further comprising step c) detecting said increase in expression of said MHC class I molecule in said transfected cell compared to said target cell.

3. The method of claim 1, wherein said heat shock protein is a member of a heat shock protein family selected from the group consisting of Hsp 27 family, Hsp 60 family, Hsp 70 family and Hsp 90 family.

4. The method of claim 1, wherein said pathogen is a virus.

5. The method of claim 4, wherein said virus is lymphocytic choriomeningitis virus.

6. The method of claim 2, wherein said target cell is murine and said MHC class I molecule detected is selected from the group consisting of murine H-2K and murine H-2D.

7. The method of claim 2, wherein said target cell is human and said MHC class I molecule detected is selected from the group consisting of human HLA-A, human HLA-B and human HLA-C.

8. A method of increasing presentation of an antigen on a cell surface by an MHC class I molecule, comprising:
   a) providing:
      i) a target cell in vitro, said target cell expressing said antigen and having a target cell surface, wherein said antigen is processed by the MHC class I endogenous pathway;
      ii) an expression vector encoding a heat shock protein;
   b) introducing said expression vector into said target cell under conditions such that said heat shock protein is expressed and a transfected cell is produced having increased presentation of said antigen on said cell surface by at least one MHC class I molecule; and
   c) detecting said increased level of presentation on said target cell surface.

9. The method of claim 8, wherein said heat shock protein is a member of a heat shock protein family selected from the group consisting of Hsp 27 family, Hsp 60 family, Hsp 70 family and Hsp 90 family.

10. The method of claim 8, wherein said antigen is derived from a pathogen selected from the group consisting of virus and bacteria.

11. The method of claim 10, wherein said pathogen is a virus.

12. The method of claim 11, wherein said virus is lymphocytic choriomeningitis virus.

13. The method of claim 8, wherein said target cell is murine and said MHC class I molecule detected in step c) is selected from the group consisting of murine H-2K and murine H-2D.

14. The method of claim 8, wherein said target cell is human and said MHC class I molecule detected in step c) is selected from the group consisting of human HLA-A, human HLA-B and human HLA-C.

* * * * *

SEQUENCE LISTING

<160> NUMBER OF SEQ ID NOS: 6

<210> SEQ ID NO 1
<211> LENGTH: 2691
<212> TYPE: DNA
<213> ORGANISM: Homo sapiens

<400> SEQUENCE: 1

```
cgccatggag accaacaccc ttcccaccgc cactcccct tcctctcagg gtccctgtcc      60
cctccagtga atcccagaag actctggaga gttctgagca gggggcggca ctctggcctc     120
```

-continued

| | |
|---|---|
| tgattggtcc aaggaaggct gggggggcagg acgggaggcg aaaccctgg aatattcccg | 180 |
| acctggcagc ctcatcgagc tcggtgattg gctcagaagg gaaaaggcgg gtctccgtga | 240 |
| cgacttataa aagcccaggg gcaagcggtc cggataacgg ctagcctgag gagctgctgc | 300 |
| gacagtccac tacctttttc gagagtgact cccgttgtcc caaggcttcc cagagcgaac | 360 |
| ctgtgcggct gcaggcaccg gcgcgtcgag tttccggcgt ccggaaggac cgagctcttc | 420 |
| tcgcggatcc agtgttccgt ttccagcccc caatctcaga gccgagccga cagagagcag | 480 |
| ggaaccgcat ggccaaagcc gcggcagtcg gcatcgacct gggcaccacc tactcctgcg | 540 |
| tgggggtgtt ccaacacggc aaggtggaga tcatcgccaa cgaccagggc aaccgcacca | 600 |
| cccccagcta cgtggccttc acggacaccg agcggctcat cggggatgcg gccaagaacc | 660 |
| aggtggcgct gaacccgcag aacaccgtgt tgacgcgaa gcgcctgatc ggccgcaagt | 720 |
| tcggcgaccc ggtggtgcag tcggacatga agcactggcc tttccaggtg atcaacgacg | 780 |
| gagacaagcc caaggtgcag gtgagctaca aggggggagac caaggcattc taccccgagg | 840 |
| agatctcgtc catggtgctg accaagatga aggagatcgc cgaggcgtac ctgggctacc | 900 |
| cggtgaccaa cgcggtgatc accgtgccgg cctacttcaa cgactcgcag cgccaggcca | 960 |
| ccaaggatgc gggtgtgatc gcggggctca acgtgctgcg gatcatcaac gagcccacgg | 1020 |
| ccgccgccat cgcctacggc ctggacagaa cgggcaaggg ggagcgcaac gtcctgatct | 1080 |
| ttgacctggg cggggggcacc ttcgacgtgt ccatcctgac gatcgacgac ggcatcttcg | 1140 |
| aggtgaaggc cacggccggg gacacccacc tgggtgggga ggactttgac aacaggctgg | 1200 |
| tgaaccactt cgtggaggag ttcaagagaa aacacaagaa ggacatcagc cagaacaagc | 1260 |
| gagccgtgag gcggctgcgc accgcctgcg agagggccaa gaggaccctg tcgtccagca | 1320 |
| cccaggccag cctggagatc gactccctgt tgagggcat cgacttctac acgtccatca | 1380 |
| ccagggcgag gttcgaggag ctgtgctccg acctgttccg aagcaccctg gagcccgtgg | 1440 |
| agaaggctct gcgcgacgcc aagctggaca aggcccagat tcacgacctg gtcctggtcg | 1500 |
| ggggctccac ccgcatcccc aaggtgcaga agctgctgca ggacttcttc aacgggcgcg | 1560 |
| acctgaacaa gagcatcaac cccgacgagg ctgtgggcta cggggcggcg gtgcaggcgg | 1620 |
| ccatcctgat gggggacaag tccgagaacg tgcaggacct gctgctgctg gacgtggctc | 1680 |
| ccctgtcgct ggggctggag acggccggag gcgtgatgac tgccctgatc aagcgcaact | 1740 |
| ccaccatccc caccaagcag acgcagatct tcaccaccta ctccgacaac caacccgggg | 1800 |
| tgctgatcca ggtgtacgag ggcgagaggg ccatgacgaa agacaacaat ctgttggggc | 1860 |
| gcttcgagct gagcggcatc cctccggccc caggcgtgcc ccagatcgag gtgaccttcg | 1920 |
| acatcgatgc caacggcatc ctgaacgtca cggccacgga caagagcacc ggcaaggcca | 1980 |
| acaagatcac catcaccaac gacaagggcc gcctgagcaa ggaggagatc gagcgcatgg | 2040 |
| tgcaggaggc ggagaagtac aaagcggagg acgaggtgca gcgcgagagg gtgtcagcca | 2100 |
| agaacgccct ggagtcctac gccttcaaca tgaagagcgc cgtggaggat gaggggctca | 2160 |
| agggcaagat cagcgaggcc gacaagaaga aggtgctgga caagtgtcaa gaggtcatct | 2220 |
| cgtggctgga cgccaacacc ttggccgaga aggacgagtt tgagcacaag aggaaggagc | 2280 |
| tggagcaggt gtgtaacccc atcatcagcg gactgtacca gggtgccggt ggtcccgggc | 2340 |
| ctggggggctt cggggctcag gtcccaaggg gagggtctgg gtcaggcccc accattgagg | 2400 |
| aggtagatta ggggccttc caagattgct gttttttgttt tggagcttca agactttgca | 2460 |
| tttcctagta tttctgtttg tcagttctca atttcctgtg tttgcaatgt tgaaattttt | 2520 |

-continued tggtgaagta ctgaacttgc cttttttttcc ggtttctaca tgcagagatg aatttatact 2580
gccatcttac gactatttct tctttttaat acacttaact caggccattt tttaagttgg 2640
ttacttcaaa gtaaataaac tttaaaattc aagtgatgcc cttttattcc t 2691

<210> SEQ ID NO 2
<211> LENGTH: 14
<212> TYPE: PRT
<213> ORGANISM: Artificial Sequence
<220> FEATURE:
<223> OTHER INFORMATION: Unknown

<400> SEQUENCE: 2

Gly Trp Thr Gly Ser Asp Gly Lys Thr Thr Trp Cys Ser Gln
1 5 10

<210> SEQ ID NO 3
<211> LENGTH: 4380
<212> TYPE: DNA
<213> ORGANISM: Mycobacterium tuberculosis

<400> SEQUENCE: 3
tcgaacgagg ggcgtgaccc ggtgcggggc ttcttgcact cggcataggc gagtgctaag 60
aataacgttg gcactcgcga ccggtgagtg ctaggtcggg acggtgaggc caggcccgtc 120
gtcgcagcga gtggcagcga ggacaacttg agccgtccgt cgcgggcact gcgcccggcc 180
agcgtaagta gcggggttgc cgtcacccgg tgaccccggt ttcatccccg atccggagga 240
atcacttcgc aatggccaag acaattgcgt acgacgaaga ggcccgtcgc ggcctcgagc 300
ggggcttgaa cgccctcgcc gatgcggtaa aggtgacatt gggccccaag ggccgcaacg 360
tcgtcctgga aaagaagtgg ggtgccccca cgatcaccaa cgatggtgtg tccatcgcca 420
aggagatcga gctggaggat ccgtacgaga agatcggcgc cgagctggtc aaagaggtag 480
ccaagaagac cgatgacgtc gccggtgacg gcaccacgac ggccaccgtg ctggcccagg 540
cgttggttcg cgagggcctg cgcaacgtcg cggccggcgc caacccgctc ggtctcaaac 600
gcggcatcga aaaggccgtg gagaaggtca ccgagaccct gctcaagggc gccaaggagg 660
tcgagaccaa ggagcagatt gcggccaccg cagcgatttc ggcgggtgac cagtccatcg 720
gtgacctgat cgccgaggcg atggacaagg tgggcaacga gggcgtcatc accgtcgagg 780
agtccaacac ctttgggctg cagctcgagc tcaccgaggg tatgcggttc gacaagggct 840
acatctcggg gtacttcgtg accgacccgg agcgtcagga ggcggtcctg gaggacccct 900
acatcctgct ggtcagctcc aaggtgtcca ctgtcaagga tctgctgccg ctgctcgaga 960
aggtcatcgg agccggtaag ccgctgctga tcatcgccga ggacgtcgag ggcgaggcgc 1020
tgtccaccct ggtcgtcaac aagatccgcg gcaccttcaa gtcggtggcg gtcaaggctc 1080
ccggcttcgg cgaccgccgc aaggcgatgc tgcaggatat ggccattctc accggtggtc 1140
aggtgatcag cgaagaggtc ggcctgacgc tggagaacgc cgacctgtcg ctgctaggca 1200
aggcccgcaa ggtcgtggtc accaaggacg agaccaccat cgtcgagggc gccggtgaca 1260
ccgacgccat cgccggacga gtggcccaga tccgccagga gatcgagaac agcgactccg 1320
actacgaccg tgagaagctg caggagcggc tggccaagct ggccggtggt gtcgcggtga 1380
tcaaggccgg tgccgccacc gaggtcgaac tcaaggagcg caagcaccgc atcgaggatg 1440
cggttcgcaa tgccaaggcc gccgtcgagg agggcatcgt cgccggtggg ggtgtgacgc 1500
tgttgcaagc ggccccgacc ctggacgagc tgaagctcga aggcgacgag gcgaccggcg 1560

```
ccaacatcgt gaaggtggcg ctggaggccc cgctgaagca gatcgccttc aactccgggc    1620
tggagccggg cgtggtggcc gagaaggtgc gcaacctgcc ggctggccac ggactgaacg    1680
ctcagaccgg tgtctacgag gatctgctcg ctgccggcgt tgctgacccg gtcaaggtga    1740
cccgttcggc gctgcagaat gcggcgtcca tcgcggggct gttcctgacc accgaggccg    1800
tcgttgccga caagccggaa aaggagaagg cttccgttcc cggtggcggc gacatgggtg    1860
gcatggattt ctgaccccgg cgagaagtcg cagcgaggag cccggtccct ttgtggggcc    1920
gggctcctct ggttgggagc tacggtaccg agaacaccac gcagtcgtgt aggcaacctt    1980
tggccgctgt gggcgagtcg ggggccgcgt ctcggtgcag cagcgcgcgg atgggtacga    2040
caccgcagcg ggcggtgtcg tcatcggggc ctgcgtccga cgcctgggca cggccgtcga    2100
cgatcagcga gtagccgcta ggatcggatg gcggccacaa caggtgact tcgctgcggt    2160 gggccaggtt ttgccgcgta cgaccccga tcaggccgac gtcgaccact gcccgggtc     2220 catcggggcc gtcggggagt tcgcgcagca ccggctcgac tgccaccgtg tgcacgcgat    2280
ggccatcatc gacggtgatc aggtaagcga acgggtagtc gggcaaggcg gcggccagcc    2340
gtttgaggtc taccttttg gcacccacgg attcgaggat aggcgcccga tgtgttactc     2400
cgaaccgacc ggctgcccga tccgcgggct ggcgtaggcg gattcgcggt cggggctcgg    2460
gtagaagttc gacttgggga tgccggagcc gggggtactc ggctcacgca cggcggtatt    2520
ccgcaagccc gagtcgttgc tgcccgagtt gacgaagctc gggtagctgg tgccagggct    2580
tctaaggccc gggtttgcgc ccgagccagc cgcggcactg ccgctaccgg ggttcgggtt    2640
gcctgagtcc aggccgccaa caggagcact ggccggggcg cgacgggcg tgttggtcag     2700 gcccgagttg aggacgttcg ccaggccgtg ttggagaccg cccgttgatc cgagggcgga    2760
ggcgaggatg cccgaactca aagccgccgt gctcatgccg ccggtggcgt agccggcgga    2820
gctgaccaag gccgcctccg agccagccgc gcttcctaag gcggcgttt gcatccccgc     2880 gttccagaag ctggtgttga ggctgcctgc gctgccgagg cccgcgttga ttgtccccga    2940
ggtcccgatg ccgctgttca gggagcccga attcccgatg ccgatgtttc cgctgccgga    3000
gttgaataag ccgacgttgc cggtgcccga gttcccgaag ccgatgttgc cgctacccga    3060
gttgaagccg ccgaaaccca tctggtgatc accggtgatc ccgaacccga tattcccgct    3120
accggtgttg ccgaagccga tattcccgtc gccgaggttg ccgaggccca ggttgccgct    3180
gccggtgttg ccgctgccga tgttgccggt gccggtgttg ccgctgccga tgttgttgtt    3240
gccgatgttg ttgttgccga tgttgttgtt gccgatgttg ccgctgccgg tgttgccgaa    3300
gcccagattg atctggccgt tcttgccgat gtcgatgccg aggttccgca agacctgctg    3360
ccagggcgcc agttgtgcga cggccgcaga cgcatcgaag tggtaaccag ccatcgccgc    3420
cacgtccaat gcccacattt gctcgtatgc cgcctcgacg tccatgagcg ccggagcgtt    3480
ctgcccaaac cagttcgtag ctgccagcag ctgcatcagg ccacgattgg ccgctaccac    3540
tgccggctga acgtggccg ccagcgccg ctcgaacgcg gtcgctgttg ccatggcctg      3600
tgcggccgct tgttccgcct gcgctgccgc cgtgctgagc caggctaggt actgggttgc    3660
gacggccatc atcgccgccg cggacggacc cagccaggcg ccactagtca gttcggatgt    3720
gacggagcca agcgacgcta ttgacgcgag caattcttcg gccagctcgc cccaggcggt    3780
ggccgcagca attagcggtc ccgacccggg accggcaaac atcagtgccg aattgatctc    3840
tggcggcaac cacgcaaaat gcgggcttgt cagccgatcc aacttaactg tcagcgaccg    3900
```

-continued

| | |
|---|---|
| ttgccgtggc ggtatcggca cttcaatacc actcatcttt ggggtcatct ttggagcgcc | 3960 |
| cctaggaacc gccagcttac ctagtcccgg gtaggggccg actggcggcc gggatgcagc | 4020 |
| tgagggtctg ccacctgccc cgtaatgtcg ctggtatggc aagcaccgac gccgcggccc | 4080 |
| aagagttgct ccgcgacgcg ttcacccggt tgatcgaaca tgtcgacgaa ctcaccgacg | 4140 |
| gcctcaccga ccaactcgcc tgctaccgcc cgaccccag cgccaacagc attgcgtggc | 4200 |
| tgctctggca cagcgcccgg gtgcaggata tacaggtcgc ccatgtggcc ggcgtggaag | 4260 |
| aggtgtggac ccgcgacggt tgggtggacc gctttgggtt agatctgccg cggcacgaca | 4320 |
| ccggatatgg acaccgtccc gaggatgtgg cgaaggtacg ggcacccgcc gacggaattc | 4380 |

<210> SEQ ID NO 4
<211> LENGTH: 21
<212> TYPE: DNA
<213> ORGANISM: Artificial Sequence
<220> FEATURE:
<223> OTHER INFORMATION: Unknown

<400> SEQUENCE: 4
gcgattacat cgccctgaac g                                         21

<210> SEQ ID NO 5
<211> LENGTH: 20
<212> TYPE: DNA
<213> ORGANISM: Artificial Sequence
<220> FEATURE:
<223> OTHER INFORMATION: Unknown

<400> SEQUENCE: 5
aggtccgtcg acagaagtgc                                           20

<210> SEQ ID NO 6
<211> LENGTH: 3740
<212> TYPE: DNA
<213> ORGANISM: Artificial Sequence
<220> FEATURE:
<223> OTHER INFORMATION: Synthetic

<400> SEQUENCE: 6

| | |
|---|---|
| cgataagctt ctgtggaatg tgtgtcagtt agggtgtgga aagtccccag gctccccagc | 60 |
| aggcagaagt atgcaaagca tgcatctcaa ttagtcagca accaggtgtg gaaagtcccc | 120 |
| aggctcccca gcaggcagaa gtatgcaaag catgcatctc aattagtcag caaccatagt | 180 |
| cccgccccta actccgccca tcccgcccct aactccgccc agttccgccc attctccgcc | 240 |
| ccatggctga ctaatttttt ttatttatgc agaggccgag gccgcctcgg cctctgagct | 300 |
| attccagaag tagtgaggag gcttttttgg aggcctaggc ttttgcaaaa agctcctccg | 360 |
| atcgaggggc tcgcatctct ccttcacgcg cccgccgccc tacctgaggc cgccatccac | 420 |
| gccggttgag tcgcgttctg ccgcctcccg cctgtggtgc ctcctgaact gcgtccgccg | 480 |
| tctaggtaag tttaaagctc aggtcgagac cgggcctttg tccggcgctc ccttggagcc | 540 |
| tacctagact cagccggctc tccacgcttt gcctgaccct gcttgctcaa ctctacgtct | 600 |
| ttgtttcgtt ttctgttctg cgccgttaca gatccaagct gcctcgagga actgaaaaac | 660 |
| cagaaagtta actggtaagt ttagtctttt tgtcttttat ttcaggtccc ggatccggtg | 720 |
| gtgcaaatca aagaactgct cctcagtgga tgttgccttt acttctaggc ctgtacggaa | 780 |
| gtgttacttc tgctctaaaa gctgctgcag agcttatcga tgataagctg tcaaacatga | 840 |
| gaattccaac ctttctggtt ttttgcgttt cccgtcaaca gtatcttccc cttcacaaaa | 900 |

```
ttgcagcaaa agctctaaaa caaacacaaa aaggcgttga gctgtttttt tactttcagt      960
ccatgaccta ctatcttccc cttcacaaaa ttgcagcaaa agctctaaaa caaacacaaa     1020
aaggcgttga gctgtttttt tactttcagt ccatgaccta cgaaccttaa cggaggcctg     1080
gcgtgacagc cggcgcagca ccatggcctg aaataacctc tgaaagagga acttggttag     1140
gggtaccttc tgaggcggaa agaaccagcc ggatccctcg aggatccaga catgataaga     1200
tacattgatg agtttggaca aaccacaact agaatgcagt gaaaaaaatg ctttatttgt     1260
gaaatttgtg atgctattgc tttatttgta accattataa gctgcaataa acaagttaac     1320
aacaacaatt gcattcattt tatgtttcag gttcaggggg aggtgtggga ggttttttaa     1380
agcaagtaaa acctctacaa atgtggtatg gctgattatg atcctgcctc gcgcgtttcg     1440
gtgatgacgg tgaaaacctc tgacacatgc agctcccgga gacggtcaca gcttgtctgt     1500
aagcggatgc cgggagcaga caagcccgtc agggcgcgtc agcgggtgtt ggcgggtgtc     1560
ggggcgcagc catgacccag tcacgtagcg atagcggagt gtatactggc ttaactatgc     1620
ggcatcagag cagattgtac tgagagtgca cgtcgaccgg tgtgaaatac cgcacagatg     1680
cgtaaggaga aaataccgca tcaggcgctc ttccgcttcc tcgctcactg actcgctgcg     1740
ctcggtcgtt cggctgcggc gagcggtatc agctcactca aaggcggtaa tacgttatc     1800 cacagaatca ggggataacg caggaaagaa catgtgagca aaaggccagc aaaaggccag     1860
gaaccgtaaa aaggccgcgt tgctggcgtt tttccatagg ctccgccccc ctgacgagca     1920
tcacaaaaat cgacgctcaa gtcagaggtg gcgaaacccg acaggactat aaagatacca     1980
ggcgtttccc cctggaagct ccctcgtgcg ctctcctgtt ccgaccctgc cgcttaccgg     2040
atacctgtcc gcctttctcc cttcgggaag cgtggcgctt tctcaatgct cacgctgtag     2100
gtatctcagt tcggtgtagg tcgttcgctc caagctgggc tgtgtgcacg aaccccccgt     2160
tcagcccgac cgctgcgcct tatccggtaa ctatcgtctt gagtccaacc cggtaagaca     2220
cgacttatcg ccactggcag cagccactgg taacaggatt agcagagcga ggtatgtagg     2280
cggtgctaca gagttcttga agtggtggcc taactacggc tacactagaa ggacagtatt     2340
tggtatctgc gctctgctga agccagttac cttcggaaaa agagttggta gctcttgatc     2400
cggcaaacaa accaccgctg gtagcggtgg ttttttgtt tgcaagcagc agattacgcg     2460
cagaaaaaaa ggatctcaag aagatccttt gatcttttct acgggtctg acgctcagtg     2520 gaacgaaaac tcacgttaag ggattttggt catgagatta tcaaaaagga tcttcaccta     2580 gatccttta aattaaaaat gaagttttaa atcaatctaa agtatatatg agtaaacttg     2640
gtctgacagt taccaatgct taatcagtga ggcacctatc tcagcgatct gtctatttcg     2700
ttcatccata gttgcctgac tccccgtcgt gtagataact acgatacggg agggcttacc     2760
atctggcccc agtgctgcaa tgataccgcg agacccacgc tcaccggctc cagatttatc     2820
agcaataaac cagccagccg gaagggccga gcgcagaagt ggtcctgcaa ctttatccgc     2880
ctccatccag tctattaatt gttgccggga agctagagta agtagttcgc cagttaatag     2940
tttgcgcaac gttgttgcca ttgctacagg catcgtggtg tcacgctcgt cgtttggtat     3000
ggcttcattc agctccggtt cccaacgatc aaggcgagtt acatgatccc ccatgttgtg     3060
caaaaaagcg gttagctcct tcggtcctcc gatcgttgtc agaagtaagt tggccgcagt     3120
gttatcactc atggttatgg cagcactgca taattctctt actgtcatgc catccgtaag     3180
atgcttttct gtgactggtg agtactcaac caagtcattc tgagaatagt gtatgcgcga     3240
```

-continued

| | | | | | |
|---|---|---|---|---|---|
| ccgagttgct | cttgcccggc | gtcaatacgg | gataataccg | cgccacatag | cagaacttta 3300 |
| aaagtgctca | tcattggaaa | acgttcttcg | gggcgaaaac | tctcaaggat | cttaccgctg 3360 |
| ttgagatcca | gttcgatgta | acccactcgt | gcacccaact | gatcttcagc | atcttttact 3420 |
| ttcaccagcg | tttctgggtg | agcaaaaaca | ggaaggcaaa | atgccgcaaa | aaagggaata 3480 |
| agggcgacac | ggaaatgttg | aatactactc | ttcctttttc | aatattattg | aagcatttat 3540 |
| cagggttatt | gtctcatgag | cggatacata | tttgaatgta | tttagaaaaa | taaacaaata 3600 |
| ggggttccgc | gcacatttcc | ccgaaaagtg | ccacctgacg | tctaagaaac | cattattatc 3660 |
| atgacattaa | cctataaaaa | taggcgtatc | acgaggccct | ttcgtcttca | aggtcgacct 3720 |
| catgtttgac | agcttatcat | | | | 3740 |